(12) United States Patent
Loftsson et al.

(10) Patent No.: US 11,491,240 B2
(45) Date of Patent: *Nov. 8, 2022

(54) PREPARATION OF SOLID CYCLODEXTRIN COMPLEXES FOR OPHTHALMIC ACTIVE PHARMACEUTICAL INGREDIENT DELIVERY

(71) Applicant: OCULIS SA, Reykjavik (IS)

(72) Inventors: Thorsteinn Loftsson, Reykjavik (IS); Zoltan Fulop, Reykjavik (IS)

(73) Assignee: OCULIS SA, Lausanne (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/487,354

(22) Filed: Sep. 28, 2021

(65) Prior Publication Data
US 2022/0008555 A1   Jan. 13, 2022

Related U.S. Application Data

(63) Continuation of application No. 15/826,247, filed on Nov. 29, 2017, now Pat. No. 11,135,311.

(60) Provisional application No. 62/427,737, filed on Nov. 29, 2016.

(51) Int. Cl.
| | | |
|---|---|---|
| *A61K 47/69* | (2017.01) |
| *A61K 47/34* | (2017.01) |
| *A61P 27/02* | (2006.01) |
| *A61K 9/00* | (2006.01) |
| *A61K 9/08* | (2006.01) |
| *A61K 9/10* | (2006.01) |
| *A61K 9/14* | (2006.01) |
| *A61K 9/50* | (2006.01) |
| *A61K 9/51* | (2006.01) |
| *A61K 31/4184* | (2006.01) |
| *A61K 31/573* | (2006.01) |
| *A61K 47/02* | (2006.01) |
| *A61K 47/10* | (2017.01) |
| *A61K 47/12* | (2006.01) |
| *A61K 47/18* | (2017.01) |
| *A61K 47/38* | (2006.01) |
| *A61K 47/40* | (2006.01) |

(52) U.S. Cl.
CPC ........ *A61K 47/6951* (2017.08); *A61K 9/0048* (2013.01); *A61K 9/08* (2013.01); *A61K 9/10* (2013.01); *A61K 9/146* (2013.01); *A61K 9/50* (2013.01); *A61K 9/51* (2013.01); *A61K 31/4184* (2013.01); *A61K 31/573* (2013.01); *A61K 47/02* (2013.01); *A61K 47/10* (2013.01); *A61K 47/12* (2013.01); *A61K 47/186* (2013.01); *A61K 47/34* (2013.01); *A61K 47/38* (2013.01); *A61P 27/02* (2018.01); *A61K 47/40* (2013.01)

(58) Field of Classification Search
CPC ..... A61P 27/02; A61K 47/6951; A61K 47/34; A61K 9/0048; A61K 9/08; A61K 9/10; A61K 9/146; A61K 9/50; A61K 9/51; A61K 31/4184; A61K 31/573; A61K 47/02; A61K 47/10; A61K 47/12; A61K 47/186; A61K 47/38; A61K 47/40

See application file for complete search history.

(56) References Cited

U.S. PATENT DOCUMENTS

| | | | |
|---|---|---|---|
| 7,893,040 B2 | 2/2011 | Loftsson et al. | |
| 8,633,172 B2 | 1/2014 | Loftsson et al. | |
| 8,999,953 B2 | 4/2015 | Loftsson et al. | |
| 10,159,746 B2 | 12/2018 | Lewis et al. | |
| 11,135,311 B2* | 10/2021 | Loftsson | ................. A61K 47/38 |
| 2002/0198174 A1* | 12/2002 | Lyons | ..................... B82Y 5/00 |
| | | | 514/26 |
| 2004/0077562 A1* | 4/2004 | Chandavarkar | ...... A61K 9/0048 |
| | | | 514/36 |
| 2007/0020336 A1* | 1/2007 | Loftsson | ................. A61P 31/12 |
| | | | 514/3.7 |
| 2007/0148192 A1* | 6/2007 | Laddha | .............. A61K 31/4709 |
| | | | 514/35 |
| 2014/0057854 A1* | 2/2014 | Mitra | ...................... A61P 29/00 |
| | | | 514/20.5 |
| 2015/0111838 A1 | 4/2015 | Lewis et al. | |

FOREIGN PATENT DOCUMENTS

WO   2004069280 A1   8/2004

OTHER PUBLICATIONS

Thorsteinn Loftsson, et al., Cyclodextrin Microparticles for Drug Delivery to the Posterior Segment of the Eye: Aqueous Dexamethasone Eye Drops, 59 J Pharm. Pharmacol. 629 (Year: 2007).*
Marcus E. Brewster et al., "Cyclodextrins as pharmaceutical solubilizers", Advanced Drug Delivery Reviews, vol. 59, pp. 645-666 (2007).
E. M. Cohen, "Dexamethasone. Analytical Profiles of Drug Substances", vol. 2, pp. 163-197 (1973).
Raymond E. Conrow et al., "Corticosteroid Decomposition via a Mixed Anhydride", The Journal of Organic Chemistry, vol. 67, pp. 6835-6836 (2002).
M. Spangler et al.,"A validated, stability-indicating method for the assay of dexamethasone in drug substance and drug product analyses, and the assay of preservatives in drug product", Chromatographia, vol. 54, pp. 329-334.

(Continued)

*Primary Examiner* — Sean M Basquill
(74) *Attorney, Agent, or Firm* — Sheppard, Mullin, Richter & Hampton LLP

(57) ABSTRACT

The present disclosure relates to ophthalmic compositions containing solid complexes of active pharmaceutical ingredient and cyclodextrin, to their method of preparation and their uses. The compositions can include an active agent drug/cyclodextrin complex substantially dissolved in an aqueous eye drop vehicle. The ophthalmic composition is generally in the form of a microsuspension including an active agent complex having a diameter of less than about 100 μm.

360 Claims, 2 Drawing Sheets

(56) References Cited

OTHER PUBLICATIONS

Teturo Hidaka et al., "Studies on Betamethasone: Behavior of Betamethasone in Acid or Alkaline Medium, Photolysis and Oxidation", Yakugaku Zasshi, vol. 100, No. 1, pp. 72-80 (1980).
Renu Chadha et al., "Kinetics of degradation of diclofenac sodium in aqueous solution determined by a calorimetric method", Die Pharmazie, vol. 58, pp. 631-635 (2003).
Phatsawee Jansook et al., "γCD/HPγCD mixtures as solubilizer: solid-state characterization and sample dexamethasone eye drop suspension", Journal of Pharmacy & Pharmaceutical Sciences, vol. 13, No. 3, pp. 336-350 (2010).
Final Office Action dated Jun. 1, 2021 in U.S. Appl. No. 16/465,138.
Search Report dated Sep. 11, 2020, issued in corresponding Singapore Patent Application No. 11201904849T, 3 pages.
Le Bourlais, C., Acar, L., Zia, H., Sada, P.A., Needham, T., Leverge, R., 1998, "Ophthalmic drug delivery systems-Recent advances. Progress in Retinal and Eye Research", vol. 17, pp. 33-58.
Gan, L., Wang, J., Jiang, M., Bartlett, H., Ouyang, D., Eperjesi, F., Liu, J., Gan, Y., 2013, "Recent advances in topical ophthalmic drug delivery with lipid-based nanocarriers". Drug Discov Today, vol. 18, pp. 290-297.
Loftsson, T., Sigurdsson, H.H., Konradsdottir, F., Gisladottir, S., Jansook, P., Stefansson, E., 2008, "Topical drug delivery to the posterior segment of the eye: anatomical and physiological considerations", Pharmazie, vol. 63, pp. 171-179.
Urtti, A., 2006, "Challenges and obstacles of ocular pharmacokinetics and drug delivery", Adv. Drug Del. Rev., vol. 58, pp. 1131-1135.
Loftsson, T., Jarvinen, T., 1999, "Cyclodextrins in ophthalmic drug delivery", Advanced Drug Delivery Reviews, vol. 36, pp. 59-79.
Sugrue, M.F., 1989, "The pharmacology of antiglaucoma drugs", Pharmacology & Therapeutics, vol. 43, pp. 91-138.
Johannessen, G., Moya-Ortega, M.D., Asgrimsdottir, G.M., Lund, S.H., Thorsteinsdottir, M., Loftsson, T., Stefansson, E., 2014, "Kinetics of γ-cyclodextrin nanoparticle suspension eye drops in tear fluid. Acta Ophthalmologica", vol. 92, pp. 550-556.
Loftsson, T., Jansook, P., Stefansson, E., 2012, "Topical drug delivery to the eye: dorzolamide", Acta Ophthalmologica vol. 90, pp. 603-608.
Lawen, A., 2015, "Biosynthesis of cyclosporins and other natural peptidyl prolyl cis/trans isomerase inhibitors", Biochimica et Biophysica Acta, vol. 1850, pp. 2111-2120.
Peel, M., Sctiber, A., 2015, "Semi-synthesis of cyclosporins", Biochimica et Biophysica Acta, vol. 1850, pp. 2121-2144.
Laupacis, A., Keown, P.A., Ulan, R.A., McKenzie, N., Stiller, C.R., 1982, "Cyclosporin A: a powerful immunosuppressant", Canadian Medical Association Journal, vol. 126, pp. 1041-1046.
El Tayar, N., Mark, A.E., Vallat, P., Brunne, R.M., Testa, B., Gunsteren, W.F.v., 1993, "Solvent-dependent conformation and hydrogen-bonding capacity of cyclosporin A: evidence from partition coefficients and molecular • dynamics simulations", J. Med. Chem., vol. 36, pp. 3753-3764.
Loftsson, T., Hreinsdottir, D., 2006, Determination of aqueous solubility by heating and equilibration: A technical note. Aaps Pharmscitech 7, article No. 4.
Utine, C.A., Stern, M., Akpek, E.K., 2010, "Clinical Review: Topical Ophthalmic Use of Cyclosporin A. Ocular Immunology & Inflammation", vol. 18, pp. 352-361.
Miyake, K., Arima, H., Irie, T., Hirayama, F., Uekama, K., 1999, "Enhanced absorption of cyclosporin A by complexation with dimethyl-beta-cyclodextrin in bile duct-cannulated and -noncannulated rats", Biological & Pharmaceutical Bulletin, vol. 22, pp. 66-72.
Kurkov, S.V., Loftsson, T., 2013, "Cyclodextrins", Int. J. Pharm., vol. 453, pp. 167-180.
Loftsson, T., Brewster, M.E., 1996, "Pharmaceutical applications of cyclodextrins. 1. Drug solubilization and stabilization", Journal of Pharmaceutical Sciences, vol. 85, pp. 1017-1025.
Stella, V.J., He, Q., 2008, "Cyclodextrins", Tax. Pathol., vol. 36, pp. 30-42.
Loftsson, T., Brewster, M.E., 2010, "Pharmaceutical applications of cyclodextrins: basic science and product development", Journal of Pharmacy and Pharmacology, vol. 62, pp. 1607-1621.
Loftsson, T., Brewster, M.E., 2011, "Pharmaceutical applications of cyclodextrins: effects on drug permeation through biological membranes", J. Pharm. Pharmacol. 63, pp. 1119-1135.
Higuchi, T., Connors, K. A., 1965, "Phase solubility techniques. Advanced Analytical Chemistry of Instrumentation 4", pp. 117-212.
J. Horsky and J. Pitha., 1994, "Inclusion complexes of proteins: interaction of cyclodextrins with peptides containing aromatic amino acids studies by competitive spectrophotometry", J. Inclusion Phenom. Mal. Recognit. Chem., vol. 18, pp. 291-300.
Bonini, M., Rossi, S., Karlsson, G., Almgren, M., Lo Nostro, P., Baglioni, P., 2006, Self-assembly of beta-cyclodextrin in water. Part 1: Cryo-TEM and dynamic and static light scattering. Langmuir 22, pp. 1478-1484.
He, Y., Fu, P., Shen, X., Gao, H., 2008, "Cyclodextrin-based aggregates and characterization by microscopy", Micron, vol. 39, pp. 495-516.
Loftsson, T., 2014, "Self-assembled cyclodextrin nanoparticles and drug delivery", J. Incl. Phenom. Macro., vol. 80, pp. 1-7.
Messner, M., Kurkov, S.V., Jansook, P., Loftsson, T., 2010, "Self-assembled cyclodextrin aggregates and nanoparticles", Int. J. Pharm., vol. 387, pp. 199-208.
Gudmundsdottir, B.S., Petursdottir, D., Asgrimsdottir, G.M., Gottfredsdottir, M.S., Hardarson, S.H., Johannessen, G., Kurkov, S.V., Jansook, P., Loftsson, T., Stefansson, E., 2014, "γ-Cyclodextrin nanoparticle eye drops with dorzolamide: effect on intraocular pressure in man", J. Ocul. Pharmacol. Ther., vol. 30, pp. 35-41.
Tanito, M., Hara, K., Takai, Y., Matsuoka, Y., Nishimura, N., Jansook, P., Loftsson, T., Stefansson, E., Ohira, A., 2011, "Topical dexamethasone-cyclodextrin microparticle eye drops for diabetic macular edema", Invest. Ophth. Vis. Sci., vol. 52, pp. 7944-7948.
Muankaew, C., Jansook, P., Stefansson, E., Loftsson, T., 2014, "Effect of γ-cyclodextrin on solubilization and complexation of irbesartan: influence of pH and excipients", Int. J. Pharm., vol. 474, pp. 80-90.
Kunert, K.S., Tisdale, A.S., Gipson, I.K., 2002, "Goblet cell numbers and epithelial proliferation in the conjunctiva of patients with dry eye syndrome treated with cyclosporine", Archives of Ophthalmology, vol. 120, pp. 330-337.
Kanai, A., Alba, R.M., Takano, T., Kobayashi, C., Nakajima, A., Kurihara, K., Yokoyama, T., Fukami, M., 1989, "The affect on the cornea of alpha cyclodextrin vehicle for cyclosporin eye drops", Transplant. Proc., vol. 21, pp. 3150-3152.
Johannsdottir S., Kristinsson J.K., Fulop Z., Asgrfmsd6ttir G., Stefansson E., Loftsson T., 2017, "Formulations and toxicologic in vivo studies of aqueous cyclosporin A eye drops with cyclodextrin nanoparticles", Int. J. Pharm., vol. 529, pp. 486-490.
Johannsdottir S., Jansook P., Stefansson E., Loftsson T., 2015, "Development of a cyclodextrin-based aqueous cyclosporin A eye drop formulations", Int. J. Pharm., vol. 493, pp. 86-95.
2.9.31. Particle Size Analysis by Laser Light Diffraction, European Pharmacopeia 9.0, pp. 349-352.
Bhatia, Saurabh, 2016, "Chapter 2: Nanoparticles Types, Classification, Characterization, Fabrication methods and Drug Delivery Applications", Natural Polymer Drug Delivery Systems, pp. 33-93.
Stamm, Hermann, 2009, "Overview of the Methods and Techniques of Measurement of Nanoparticles", nanotrust—Possible Health Effects of Manufactured Nanomaterials, 52 pages.
Jozwiakowski, Michael J. and Connors, Kenneth A., 1985, "Aqueous solubility behavior of three cyclodextrins", Carbohydrate Research, vol. 143, pp. 51-59.
Jansook, Phatsawee, Moya-Ortega, Maria D. and Loftsson, Thorsteinn, 2010, "Effect of self-aggregation of γ-cyclodextrin on drug solubilization", Journal of Inclusion Phenomena and Macrocyclic Chemistry, vol. 68, pp. 229-236.
Chen, Bin, Li, Min, Mingxiang, Lin, Tumambac, Gilbert and Rustum, Abu, 2009, "A comparative study of enol aldehyde orma-

(56) References Cited

OTHER PUBLICATIONS tion from betamethasone, dexamethasone, beclomethasone and related compounds under acidic and alkaline conditions", Steroids, vol. 74, No. 1, pp. 30-41.
Non-Final Office Action dated Sep. 29, 2021 in U.S. Appl. No. 16/465,138.
Dalton, PH, Osmolality and Viscosity of Artificial Tears, American Academy of Optometry, downloaded from <URL https://www.aaopt.org/detail/knowledge-base-article/ ph-osmolality-and-viscosity-artificial-tears > on Sep. 24, 2021, 2 pages (2008).
Kabat et al., "Not All Tears Are Created Equal", Review of Optometry, vol. 142(1), 3 pages (2005).

* cited by examiner

PREPARATION OF SOLID CYCLODEXTRIN COMPLEXES FOR OPHTHALMIC ACTIVE PHARMACEUTICAL INGREDIENT DELIVERY

CROSS-REFERENCE TO PRIOR APPLICATIONS

This application is a Continuation Application to U.S. patent application Ser. No. 15/826,247, filed Nov. 29, 2017 which claims priority under 35 U.S.C. § 120 to Provisional Application No. 62/427,737, filed Nov. 29, 2016, each hereby expressly incorporated by reference in its entirety and each assigned to the assignee hereof.

FIELD

The present disclosure relates to ophthalmic compositions containing solid complexes of active pharmaceutical ingredient and cyclodextrin, to their method of preparation and their uses. The present disclosure also relates to bottom-up preparation of novel aqueous eye drop compositions containing drug/cyclodextrin nanoparticles.

BACKGROUND

In this specification where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

According to the National Eye Institute a division of the National Institutes of Health, ocular conditions cause an estimated $139 billion economic burden in America alone. This number is not surprising considering that 2.1 million Americans are diagnosed with age-related macular degeneration (AMD), 2.7 million Americans are diagnosed with glaucoma, 7.7 million Americans are diagnosed with diabetic retinopathy, and 24 million Americans are diagnosed with cataracts. Ocular conditions are not just a problem in the United States. In fact, approximately 285 million people worldwide are estimated to be visually impaired.

Most ocular conditions can be treated and/or managed to reduce negative effects, including total blindness. To combat this significant problem, the World Health Organization (WHO) approved an action plan with the aim of reducing 25% of the world's avoidable visual impairments by 2019. In its efforts, the WHO plan to reduce the effects of ocular conditions such as diabetic retinopathy, glaucoma, and retinitis pigmentosa, which account for most cases of irreversible blindness worldwide. However, current treatments for ocular conditions are limited by the difficulty in delivering effective doses of drugs to target tissues in the eye.

In current treatments, topical administration of eye drops is the preferred means of drug administration to the eye due to the convenience and safety of eye drops in comparison to other routes of ophthalmic drug administration such as intravitreal injections and implants (Le Bourlais, C., Acar, L., Zia, H., Sado, P. A., Needham, T., Leverge, R., 1998. Ophthalmic drug delivery systems—Recent advances. Progress in Retinal and Eye Research 17, 33-58). Drugs are mainly transported by passive diffusion from the eye surface into the eye and surrounding tissues where, according to Fick's law, the drug is driven into the eye by the gradient of dissolved drug molecules. The passive drug diffusion into the eye is hampered by three major obstacles (Gan, L., Wang, J., Jiang, M., Bartlett, H., Ouyang, D., Eperjesi, F., Liu, J., Gan, Y., 2013. Recent advances in topical ophthalmic drug delivery with lipid-based nanocarriers. Drug Discov. Today 18, 290-297; Loftsson, T., Sigurdsson, H. H., Konradsdottir, F., Gisladottir, S., Jansook, P., Stefansson, E., 2008. Topical drug delivery to the posterior segment of the eye: anatomical and physiological considerations. Pharmazie 63, 171-179; Urtti, A., 2006. Challenges and obstacles of ocular pharmacokinetics and drug delivery. Adv. Drug Del. Rev. 58, 1131-1135).

The first major obstacle is the aqueous drug solubility. In previously known ophthalmic compositions, only dissolved drug molecules can permeate through biological membranes into the eye. Accordingly, ophthalmic drugs must possess sufficient solubility in the aqueous tear fluid to permeate into the eye.

The second major obstacle is the rapid turnover rate of the tear fluid and the consequent decrease in concentration of dissolved drug molecules. Following instillation of an eye-drop (25-50 µl) onto the pre-corneal area, the greater part of the drug solution is rapidly drained from the eye surface and the tear volume returns to the normal resident volume of about 7 µl. Thereafter, the tear volume remains constant, but drug concentration decreases due to dilution by tear turnover and corneal and non-corneal drug absorption. The value of the first-order rate constant for the drainage of eye drops from the surface area is typically about 1.5 $min^{-1}$ in humans after the initial rapid drainage. Normal tear turnover is about 1.2 µl/min in humans and the pre-corneal half-life of topically applied drugs is between 1 and 3 minutes (Sugrue, M. F., 1989. The pharmacology of antiglaucoma drugs. Pharmacology & Therapeutics 43, 91-138).

The third major obstacle is slow drug permeation through the membrane barrier, i.e. cornea and/or conjunctiva/sclera. The drug molecules must partition from the aqueous exterior into the membrane before they can passively permeate the membrane barrier. The result is that generally only few percentages of applied drug dose are delivered into the ocular tissues. The major part (50-100%) of the administered dose will be absorbed from the nasal cavity into the systemic drug circulation which can cause various side effects.

The present disclosure seeks to assist with the WHO's plan for reducing avoidable visual impairments by providing an ophthalmic composition and a method of making an ophthalmic composition that overcomes the obstacles of passive drug diffusion in the eye. In these efforts, Applicants provide a method for preparing an ophthalmic composition, which overcomes the major obstacles of passive drug diffusion by (1) increasing the solubility of poorly soluble drugs, (2) increasing the precorneal half-life of topically applied drugs, and (3) partitioning drug molecules from the aqueous exterior into the membrane to enable passive permeation of the membrane barrier. In exemplary embodiments, ophthalmic compositions comprising a combination of such features are provided.

SUMMARY

Cyclodextrins are well-known to enhance the solubility and bioavailability of hydrophobic compounds. In aqueous solutions, cyclodextrins form inclusion complexes with many active pharmaceutical ingredients. The bottom-up preparation of active pharmaceutical ingredient/cyclodextrin complexes involves suspending an active pharmaceutical ingredient and a cyclodextrin in an aqueous medium and heating the resulting suspension. Upon dissolution of the active pharmaceutical ingredient and the cyclodextrin, complexes of active pharmaceutical ingredient and cyclodextrin are formed. The hot solution is subsequently cooled to precipitate the solid complexes of active pharmaceutical ingredient and cyclodextrin.

Applicants have surprisingly found that the diameter of the particles and the viscosity of the composition can be tailored with the heating and cooling steps and the presence of stabilizing polymers in the aqueous medium. To prevent or substantially inhibit or reduce formation of impurities, such as degradation product derived from the active pharmaceutical ingredient and/or excipients, Applicants have discovered that excessive heating of the medium should be avoided and that the hot solution should be rapidly cooled to room temperature.

Furthermore, the composition of the disclosure exhibits enhanced viscosity which prevents sedimentation of the microparticles during storage and also advantageously increases the contact time of the particles on the surface of the eye thus improving the bioavailability of the active pharmaceutical ingredient.

Applicants have discovered an exemplary ophthalmic composition and a method of making the composition, which overcomes the known major obstacles of passive drug diffusion.

A first object of the present disclosure is an ophthalmic composition comprising, in an ophthalmically acceptable medium, a solid complex comprising an active pharmaceutical ingredient and a cyclodextrin, wherein the composition comprises less than 2%, in particular less than 1%, more particularly less than 0.8%, by weight of impurities based on the weight of the active pharmaceutical ingredient.

A second object of the present disclosure is an ophthalmic composition comprising, in an ophthalmically acceptable medium, a solid complex comprising an active pharmaceutical ingredient and a cyclodextrin; and a polymer; wherein the viscosity of the composition is from 4 to 14 cP, preferably 5 to 13 cP, more preferably 6 to 12 cP.

A third object of the present disclosure is an ophthalmic composition comprising, in an ophthalmically acceptable medium, a solid complex comprising dexamethasone and γ-cyclodextrin, wherein the composition comprises less than 0.5%, in particular less than 0.3%, more particularly less than 0.2%, by weight of 16,17-unsaturated dexamethasone or a mixture of enol aldehydes based on the weight of the dexamethasone.

A fourth object of the present disclosure is an ophthalmic composition comprising, in an ophthalmically acceptable medium, a solid complex comprising dexamethasone and γ-cyclodextrin; and a polymer; wherein the viscosity of the composition is from 4 to 14 cP, preferably 5 to 13 cP, more preferably 6 to 12 cP.

The ophthalmic compositions of the disclosure are generally in the form of microsuspensions comprising a solid complex that may exhibit a diameter of less than about 100 μm. The compositions containing natural α-cyclodextrin, β-cyclodextrin or γ-cyclodextrin and methods provided by the disclosure provide from about 10-fold to about 100-fold increase in the concentration of dissolved active pharmaceutical ingredient available compared to conventional ophthalmic compositions prepared using previously-known methods. Moreover, the exemplary methods provide ophthalmic composition with decreased concentration of impurities and/or increased viscosity.

The disclosure also provides methods for preparing ophthalmic compositions having a high concentration of microparticle active pharmaceutical ingredient/cyclodextrin complex. Moreover, the methods of the disclosure provide ophthalmic composition with decreased concentration of impurities and/or increased viscosity.

As such, a fifth object of the disclosure is a method of preparing an ophthalmic composition, wherein an active pharmaceutical ingredient and a cyclodextrin are suspended in an ophthalmically acceptable medium to form a suspension. The suspension is then heated at a temperature T1 lower than 120° C. for a time t until the active pharmaceutical ingredient and the cyclodextrin are substantially dissolved in the ophthalmically acceptable medium. The resulting solution is then cooled to a temperature T2 to obtain an ophthalmic composition comprising a solid complex of an active pharmaceutical ingredient and a cyclodextrin.

A sixth object of the disclosure is a method of preparing an ophthalmic composition wherein a cyclodextrin is suspended in an ophthalmically acceptable medium to form a suspension. The suspension is then heated until the cyclodextrin is substantially dissolved in the ophthalmically acceptable medium. An active pharmaceutical ingredient is then added in solid form in said solution at a temperature T1 lower than 120° C. and the mixture is heated at a temperature T1 lower than 120° C. for a time t until the active pharmaceutical ingredient is substantially dissolved in the ophthalmically acceptable medium. The resulting solution is subsequently cooled to a temperature T2 to obtain an ophthalmic composition comprising a solid complex of an active pharmaceutical ingredient and a cyclodextrin.

A seventh object of the disclosure is a method of preparing an ophthalmic composition, wherein an active pharmaceutical ingredient is suspended in an ophthalmically acceptable medium to form a suspension and said suspension is heated until the active pharmaceutical ingredient is substantially dissolved in the ophthalmically acceptable medium. Separately, a cyclodextrin is suspended in an ophthalmically acceptable medium to form a suspension and said suspension is heated until the cyclodextrin is substantially dissolved in the ophthalmically acceptable medium. Both compositions are then mixed at a temperature T1 lower than 120° C. and the mixture is heated at a temperature T1 lower than 120° C. for a time t. The resulting solution is then cooled to a temperature T2 to obtain an ophthalmic composition comprising a solid complex of an active pharmaceutical ingredient and a cyclodextrin.

An eighth object of the disclosure is a method of preparing an ophthalmic composition, wherein dexamethasone and γ-cyclodextrin are suspended in an ophthalmically acceptable medium to form a suspension. The suspension is then heated at a temperature T1 lower than 120° C. for a time t until the dexamethasone and the γ-cyclodextrin are substantially dissolved in the ophthalmically acceptable medium. The resulting solution is then cooled to a temperature T2 to obtain an ophthalmic composition comprising a solid complex of dexamethasone and γ-cyclodextrin.

A ninth object of the disclosure is a method of preparing an ophthalmic composition, wherein γ-cyclodextrin is suspended in an ophthalmically acceptable medium to form a suspension. The suspension is then heated until the γ-cyclodextrin is substantially dissolved in the ophthalmically acceptable medium. Dexamethasone is then added in solid form in said solution at a temperature T1 lower than 120° C. and the mixture is heated at a temperature T1 lower than 120° C. for a time t until the dexamethasone is substantially dissolved in the ophthalmically acceptable medium. The resulting solution is subsequently cooled to a temperature T2 to obtain an ophthalmic composition comprising a solid complex of dexamethasone and γ-cyclodextrin.

An tenth object of the disclosure is a method of preparing an ophthalmic composition, wherein dexamethasone is suspended in an ophthalmically acceptable medium to form a suspension and said suspension is heated until the dexamethasone is substantially dissolved in the ophthalmically acceptable medium. Separately, γ-cyclodextrin is suspended in an ophthalmically acceptable medium to form a suspension and said suspension is heated until the γ-cyclodextrin is substantially dissolved in the ophthalmically acceptable medium. Both compositions are then mixed at a temperature T1 lower than 120° C. and the mixture is heated at a temperature T1 lower than 120° C. for a time t. The resulting solution is then cooled to a temperature T2 to obtain an ophthalmic composition comprising a solid complex of dexamethasone and γ-cyclodextrin.

An eleventh object of the disclosure is an ophthalmic composition obtainable by a method according to the disclosure.

A twelfth object of the disclosure is an ophthalmic composition according to the disclosure or prepared according to the method of the disclosure for use in the treatment of an ocular condition, in particular an anterior ocular condition or a posterior ocular condition, more particularly uveitis, macular edema, macular degeneration, retinal detachment, ocular tumors, fungal or viral infections, multifocal choroiditis, diabetic retinopathy, proliferative vitreoretinopathy (PVR), sympathetic ophthalmia, Vogt Koyanagi-Harada (VKH) syndrome, histoplasmosis, uveal diffusion, and vascular occlusion.

A thirteenth object of the disclosure is an ophthalmic composition according to the disclosure or prepared according to the method of the disclosure for use in the treatment of macular edema, wherein the composition is topically administered to the eye in an amount of 1 drop of composition three times per day.

A fourteenth object of the disclosure is a use of an ophthalmic composition according to the disclosure or prepared according to the method of the disclosure as an eye drop solution.

In exemplary embodiments, an ophthalmic composition comprises an active agent drug/cyclodextrin complex dissolved in an aqueous eye drop vehicle. The ophthalmic composition is generally in the form of a microsuspension comprising an active agent complex having a diameter of less than about 100 μm. The compositions and methods provided by the exemplary embodiments provide about 10 to 100 fold increase in the concentration of dissolved active agent (i.e. drug) available in conventional ophthalmic compositions prepared using previously-known methods. Moreover, the exemplary methods provide ophthalmic composition with decreased concentration of degradation product.

The term "active agent," as used herein, can also be referred to, for example, as a pharmaceutical ingredient, an active pharmaceutical ingredient, an ophthalmic active pharmaceutical ingredient or a drug (or variations thereof). And, as used herein these terms (and variations thereof) can be considered equivalent and interchangeable. Exemplary embodiments provide methods for preparing ophthalmic compositions having a high concentration of microparticle active agent/cyclodextrin complex, and that does not generate or produce a by-product and/or degradation product for at least about 90 days when stored at room temperature.

According to one method, an active agent (or drug or other equivalent term) and at least one cyclodextrin are suspended in an aqueous eye drop vehicle to provide a suspension having a milky appearance. The suspension is heated for a sufficient time at a sufficient temperature until the drug and cyclodextrin are dissolved in the aqueous eye drop solution, and no or substantially no degradation and/or by-product is formed. Once the drug and the cyclodextrin are dissolved, the milky suspension turns into a substantially clear solution. The resulting solution is cooled at a rate sufficient to produce a microsuspension comprising a microparticle drug/cyclodextrin complex.

In another method, an active agent, at least one cyclodextrin, and at least one polymer are suspended in an aqueous eye drop vehicle to provide a suspension having a milky appearance. The suspension is heated for a sufficient time at a sufficient temperature until the drug, cyclodextrin, and the polymer are dissolved or substantially dissolved in the aqueous eye drop solution, and no degradation or substantially no degradation and/or by-product is formed. Once the drug, the cyclodextrin, and the polymer are dissolved the milky suspension turns into a substantially clear solution. The resulting solution is cooled at a rate sufficient to produce a microsuspension comprising a microparticle drug/cyclodextrin/polymer complex.

In a further method, at least one cyclodextrin is suspended in an aqueous eye drop vehicle to provide a suspension having a milky appearance. The suspension is heated for a sufficient time at a sufficient temperature until the cyclodextrin is dissolved (or substantially dissolved) in the aqueous eye drop solution, and no degradation or substantially no degradation and/or by-product is formed. Once the cyclodextrin is dissolved the milky suspension turns into a substantially clear solution. An active agent is added to the heated aqueous suspension, while stirring the solution, until the drug is dissolved or substantially dissolved in the solution. The resulting solution is cooled at a rate sufficient to produce a microsuspension comprising a microparticle drug/cyclodextrin complex.

In yet another method, cyclodextrin and at least one polymer are suspended in an aqueous eye drop vehicle to provide a suspension having a milky appearance. The suspension is heated for a sufficient time at a sufficient temperature until the cyclodextrin and the polymer are dissolved or substantially dissolved in the aqueous eye drop solution, and no degradation or substantially no degradation and/or by-product is formed. Once the cyclodextrin and the polymer are dissolved, the milky suspension turns into a substantially clear solution. An active agent is added to the heated aqueous suspension, while stirring the solution, until the drug is dissolved in the solution. The resulting solution is cooled at a rate sufficient to produce a microsuspension comprising a microparticle drug/cyclodextrin/polymer complex.

In still another method, at least one cyclodextrin is suspended in water or an aqueous eye drop vehicle to provide a suspension having a milky appearance. Separately the drug is suspended in water or an eye drop vehicle free of cyclodextrin to provide a suspension having a milky appearance. The two suspensions are sterilized by, for example, heating in an autoclave at 121° C. for 20 minutes. Then the two suspensions or hot solutions are allowed to cool to about 95° C. before mixing to form a substantially clear solution, and no degradation or substantially no degradation and/or by-product is formed. The resulting solution is cooled at a rate sufficient to produce a microsuspension comprising a microparticle drug/cyclodextrin complex.

In a non-limiting embodiment, at least one cyclodextrin is suspended in water or an aqueous eye drop vehicle to provide a suspension having a milky appearance. Separately, the active pharmaceutical ingredient is suspended in water or an eye drop vehicle free of cyclodextrin to provide a suspension having a milky appearance. The two suspensions are heated or sterilized by, for example, heating in an autoclave at 121° C. for 20 minutes. Then the two suspensions or hot solutions are mixed together and the temperature is adjusted to about 90° C. to about 95° C. to form a substantially clear solution, and no degradation or substantially no degradation and/or by-product is formed. The resulting solution is cooled at a rate sufficient to produce a microsuspension comprising a microparticle drug/cyclodextrin complex.

BRIEF DESCRIPTION OF THE DRAWINGS

These and other features of this disclosure will now be described with reference to the drawings of certain embodiments which are intended to illustrate and not to limit the disclosure.

Figure 1:
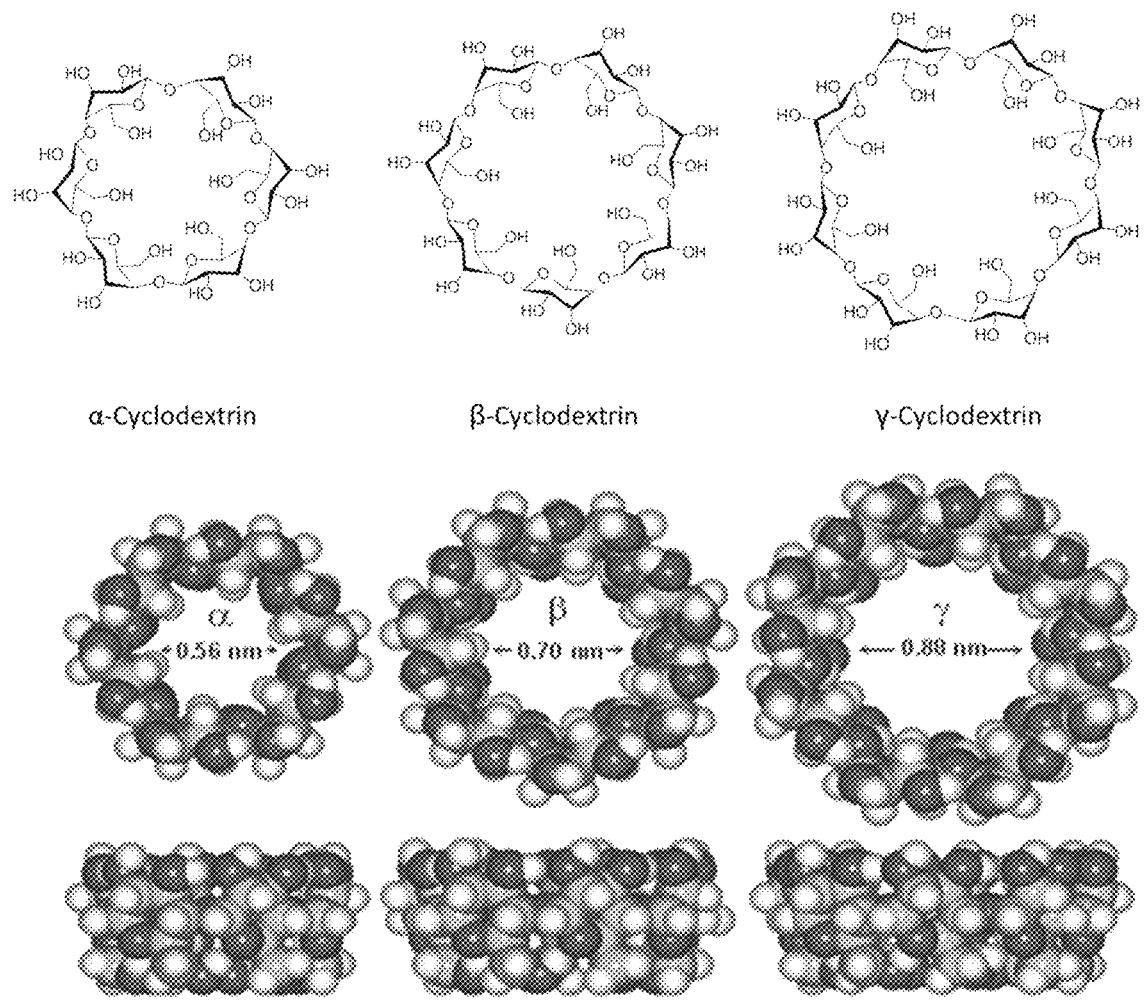
FIG. 1 depicts the structures of the natural α-cyclodextrin, β-cyclodextrin, and γ-cyclodextrin.

Thus, the amount of drug dissolved in solution is constant at γCD concentrations above 3% (w/v). The amount of γCD dissolved in solution increases slower than the amount of γCD that is added to the media, the change only becomes linear after 10% (w/v). This shows that at γCD concentrations between about 3-10% (w/v), all γCD added to the media forms solid complexes with the drug and precipitates. At γCD concentrations above 10% (w/v) the amount of dissolved γCD shows again a linear increase.

DETAILED DESCRIPTION

Further aspects, features and advantages of the exemplary embodiments will become apparent from the detailed description which follows.

The patents, published applications and scientific literature referred to herein establish the knowledge of those with skill in the art and are hereby incorporated by reference in their entireties to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

As used herein, whether in a transitional phrase or in the body of a claim, the terms "comprise(s)" and "comprising" are to be interpreted as having an open-ended meaning. That is, the terms are to be interpreted synonymously with the phrases "having at least" or "including at least". When used in the context of a method, the term "comprising" means that the method includes at least the recited steps, but may include additional steps. When used in the context of a composition, the term "comprising" means that the composition includes at least the recited features or components, but may also include additional features or components.

The terms "consists essentially of" or "consisting essentially of" have a partially closed meaning, that is, they do not permit inclusion of steps or features or components which would substantially change the essential characteristics of a method or composition; for example, steps or features or components which would significantly interfere with the desired properties of the compounds or compositions described herein, i.e., the method or composition is limited to the specified steps or materials and those which do not materially affect the basic and novel characteristics of the method or composition.

The terms "consists of" and "consists" are closed terminology and allow only for the inclusion of the recited steps or features or components.

As used herein, the singular forms "a," "an" and "the" specifically also encompass the plural forms of the terms to which they refer, unless the content clearly dictates otherwise.

The term "about" is used herein to mean approximately, in the region of, roughly, or around. When the term "about" is used in conjunction with a numerical range, it modifies that range by extending the boundaries above and below the numerical values set forth. In general, the term "about" or "approximately" is used herein to modify a numerical value above and below the stated value by a variance of 20%.

The term "dissolved" or "substantially dissolved" is used herein to mean the solubilization of a solid in a solution. It can be considered that a solid is "dissolved" or "substantially dissolved" in a solution when the resulting solution is clear or substantially clear.

The term "clear" is used herein to mean a translucent or a subtranslucent solution. Thus, a "clear" solution has a turbidity measured according to ISO standards of ≤100 Nephelometric Turbidity Units (NTUs), preferably ≤50 NTUs.

The term "substantially clear" is used herein to mean a translucent or a subtranslucent solution. Thus, a "substantially clear" solution has a turbidity measured according to ISO standards of 100 Nephelometric Turbidity Units (NTUs).

As used herein, the term "cloudy" or "substantially cloudy" or refers to a solution having a turbidity measured according to ISO standards of greater than 100 NTUs.

As used herein, the term "milky" or "substantially milky" refers to a solution having a turbidity measured according to ISO standards of greater than 100 NTUs, preferably greater than 200 NTUs.

As used herein, the recitation of a numerical range for a variable is intended to convey that the variable can be equal to any values within that range. Thus, for a variable which is inherently discrete, the variable can be equal to any integer value of the numerical range, including the end-points of the range. Similarly, for a variable which is inherently continuous, the variable can be equal to any real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value for variables which are inherently continuous.

In the specification and claims, the singular forms include plural referents unless the context clearly dictates otherwise.

As used herein, unless specifically indicated otherwise, the word "or" is used in the "inclusive" sense of "and/or" and not the "exclusive" sense of "either/or."

Technical and scientific terms used herein have the meaning commonly understood by one of skill in the art to which the present description pertains, unless otherwise defined. Reference is made herein to various methodologies and materials known to those of skill in the art. Standard reference works setting forth the general principles of pharmacology and pharmaceutics include Goodman and Gilman's *The Pharmacological Basis of Therapeutics*, 10$^{th}$ Ed., McGraw Hill Companies Inc., New York (2001) and *Remington, The Science and Practice of Pharmacy*, 22$^{nd}$ Ed., Philadelphia (2013).

As used herein the term "% by weight of a compound X based on the volume of the composition", also abbreviated as "% w/v", corresponds to the amount of compound X in grams that is introduced in 100 mL of the composition.

As used herein the term "microparticle" refers to a particle having a diameter $D_{50}$ of 1 μm or greater to about 200 μm. The term "nanoparticle" refers to a particle having a diameter $D_{50}$ of less than 1 μm.

In exemplary embodiments, the diameter, which can be $D_{50}$, is 1 μm or greater to about 200 μm; and the term "nanoparticle" refers to a particle having a $D_{50}$ of less than about 1 μm.

As used herein an "ocular condition" is a disease, ailment or other condition which affects or involves the eye, one of the parts or regions of the eye, or the surrounding tissues such as the lacrimal glands. Broadly speaking, the eye includes the eyeball and the tissues and fluids which constitute the eyeball, the periocular muscles (such as the oblique and rectus muscles), the portion of the optic nerve which is within or adjacent to the eyeball and surrounding tissues such as the lacrimal glands and the eye lids.

As used herein an "anterior ocular condition" is a disease, ailment or condition which affects or which involves an anterior (i.e. front of the eye) ocular region or site, such as a periocular muscle, an eye lid, lacrimal gland or an eye ball tissue or fluid which is located anterior to the posterior wall of the lens capsule or ciliary muscles.

Thus, an anterior ocular condition primarily affects or involves one or more of the following: the conjunctiva, the cornea, the anterior chamber, the iris, the lens, or the lens capsule, and blood vessels and nerves which vascularize or innervate an anterior ocular region or site. An anterior ocular condition is also considered herein as extending to the lacrimal apparatus. In particular, the lacrimal glands which secrete tears, and their excretory ducts which convey tear fluid to the surface of the eye.

Moreover, an anterior ocular condition affects or involves the posterior chamber, which is behind the retina but in front of the posterior wall of the lens capsule.

A "posterior ocular condition" is a disease, ailment or condition which primarily affects or involves a posterior ocular region or site such as the choroid or sclera (in a position posterior to a plane through the posterior wall of the lens capsule), vitreous, vitreous chamber, retina, optic nerve (i.e. the optic disc), and blood vessels and nerves which vascularize or innervate a posterior ocular region or site.

Thus, a posterior ocular condition can include a disease, ailment or condition such as, for example, macular degeneration (such as non-exudative age-related macular degeneration and exudative age-related macular degeneration); choroidal neovascularization; acute macular neuroretinopathy; macular edema (such as cystoid macular edema and diabetic macular edema); Behcet's disease, retinal disorders, diabetic retinopathy (including proliferative diabetic retinopathy); retinal arterial occlusive disease; central retinal vein occlusion; uveitic retinal disease; retinal detachment; ocular trauma which affects a posterior ocular site or location; a posterior ocular condition caused by or influenced by an ocular laser treatment; posterior ocular conditions caused by or influenced by a photodynamic therapy; photocoagulation; radiation retinopathy; epiretinal membrane disorders; branch retinal vein occlusion; anterior ischemic optic neuropathy; non-retinopathy diabetic retinal dysfunction, retinitis pigmentosa and glaucoma. Glaucoma can be considered a posterior ocular condition because the therapeutic goal is to prevent the loss of or reduce the occurrence of loss of vision due to damage to or loss of retinal cells or optic nerve cells (i.e. neuroprotection).

An anterior ocular condition includes a disease, ailment or condition such as, for example, aphakia; pseudophakia; astigmatism; blepharospasm; cataract; conjunctival diseases; conjunctivitis; corneal diseases; corneal ulcer; dry eye syndromes; eyelid diseases; lacrimal apparatus diseases; lacrimal duct obstruction; myopia; presbyopia; pupil disorders; refractive disorders and strabismus. Glaucoma can also be considered to be an anterior ocular condition because a clinical goal of glaucoma treatment can be to reduce a hypertension of aqueous fluid in the anterior chamber of the eye (i.e. reduce intraocular pressure).

The present description is concerned with and directed to ophthalmic compositions for topical drug delivery to the eye(s) and to methods for the treatment of an ocular condition, such as an anterior ocular condition or a posterior ocular condition or an ocular condition which can be characterized as both an anterior ocular condition and a posterior ocular condition.

Solid Complex of Cyclodextrin and Active Pharmaceutical Ingredient

The composition of the disclosure comprises a solid complex comprising an active pharmaceutical ingredient and a cyclodextrin. The complex comprising an active pharmaceutical ingredient and a cyclodextrin may be referred to as an "active pharmaceutical ingredient/cyclodextrin complex" or a "drug/cyclodextrin complex". When the active pharmaceutical ingredient is dexamethasone and the cyclodextrin is γ-cyclodextrin, the complex comprising dexamethasone and γ-cyclodextrin may be referred to as a "dexamethasone/γ-cyclodextrin complex".

The solid complex of the composition of the disclosure may be a complex aggregate. The complex aggregate may correspond to an aggregate of a plurality of complexes, in particular a plurality of inclusion complexes comprising an active pharmaceutical ingredient and a cyclodextrin.

According to one embodiment, the ophthalmic composition of the disclosure is a microsuspension. The term "microsuspension" is intended to mean a composition comprising solid complex microparticles suspended in a liquid phase.

In particular, the ophthalmic composition of the disclosure comprises a solid complex that has a diameter $D_{50}$ of less than about 100 μm, in particular about 1 μm to about 100 μm. In one embodiment, the diameter $D_{50}$ may be in the range of about 1 μm to about 25 μm, in particular about 1 μm to about 20 μm, more particularly about 1 μm to about 10 μm, even more particularly about 2 μm to about 10 μm, more particularly still about 2 μm to about 5 μm or about 3 μm to about 8 μm. The diameter $D_{50}$ may be measured according to the test method described herein.

European Pharmacopoeia (January 2008:1163) teaches that eye drops in the form of a suspension should comply with the following: for each 10 µg of solid active substance, not more than about 20 particles have a maximum dimension greater than about 25 µm, and not more than about 2 of these particles have a maximum dimension greater than about 50 µm. None of the particles can have a maximum dimension greater than about 90 µm. The compositions of the disclosure are in conformity with the requirements of European Pharmacopoeia (January 2008:1163).

In general, it is recommended that particle sizes in aqueous eye drop suspensions are kept to a minimum, preferable below about 10 µm, to prevent eye irritation. Furthermore, the sedimentation rate in aqueous suspensions is proportional to the particle diameter, the sedimentation rate of large particles is faster than that of small particles assuming all other factors remaining constant.

Cyclodextrin

The composition of the disclosure comprises a cyclodextrin. The composition of the disclosure may comprise a mixture of cyclodextrins.

Cyclodextrins, which are also known as cycloamyloses, are produced from the enzymatic conversion of starch. They have a cyclic structure that is hydrophobic on the inside and hydrophilic on the outside. Because of the amphiphilic nature of the ring, cyclodextrins have been known to enhance the solubility and bioavailability of hydrophobic compounds.

As shown in FIG. 1, cyclodextrins are cyclic oligosaccharides containing 6 (α-cyclodextrin), 7 (β-cyclodextrin), and 8 (γ-cyclodextrin) glucopyranose monomers linked via α-1,4-glycoside bonds. α-Cyclodextrin, β-cyclodextrin and γ-cyclodextrin are natural products formed by microbial degradation of starch. The outer surface of the doughnut shaped cyclodextrin molecules is hydrophilic, bearing numerous hydroxyl groups, but their central cavity is somewhat lipophilic (Kurkov, S. V., Loftsson, T., 2013. Cyclodextrins. Int J Pharm 453, 167-180; Loftsson, T., Brewster, M. E., 1996. Pharmaceutical applications of cyclodextrins. 1. Drug solubilization and stabilization. Journal of Pharmaceutical Sciences 85, 1017-1025). In addition to the three natural cyclodextrins numerous water-soluble cyclodextrin derivatives have been synthesized and tested as drug carriers, including cyclodextrin polymers (Stella, V. J., He, Q., 2008. Cyclodextrins. Tox. Pathol. 36, 30-42).

Cyclodextrins enhance the solubility and bioavailability of hydrophobic compounds. In aqueous solutions, cyclodextrins form inclusion complexes with many drugs by taking up a drug molecule, or more frequently some lipophilic moiety of the molecule, into the central cavity. This property has been used for drug formulation and drug delivery purposes. Formation of drug/cyclodextrin inclusion complexes, their effect on the physicochemical properties of drugs, their effect on the ability of drugs to permeate biomembranes and the usage of cyclodextrins in pharmaceutical products have been reviewed (Loftsson, T., Brewster, M. E., 2010. Pharmaceutical applications of cyclodextrins: basic science and product development. Journal of Pharmacy and Pharmacology 62, 1607-1621; Loftsson, T., Brewster, M. E., 2011. Pharmaceutical applications of cyclodextrins: effects on drug permeation through biological membranes." J. Pharm. Pharmacol. 63, 1119-1135; Loftsson, T., Järvinen, T., 1999. Cyclodextrins in ophthalmic drug delivery. Advanced Drug Delivery Reviews 36, 59-79).

Figure 2:
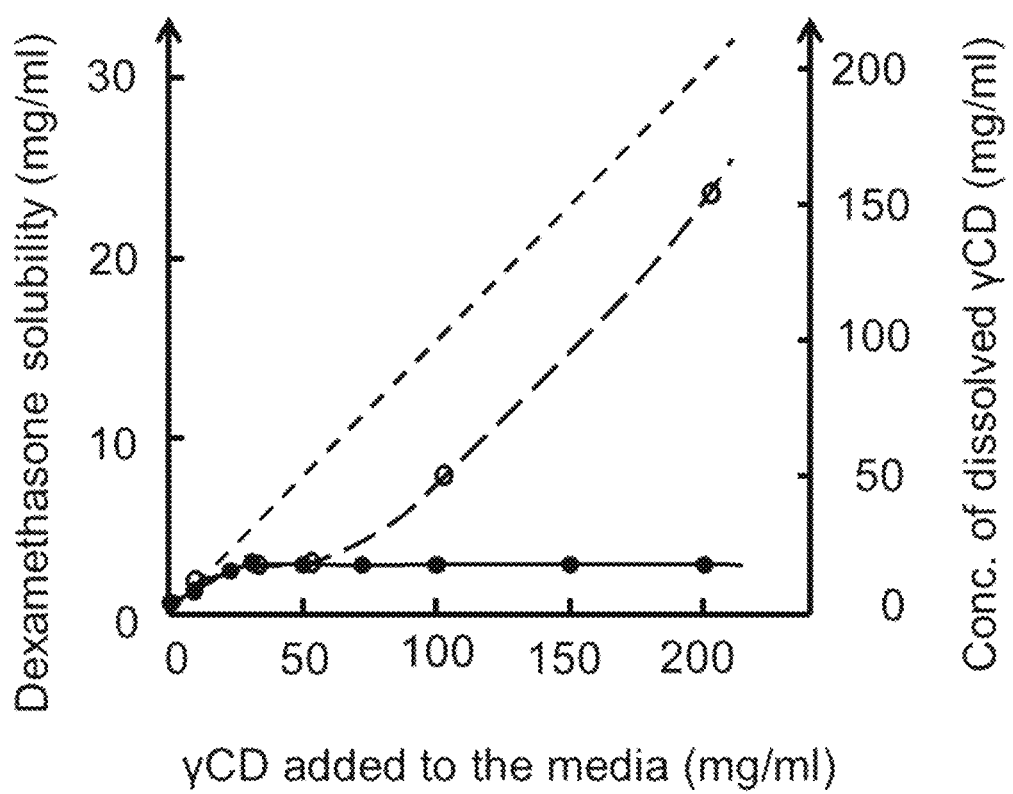
FIG. 2 depicts the effect of self-aggregation of γ-cyclodextrin on active pharmaceutical ingredient (dexamethasone) solubilization. Phase-solubility profiles of dexamethasone and the natural γ-cyclodextrin (γCD) in aqueous eye drops. The solid curve is the solubility of the active pharmaceutical ingredient (●), the broken curve is the solubility of γCD (○), and the straight line is the theoretical amount of dissolved γCD in the aqueous eye drop medium. Excess amount of dexamethasone was added to a solution containing 0 to 20% (w/v) γCD in an ophthalmically acceptable medium containing benzalkonium chloride (0.02% w/v), sodium edetate (0.1% w/v) and sufficient sodium chloride to obtain isotonic solution.

Cyclodextrins and drug/cyclodextrin complexes are able to self-assemble in aqueous solutions to form nano and micro-sized aggregates and micellar-like structures that are also able to solubilize poorly soluble active pharmaceutical ingredients through non-inclusion complexation and micellar-like solubilization (Messner, M., Kurkov, S. V., Jansook, P., Loftsson, T., 2010. Self-assembled cyclodextrin aggregates and nanoparticles. Int J Pharm 387, 199-208). In general, the tendency of cyclodextrins to self-assemble and form aggregates increases upon formation of drug/cyclodextrin complexes and the aggregation increases with increasing concentration of active pharmaceutical ingredient/cyclodextrin complexes. In general, hydrophilic cyclodextrin derivatives, such as 2-hydroxypropyl-β-cyclodextrin and 2-hydroxypropyl-γ-cyclodextrin, and their complexes are freely soluble in water. On the other hand, the natural α-cyclodextrin, β-cyclodextrin and γ-cyclodextrin and their complexes have limited solubility in pure water or 129.5±0.7, 18.4±0.2 and 249.2±0.2 mg/ml, respectively, at 25° C. (Sabadini E., Cosgrovea T. and do Carmo Egídio F., 2006. Solubility of cyclomaltooligosaccharides (cyclodextrins) in $H_2O$ and $D_2O$: a comparative study. Carbohydr Res 341, 270-274). It is known that their solubility increases somewhat with increasing temperature (Jozwiakowski, M. J., Connors, K. A., 1985. Aqueous solubility behavior of three cyclodextrins. Carbohydr. Res., 143, 51-59). Due to the limited solubility of their complexes, the natural cyclodextrins most often display $B_S$-type or $B_I$-type phase-solubility diagrams (Brewster M. E., Loftsson T., 2007, Cyclodextrins as pharmaceutical solubilizers. Adv. Drug Deliv. Rev., 59, 645-666). It has been observed that solubility of the natural cyclodextrins can decrease below their solubility in pure water upon formation of active pharmaceutical ingredient/cyclodextrin complexes (FIG. 2) (Jansook, P., Moya-Ortega, M. D., Loftsson, T., 2010. Effect of self-aggregation of γ-cyclodextrin on drug solubilization. Journal of Inclusion Phenomena and Macrocyclic Chemistry 68, 229-236). The low concentration of dissolved active pharmaceutical ingredient/cyclodextrin complexes hampers formation of nano- and microparticles containing active pharmaceutical ingredient/cyclodextrin complexes. Furthermore, other excipients, such as water-soluble polymers used to stabilize nano- and microsuspensions, can form complexes with cyclodextrins and, thus, hamper formation of active pharmaceutical ingredient/cyclodextrin complexes even further.

Previously, Applicants have described preparation and testing of cyclodextrin-based eye drops containing dexamethasone (Johannesson, G., Moya-Ortega, M. D., Asgrimsdottir, G. M., Lund, S. H., Thorsteinsdottir, M., Loftsson, T., Stefansson, E., 2014. Kinetics of γ-cyclodextrin nanoparticle suspension eye drops in tear fluid. Acta Ophthalmologica 92, 550-556; Thorsteinn Loftsson and Einar Stefansson, Cyclodextrin nanotechnology for ophthalmic drug delivery, U.S. Pat. No. 7,893,040 (Feb. 22, 2011); Thorsteinn Loftsson and Einar Stefansson, Cyclodextrin nanotechnology for ophthalmic drug delivery, U.S. Pat. No. 8,633,172 (Jan. 21, 2014); Thorsteinn Loftsson and Einar Stefansson, Cyclodextrin nanotechnology for ophthalmic drug delivery U.S. Pat. No. 8,999,953 (Apr. 7, 2015)), dorzolamide (Johannesson, G., Moya-Ortega, M. D., Asgrimsdottir, G. M., Lund, S. H., Thorsteinsdottir, M., Loftsson, T., Stefansson, E., 2014. Kinetics of γ-cyclodextrin nanoparticle suspension eye drops in tear fluid. Acta Ophthalmologica 92, 550-556; Gudmundsdottir, B. S., Petursdottir, D., Asgrimsdottir, G. M., Gottfredsdottir, M. S., Hardarson, S. H., Johannesson, G., Kurkov, S. V., Jansook, P., Loftsson, T., Stefansson, E., 2014. γ-Cyclodextrin nanoparticle eye drops with dorzolamide: effect on intraocular pressure in man. J. Ocul. Pharmacol. Ther. 30, 35-41), irbesartan (Muankaew, C., Jansook, P., Stefansson, E., Loftsson, T., 2014. Effect of γ-cyclodextrin on solubilization and complexation of irbesartan: influence of pH and excipients. Int J Pharm 474, 80-90), telmisartan (C. Muankaew, P. Jansook, H. H. Sigurðsson, T. Loftsson, 2016, Cyclodextrin-based telmisartan ophthalmic suspension: Formulation development for water-insoluble drugs. Int. J. Pharm. 507, 21-31) and cyclosporin A (S. Jóhannsdáttir, P. Jansook, E. Stefánsson, T. Loftsson, 2015, Development of a cyclodextrin-based aqueous cyclosporin A eye drop formulation. Int. J. Pharm. 493(1-2), 86-95) in cyclodextrin nanoparticles. The studies show that the nanoparticles increase the drug contact time with the ocular surface and the ocular bioavailability of the drugs. The active pharmaceutical ingredient/cyclodextrin nano- and microparticles are not only retained on the eye surface but also enhance drug solubility in the aqueous tear fluid. Nano- and microparticles composed of active pharmaceutical ingredient/γ-cyclodextrin complexes have been shown to be especially effective drug carriers for topical delivery of active pharmaceutical ingredient into the eye.

There are two approaches for preparation of nano- and microparticles and the fabrication of nano and micro structures, the top-down approach and the bottom-up approach. Top-down approach for preparation of active pharmaceutical ingredient/cyclodextrin nanoparticles and microparticles typically involves milling of solid active pharmaceutical ingredient/cyclodextrin complexes to generate nanoparticles and microparticles of desired diameter. The top-down approach can introduce surface defects and contaminations. Bottom-up approach for preparation of active pharmaceutical ingredient/cyclodextrin nanoparticles implies assembling of single molecules or single active pharmaceutical ingredient/cyclodextrin complexes into microparticles of desired diameter. The bottom-up approach frequently leads to microparticle structures with less defects and more homogeneous chemical composition.

Applicants have surprisingly discovered a bottom-up preparation of drug/cyclodextrin nanoparticles that can be accomplished with or without presence of stabilizing polymers. According to the claimed method, a drug and cyclodextrin are suspended in an aqueous medium, such as aqueous eye drop medium, and heated. At a high temperature, the active compounds as well as cyclodextrin and other pharmaceutical excipients are fully or about fully dissolved in the aqueous media and the concentration of drug/cyclodextrin complexes and excipient/cyclodextrin complexes is much lower than at ambient temperature. Then the hot solution is cooled at predetermined rate to promote formation of particles composed of drug/cyclodextrin complexes with diameter less than about 100 μm. The diameter of the particles can also be controlled by the heating and cooling cycle and by presence of stabilizing polymers in the aqueous medium. To prevent or substantially inhibit or reduce drug and/or excipient degradation, excessive heating of the medium is avoided followed by relatively rapid cooling to room temperature.

Under the controlled heating/cooling conditions, the aqueous solution comprising cyclodextrin is heated at a temperature and duration of time to limit the formation of a degradation product, or sedimentation. The initial aqueous solution optionally further comprises an active agent drug and/or a stabilizing polymer. During the heating cycle, the initial milky white cyclodextrin solution is converted into a clear solution. Heating is accomplished by any method or means known to those having ordinary skill in the art. In preferred embodiments, the heating is accomplished with an autoclave. For example, the autoclave can undergo about a 20 to about 30 minute cycle at a temperature of from about 90° C. to about 120° C.

In an exemplary embodiment, under the controlled heating/cooling conditions, the aqueous solution comprising cyclodextrin is heated at a temperature and duration of time to limit the formation of a degradation product, or sedimentation. The initial aqueous solution optionally further comprises an active pharmaceutical ingredient and/or a stabilizing polymer. During the heating cycle, the initial milky white cyclodextrin solution is converted into a clear solution. Heating is accomplished by any method or means known to those having ordinary skill in the art. In preferred embodiments, the heating is accomplished with an autoclave or jacketed reactors with steam. For example, the autoclave can undergo about a 10 to about 30 minute cycle at a temperature of about 121° C.

The heated solution is then cooled at a sufficient rate to produce a drug/cyclodextrin complex having a diameter of less than about 100 μm. Upon cooling, the drug/cyclodextrin complex precipitates to form the desired microsuspension. The microsuspension comprises about 70% to about 99% of the drug in microparticles and about 1% to about 30% of the drug in nanoparticles the eye drop vehicle. The microparticles have an average diameter of about 1 μm to about 100 μm. It is possible for the average diameter of microparticles to be in the range of about 1 μm to about 20 μm, about 1 μm to about 25 μm, about 1 μm to about 10 μm, or about 2 μm to about 5 μm. In an exemplary embodiment, the microsuspension comprises about 80% of the drug to be in microparticles having an average diameter of about 1 μm to about 10 μm, and about 20% of the drug to be in nanoparticles.

In one embodiment, the heated solution is then cooled at a sufficient rate to produce drug/cyclodextrin complex aggregates having a diameter of less than about 100 μm. Upon cooling, the drug/cyclodextrin complex precipitates to form the desired microsuspension. The microsuspension comprises about 40% to about 99% of the drug in microparticles and about 1% to about 60% of the drug in nanoparticles or water-soluble drug/cyclodextrin complexes. The microparticles have an average diameter of about 1 μm to about 100 μm. It is possible for the average diameter of microparticles to be in the range of about 1 μm to about 20 μm, about 1 μm to about 25 μm, about 1 μm to about 10 μm, or about 2 μm to about 5 μm. In an exemplary embodiment, the microsuspension comprises about 80% of the drug to be in microparticles having an average diameter of about 1 μm to about 10 μm, and about 20% of the drug to be in nanoparticles.

The microsuspensions prepared according to the claimed procedure have about a 10-fold to 100-fold increase in dissolved active agent drug concentration when compared to microsuspensions prepared according to known methods in the form of water-soluble nanoparticles, individual drug/cyclodextrin complexes and dissolved drug molecules. For example, known dexamethasone compositions comprise a dexamethasone concentration of about 1 mg/mL where only 0.1 mg/mL is in solution. However, a dexamethasone/cyclodextrin composition prepared according to the claimed method can comprise a dexamethasone concentration of about 15 mg/mL where about 4 mg/mL is in solution.

In a preferred embodiment, the cyclodextrin is α-cyclodextrin, β-cyclodextrin, γ-cyclodextrin, or combinations thereof.

In a particularly preferred embodiment, the cyclodextrin is γ-cyclodextrin. Indeed, γ-cyclodextrin has a higher solubility in water compared to that of α-cyclodextrin and β-cyclodextrin. Moreover, γ-cyclodextrin is prone to hydrolysis into glucose and maltose subunits by α-amylase in the tear fluid and the gastrointestinal tract.

The amount of cyclodextrin in the ophthalmic composition of the disclosure may be from 1 to 25%, in particular 5 to 20%, more particularly 10 to 18%, even more particularly 12 to 16%, by weight, of cyclodextrin based on the volume of the composition.

In addition to the cyclodextrin, the ophthalmic composition of the disclosure may further comprise a water-soluble cyclodextrin derivative selected from the group consisting of 2-hydroxypropyl-α-cyclodextrin, 2-hydroxypropyl-β-cyclodextrin, 2-hydroxypropyl-γ-cyclodextrin, sulfobutyl ether α-cyclodextrin, sulfobutyl ether β-cyclodextrin, sulfobutyl ether γ-cyclodextrin, methylated α-cyclodextrin, methylated β-cyclodextrin, methylated γ-cyclodextrin, and combinations thereof. The water-soluble cyclodextrin derivative may especially be used to further enhance the solubility of the active pharmaceutical ingredient, i.e. the amount of active pharmaceutical ingredient that is dissolved in the composition.

Active Pharmaceutical Ingredient

The composition of the disclosure comprises an active pharmaceutical ingredient.

The active pharmaceutical ingredient may be referred to as a "drug". In the context of the disclosure, the active pharmaceutical ingredient is an ophthalmic drug, i.e. a compound that exhibits a therapeutic effect when administered in a sufficient amount to a patient suffering from an ocular condition.

In particular, the ophthalmic composition may comprise an active pharmaceutical ingredient selected from the group consisting of a steroid such as dexamethasone, difluprednate, estradiol, fluocinolone, fluorometholone, hydrocortisone, loteprednol etabonate, prednisolone, triamcinolone, and rimexolone; a kinase inhibitor such as axitinib, BMS-794833 (N-(4-((2-amino-3-chloropyridin-4-yl)oxy)-3-fluorophenyl)-5-(4-fluorophenyl)-4-oxo-1,4-dihydropyridine-3-carboxamide), carbozantinib, cediranib, crizotinib, dasatinib, dovitinib, everolimus, lapatinib, lenvatinib, motesanib, nilotinib, nintedanib, orantinib, PD173074 (N-[2-[[4-(Diethylamino)butyl]amino]-6-(3,5-dimethoxyphenyl)pyrido[2,3-d]pyrimidin-7-yl]-N'-(1,1-dimethylethyl)urea), pazopanib, regorafenib, ruxolitinib, sorafenib, sunitinib, temsirolimus, tofacitinib, vandetanib, vemurafenib, and ZM323881 (5-((7-Benzyloxyquinazolin-4-yl)amino)-4-fluoro-2-methylphenol); an angiotensin II receptor antagonist such as candesartan, irbesartan, losartan, olmesartan, telmisartan, and valsartan; an aldose reductase inhibitor such as 2-methylsorbinol; an immunosuppressant such as sirolimus; a carbonic anhydrase inhibitor such as acetazolamide, brinzolamide, dorzolamide, ethoxzolamide and methazolamide; an antimicrobial or an antiviral such as acyclovir, chloramphenicol, chlortetracycline, ciprofloxacin, fusidic acid, gancyclovir, norfloxacin, ofloxacin, tetracycline, and zidovudine; an antihistamine such as levocabastine; and a non-steroidal anti-inflammatory active pharmaceutical ingredient such as bromfenac, diclofenac, indomethacin and nepafenac; and combinations thereof.

The active agent drug for use in the nano- and microparticles in the exemplary embodiments can be selected from, but are not limited to, the group consisting of a steroid such as dexamethasone, difluprednate, estradiol, fluocinolone, fluorometholone, hydrocortisone, loteprednol etabonate, prednisolone, triamcinolone and rimexolone; a kinase inhibitor such as axitinib, BMS-794833 N-(4-((2-amino-3-chloropyridin-4-yl)oxy)-3-fluorophenyl)-5-(4-fluorophenyl)-4-oxo-1,4-dihydropyridine-3-carboxamide), carbozantinib, cediranib, dovitinib, lapatinib, lenvatinib, motesanib, nintedanib, orantinib, PD173074 (N-[2-[[4-(Diethylamino)butyl]amino]-6-(3,5-dimethoxyphenyl)pyrido[2,3-d]pyrimidin-7-yl]-N'-(1,1-dimethylethyl)urea), pazopanib, regorafenib, sorafenib, tofacitinib, and ZM323881 (5-((7-Benzyloxyquinazolin-4-yl)amino)-4-fluoro-2-methylphenol); an angiotensin II receptor antagonist such as candesartan, irbesartan, losartan, olmesartan, telmisartan, and valsartan; an aldose reductase inhibitors such as 2-methylsorbinol; an immunosuppressant such as sirolimus, a carbonic anhydrase inhibitor such as acetazolamide, brinzolamide, dorzolamide, ethoxzolamide and methazolamide; an antimicrobial and an antiviral such as acyclovir, chloramphenicol, chlortetracycline, ciprofloxacin, fusidic acid, gancyclovir, norfloxacin, ofloxacin, tetracycline, and zidovudine; an antihistamine such as levocabastine; and a non-steroidal anti-inflammatory drug such as bromfenac, diclofenac, indomethacin, nepafenac, or a combination thereof.

According to a preferred embodiment, the ophthalmic composition comprises an active pharmaceutical ingredient selected from the group consisting of dexamethasone, axitinib, cediranib, dovitinib, motesanib, pazopanib, regorafenib, losartan, olmesartan, dorzolamide, diclofenac, nepafenac, and combinations thereof. More preferably, the active pharmaceutical ingredient is dexamethasone.

The concentration of active pharmaceutical ingredient in the ophthalmic composition of the disclosure may be from about 0.1 mg/mL to about 100 mg/mL, in particular from about 1 mg/mL to about 100 mg/mL, in particular from about 1 mg/mL to about 50 mg/mL, more particularly from about 1 mg/mL to about 20 mg/mL, even more particularly about 5 mg/mL to about 25 mg/mL, more particularly still from about 10 mg/mL to about 20 mg/mL.

In exemplary embodiments, the active pharmaceutical ingredient (i.e. drug) is present in the initial aqueous solution at a concentration of about 1 mg/mL to about 100 mg/mL. It is further possible to obtain the desired final active pharmaceutical ingredient/cyclodextrin complex concentration with an initial active pharmaceutical ingredient concentration of about 1 mg/mL to about 50 mg/mL and about 1 mg/mL to about 20 mg/mL.

In other exemplary embodiments, the active pharmaceutical ingredient is present in the initial aqueous solution at a concentration of about 0.01 mg/mL to about 10 mg/mL.

The compositions of the disclosure may have about 10-fold to about 100-fold increase in dissolved active pharmaceutical ingredient concentration when compared to compositions prepared according to known methods.

In particular, 60 to 95% by weight, more particularly 70 to 90% by weight, of the active pharmaceutical ingredient in the composition may be in the form of a solid complex of active pharmaceutical ingredient and cyclodextrin.

Even more particularly, 5 to 40% by weight, in particular 10 to 30% by weight, of the active pharmaceutical ingredient in the composition may be in dissolved form. The dissolved form includes uncomplexed active pharmaceutical ingredient that is dissolved in the liquid phase and complexes of active pharmaceutical ingredient and cyclodextrin that are dissolved in the liquid phase as well as water-soluble nanoparticles consisting of drug/cyclodextrin complex aggregates.

Preferably, 0% to 0.5% by weight of the active pharmaceutical ingredient in the composition may be in uncomplexed solid form. As such, the composition of the disclosure may be substantially free of solid uncomplexed particles of active pharmaceutical ingredient.

In one embodiment, the microsuspension may comprise about 70% to about 99% of the active pharmaceutical ingredient in microparticles and about 1% to about 30% of the active pharmaceutical ingredient in nanoparticles. More particularly, the microsuspension may comprise about 80% of the active pharmaceutical ingredient in microparticles having a diameter of about 1 μm to about 10 μm, and about 20% of the active pharmaceutical ingredient in nanoparticles.

In another embodiment, the microsuspension may comprise about 40% to about 99% of the active pharmaceutical ingredient in microparticles and about 1% to about 60% of the active pharmaceutical ingredient in nanoparticles or water-soluble active pharmaceutical ingredient/cyclodextrin complexes. In particular, the microsuspension may comprise about 80% to about 90% of the active pharmaceutical ingredient in microparticles having a diameter of about 1 μm to about 10 μm, and about 10% to about 20% of the active pharmaceutical ingredient in nanoparticles or water-soluble active pharmaceutical ingredient/cyclodextrin complexes.

Polymer

The composition of the disclosure may further comprise a polymer.

In particular, said polymer may be a water-soluble polymer. Moreover, said polymer may be a viscosity enhancing polymer. The term "viscosity enhancing polymer" is intended to mean a polymer that increases the viscosity of a liquid. The polymer increases the viscosity of the composition of the disclosure. The increase of viscosity results is a enhanced physical stability of the composition. As such, the composition is less prone to sedimentation of the solid complex when it comprises a polymer. The polymer may thus be considered as a polymeric stabilizing agent.

In particular, the polymer may be a surface active polymer. The term "surface active polymer" is intended to mean a polymer that exhibits surfactant properties. Surface active polymers may, for example, comprise hydrophobic chains grafted to a hydrophilic backbone polymer; hydrophilic chains grafted to a hydrophobic backbone; or alternating hydrophilic and hydrophobic segments. The first two types are called graft copolymers and the third type is named block copolymer.

In one embodiment, the ophthalmic composition of the disclosure comprises a polymer selected from the group consisting of a polyoxyethylene fatty acid ester; a polyoxyethylene alkylphenyl ether; a polyoxyethylene alkyl ether; a cellulose derivative such as alkyl cellulose, hydroxyalkyl cellulose and hydroxyalkyl alkylcellulose; a carboxyvinyl polymer such as a carbomer, for example Carbopol 971 and Carbopol 974; a polyvinyl polymer; a polyvinyl alcohol; a polyvinylpyrrolidone; a copolymer of polyoxypropylene and polyoxyethylene; tyloxapol; and combinations thereof.

Examples of suitable polymers include, but are not limited to, polyethylene glycol monostearate, polyethylene glycol distearate, hydroxypropyl methylcellulose, hydroxypropylcellulose, polyvinylpyrrolidone, polyoxyethylene lauryl ether, polyoxyethylene octyldodecyl ether, polyoxyethylene stearyl ether, polyoxyethylene myristyl ether, polyoxyethylene oleyl ether, sorbitan esters, polyoxyethylene hexadecyl ether (e.g., cetomacrogol 1000), polyoxyethylene castor oil derivatives, polyoxyethylene sorbitan fatty acid esters (e.g., Tween 20 and Tween 80 (ICI Specialty Chemicals)); polyethylene glycols (e.g., Carbowax 3550 and 934 (Union Carbide)), polyoxyethylene stearates, carboxymethylcellulose calcium, carboxymethylcellulose sodium, methylcellulose, hydroxyethylcellulose, hydroxypropyl methylcellulose, cellulose, polyvinyl alcohol (PVA), poloxamers (e.g., Pluronics F68 and F108, which are block copolymers of ethylene oxide and propylene oxide); poloxamines (e.g., Tetronic 908, also known as Poloxamine 908, which is a tetrafunctional block copolymer derived from sequential addition of propylene oxide and ethylene oxide to ethylenediamine (BASF Wyandotte Corporation, Parsippany, N.J.)); Tetronic 1508 (T-1508) (BASF Wyandotte Corporation), Tritons X-200, which is an alkyl aryl polyether sulfonate (Rohm and Haas); PEG-derivatized phospholipid, PEG-derivatized cholesterol, PEG-derivatized cholesterol derivative, PEG-derivatized vitamin A, PEG-derivatized vitamin E, random copolymers of vinyl pyrrolidone and vinyl acetate, combinations thereof and the like.

Particularly preferred examples of polymers according to the disclosure are tyloxapol and a copolymer of polyoxypropylene and polyoxyethylene.

More particularly, the copolymer of polyoxypropylene and polyoxyethylene may be a triblock copolymer comprising a hydrophilic block-hydrophobic block-hydrophilic block configuration.

In one embodiment, the composition of the disclosure comprises a polymer which is a poloxamer. Poloxamers can include any type of poloxamer known in the art. Poloxamers include poloxamer 101, poloxamer 105, poloxamer 108, poloxamer 122, poloxamer 123, poloxamer 124, poloxamer 181, poloxamer 182, poloxamer 183, poloxamer 184, poloxamer 185, poloxamer 188, poloxamer 212, poloxamer 215, poloxamer 217, poloxamer 231, poloxamer 234, poloxamer 235, poloxamer 237, poloxamer 238, poloxamer 282, poloxamer 284, poloxamer 288, poloxamer 331, poloxamer 333, poloxamer 334, poloxamer 335, poloxamer 338, poloxamer 401, poloxamer 402, poloxamer 403, poloxamer 407, poloxamer 105 benzoate and poloxamer 182 dibenzoate. Poloxamers are also referred to by their trade name Pluronic such as Pluronic 10R5, Pluronic 17R2, Pluronic 17R4, Pluronic 25R2, Pluronic 25R4, Pluronic 31 R1, Pluronic F 108, Pluronic F 108, Pluronic F 108, Pluronic F 108NF, Pluronic F 127, Pluronic F 127 NF, Pluronic F 127, Pluronic F 127, Pluronic F 38, Pluronic F 38, Pluronic F 68, Pluronic F 77, Pluronic F 87, Pluronic F 88, Pluronic F 98, Pluronic L 10, Pluronic L 101, Pluronic L 121, Pluronic L 31, Pluronic L 35, Pluronic L 43, Pluronic L 44, Pluronic L 61, Pluronic L 62, Pluronic L 62 LF, Pluronic L 62D, Pluronic L 64, Pluronic L 81, Pluronic L 92, Pluronic L 44, Pluronic N 3, Pluronic P 103, Pluronic P 104, Pluronic P 105, Pluronic P 123, Pluronic P 65, Pluronic P 84, Pluronic P 85, combinations thereof and the like.

Especially useful polymers as stabilizers are poloxamers. Poloxamers can include any type of poloxamer known in the art. Poloxamers include poloxamer 101, poloxamer 105, poloxamer 108, poloxamer 122, poloxamer 123, poloxamer 124, poloxamer 181, poloxamer 182, poloxamer 183, poloxamer 184, poloxamer 185, poloxamer 188, poloxamer 212, poloxamer 215, poloxamer 217, poloxamer 231, poloxamer 234, poloxamer 235, poloxamer 237, poloxamer 238, poloxamer 282, poloxamer 284, poloxamer 288, poloxamer 331, poloxamer 333, poloxamer 334, poloxamer 335, poloxamer 338, poloxamer 401, poloxamer 402, poloxamer 403, poloxamer 407, poloxamer 105 benzoate and poloxamer 182 dibenzoate. Poloxamers are also referred to by their trade name Pluronic such as Pluronic 10R5, Pluronic 17R2, Pluronic 17R4, Pluronic 25R2, Pluronic 25R4, Pluronic 31R1, Pluronic F 108 Cast Solid Surfacta, Pluronic F 108 NF, Pluronic F 108 Pastille, Pluronic F 108NF Prill Poloxamer 338, Pluronic F 127, Pluronic F 127 NF, Pluronic F 127 NF 500 BHT Prill, Pluronic F 127 NF Prill Poloxamer 407, Pluronic F 38, Pluronic F 38 Pastille, Pluronic F 68, Pluronic F 68 Pastille, Pluronic F 68 LF Pastille, Pluronic F 68 NF, Pluronic F 68 NF Prill Poloxamer 188, Pluronic F 77, Pluronic F 77 Micropastille, Pluronic F 87, Pluronic F 87 NF, Pluronic F 87 NF Prill Poloxamer 237, Pluronic F 88, Pluronic F 88 Pastille, Pluronic F 98, Pluronic L 10, Pluronic L 101, Pluronic L 121, Pluronic L 31, Pluronic L 35, Pluronic L 43, Pluronic L 44 NF Poloxamer 124, Pluronic L 61, Pluronic L 62, Pluronic L 62 LF, Pluronic L 62D, Pluronic L 64, Pluronic L 81, Pluronic L 92, Pluronic L44 NF INH surfactant Poloxamer 124 View, Pluronic N 3, Pluronic P 103, Pluronic P 104, Pluronic P 105, Pluronic P 123 Surfactant, Pluronic P 65, Pluronic P 84, Pluronic P 85, combinations thereof and the like.

A further polymeric stabilizing agent compatible with the compositions and methods described herein is tyloxapol. In preferred embodiments, the stabilizer and co-solubilizer is tyloxapol, which is a 4-(1,1,3,3-tetramethylbutyl)phenol polymer with formaldehyde and oxirane.

The solutions and microsuspensions prepared according to Applicants' method optionally comprise further additives. For example, it is envisioned that the solution and/or the microsuspension further comprises ethylenediaminetetraacetic acid (EDTA). EDTA can be used, for example, to reduce degradation or as a stabilizer. It is also envisioned that the solution and/or microsuspension is isotonic, for example, with the addition of sodium chloride.

In an exemplary embodiment, the EDTA can be ethylenediaminetetraacetic acid disodium salt.

According to one method, the active agent drug and at least one cyclodextrin are suspended in an aqueous eye drop vehicle to provide a suspension having a milky appearance. The suspension is then heated for a sufficient time at a sufficient temperature until both the drug and cyclodextrin are dissolved in the aqueous eye drop solution, and no degradation product is formed. Once the drug and the cyclodextrin are dissolved the milky suspension turns into a substantially clear solution. The resulting solution is cooled at a rate sufficient to produce a microsuspension comprising a microparticle drug/cyclodextrin complex.

In another embodiment, an active agent drug, at least one cyclodextrin, and at least one polymer are suspended in an aqueous eye drop vehicle to provide a suspension having a milky appearance. The suspension is then heated for a sufficient time at a sufficient temperature until the drug, cyclodextrin, and the polymer are dissolved in the aqueous eye drop solution, and no degradation product is formed. Once the drug, the cyclodextrin, and the polymer are dissolved the milky suspension turns into a substantially clear solution. The resulting solution is cooled at a rate sufficient to produce a microsuspension comprising a microparticle drug/cyclodextrin/polymer complex. In this alternative embodiment, drug/cyclodextrin/polymer complex comprises a polymer coating.

In an alternative method, at least one cyclodextrin is suspended in an aqueous eye drop vehicle to provide a suspension having a milky appearance. The cyclodextrin suspension is heated for a sufficient time at a sufficient temperature until the cyclodextrin is dissolved in the aqueous eye drop solution. An active agent drug is added to the heated aqueous suspension, while stirring the solution, until the drug is dissolved in the solution. The resulting solution is cooled at a rate sufficient to produce a microsuspension comprising a microparticle drug/cyclodextrin complex.

In yet another method, cyclodextrin and at least one polymer are suspended in an aqueous eye drop vehicle to provide a suspension having a milky appearance. Once the cyclodextrin and the polymer are dissolved the milky suspension turns into a substantially clear solution. An active agent drug is added to the heated aqueous suspension, while stirring the solution, until the drug is dissolved in the solution. The resulting solution is cooled at a rate sufficient to produce a microsuspension comprising a microparticle drug/cyclodextrin/polymer complex. The resulting drug/cyclodextrin/polymer complex comprises a polymer coating.

In another method, at least one polymer and a drug is suspended in an aqueous eye drop vehicle to provide a suspension having a milky appearance. In another container, at least one cyclodextrin is suspended in water to provide a suspension having a milky appearance. Both the suspensions are heated for a sufficient time at a sufficient temperature until the cyclodextrin solution becomes transparent, the polymer/drug suspension is still a milky suspension and no (or substantially no) degradation product is being formed. The cyclodextrin solution is added to the polymer/drug phase and the mixture becomes clear as the drug dissolves and the solution is mixed for a sufficient time at the same temperature. The resulting solution is cooled at a rate sufficient to produce a microsuspension comprising a microparticle drug/cyclodextrin complex.

The polymer that may be introduced in the composition of the disclosure can exhibit a weight average molecular weight of 2,000 g/mol or higher, in particular a weight average molecular weight from 2,000 to 50,000 g/mol, more particularly 5,000 to 25,000 g/mol, even more particularly 9,000 to 15,000 g/mol.

The amount of polymer in the composition of the disclosure may be 0.5 to 5%, in particular 1 to 4%, more particularly 2 to 3%, more particularly 2.2 to 2.8%, by weight of polymer based on the volume of the composition.

When the composition comprises a polymer, the viscosity of the composition may be from 4 to 14 cP, preferably 5 to 13 cP, more preferably 6 to 12 cP.

Part of the polymer that is introduced in the composition of the disclosure may be contained in the solid complexes of active pharmaceutical ingredient and cyclodextrin. As such, some of the polymer may be taken up within the solid complex and/or part of the polymer may be coated on the surface of the solid complex. The microsuspension may thus comprise a microparticle drug/cyclodextrin/polymer complex. Said drug/cyclodextrin/polymer complex may comprise a polymer coating.

Ophthalmically Acceptable Medium

The composition of the disclosure comprises an ophthalmically acceptable medium.

The term "ophthalmically acceptable medium" is intended to mean a medium suitable for ophthalmic administration of the composition. The ophthalmically acceptable medium is preferably a liquid. The ophthalmically acceptable medium may notably comprise water. In particular, the ophthalmically acceptable medium does not comprise any other solvent than water. The ophthalmically acceptable medium may thus correspond to an aqueous eye drop vehicle.

According to a preferred embodiment the ophthalmically acceptable medium comprises water and optionally an additive selected from the group consisting of a preservative, a stabilizing agent, an electrolyte, a buffering agent, and combinations thereof.

In particular, the ophthalmically acceptable medium may comprise a preservative. A preservative may be used to limit bacterial proliferation in the composition.

Suitable examples of preservative are sodium bisulfite, sodium bisulfate, sodium thiosulfate, benzalkonium chloride, chlorobutanol, thimerosal, phenylmercuric acetate, phenylmercuric nitrate, methylparaben, phenylethyl alcohol, and combinations thereof. Preferably, the preservative is benzalkonium chloride.

The amount of preservative in the composition of the disclosure may be 0 to 1%, in particular 0.001 to 0.5%, more particularly 0.005 to 0.1%, even more particularly 0.01 to 0.04%, by weight of preservative based on the volume of the composition.

In particular, the ophthalmically acceptable medium may comprise a stabilizing agent. A stabilizing agent may be used to reduce degradation or stabilize the composition during storage.

An example of a suitable stabilizing agent is disodium edetate.

The amount of stabilizing agent in the composition of the disclosure may be 0 to 1%, in particular 0.01 to 0.5%, more particularly 0.08 to 0.2% by weight of stabilizing agent based on the volume of the composition.

In particular, the ophthalmically acceptable medium may comprise an electrolyte. An electrolyte may especially be used to make the composition isotonic.

Examples of suitable electrolytes include sodium chloride, potassium chloride, and combinations thereof. Preferably, the electrolyte is sodium chloride.

The amount of electrolyte in the composition of the disclosure may be 0 to 2%, in particular 0.1 to 1.5%, more particularly 0.5 to 1% by weight of electrolyte based on the volume of the composition.

Impurities

The composition according to the disclosure may notably exhibit a low concentration of impurities. The low amount of impurities in the composition of the disclosure results from the specific preparation process described hereinafter, in particular the specific heating and cooling steps implemented in the preparation process.

Accordingly, the composition according to the disclosure may comprise less than 2%, in particular less than 1%, more particularly less than 0.8%, by weight of impurities based on the weight of the active pharmaceutical ingredient.

The term "impurities" is intended to mean a product that was not voluntarily introduced in the composition of the disclosure but was generated in situ during manufacturing of the composition. As such the term "impurities" encompasses any product other than an active pharmaceutical ingredient, a cyclodextrin, a complex of active pharmaceutical ingredient and a cyclodextrin, a polymer, water, a preservative, a stabilizing agent, and an electrolyte as defined herein above. The impurities typically correspond to a by-product or a degradation product of the active pharmaceutical ingredient. The amount of the impurities in the composition can be determined by conventional analytical techniques including, for example liquid chromatography, mass spectrometry and/or NMR. The amount of impurities can be measured shortly after, for example less than 24 hours after, preparation of the composition or after storage of the composition, for example up to 2 years of storage of the composition, at 25° C.

Surprisingly, Applicants observed that the compositions of the disclosure containing specific active pharmaceutical ingredients were particularly prone to generating impurities when aqueous solutions or suspensions thereof were heated in the presence of cyclodextrins, for example γ-cyclodextrin, at a temperature above 120° C. However, negligible amounts of impurities were obtained when the compositions were prepared according to the method of the disclosure described hereinafter.

Accordingly, according to one embodiment, the present disclosure provides an ophthalmic composition comprising, in an ophthalmically acceptable medium, a solid complex comprising an active pharmaceutical ingredient and a cyclodextrin; wherein the composition comprises less than 2%, in particular less than 1%, more particularly less than 0.8%, by weight of impurities based on the weight of the active pharmaceutical ingredient; wherein the active pharmaceutical ingredient is selected from the group consisting of dexamethasone, axitinib, cediranib, dovitinib, motesanib, pazopanib, regorafenib, losartan, olmesartan, dorzolamide, diclofenac, nepafenac, and combinations thereof; and wherein the cyclodextrin is γ-cyclodextrin.

In particular, when the active ingredient is dexamethasone, the composition of the disclosure may comprise less than 0.5%, in particular less than 0.3%, more particularly less than 0.2%, by dexamethasone enol aldehydes (i.e. a mixture of Z and E isomers) based on the weight of dexamethasone.

Dexamethasone enol aldehydes are dehydrated dexamethasone that have the following structures:

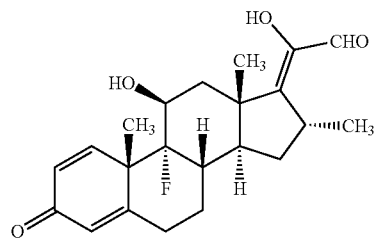

Z isomer of dexamethasone enol aldehyde

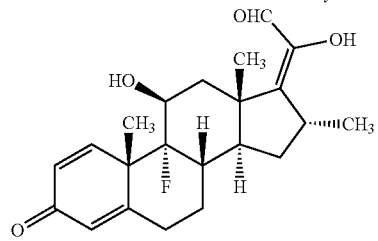

E isomer of dexamethasone enol aldehyde

Furthermore, when the active ingredient is dexamethasone, the composition of the disclosure may comprise less than 0.5%, in particular less than 0.3%, more particularly less than 0.2%, by weight of 16,17-unsaturated dexamethasone based on the weight of dexamethasone.

16,17-unsaturated dexamethasone is a dehydrated dexamethasone that has the following structure:

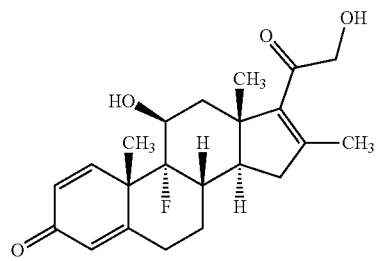

16,17-unsaturated dexamethasone

In particular, when the active ingredient is dexamethasone, the composition of the disclosure may comprise less than 0.5%, in particular less than 0.3%, more particularly less than 0.2%, by weight of dehydrated dexamethasone, i.e. dexamethasone enol aldehydes (i.e. a mixture of Z and E isomers) and 16,17-unsaturated dexamethasone, based on the weight of the dexamethasone.

It is known that dexamethasone can undergo base catalyzed and photochemical degradation in aqueous solutions (E. M. Cohen, 1973, Dexamethasone. Analytical Profiles of Drug Substances, 2, 163-197) and that the active pharmaceutical ingredient is subjected to oxidative decomposition (R. E. Conrow, G. W. Dillow, L. Bian, L. Xue, O. Papadopoulou, J. K. Baker, B. S. Scott, 2002, Corticosteroid decomposition via a mixed anhydride. J. Org. Chem. 67, 6835-6836). The dexamethasone monograph in the European Pharmacopoeia (January 2014:0388) lists 11 impurities and degradation products and describes a method for their detection. The British Pharmacopeia (2015, version 19.0) has a monograph on dexamethasone eye drop suspension and lists 5 degradation impurities and products and a method for their detection. For maximum chemical stability in aqueous solutions the pH of the dexamethasone eye drop suspensions should be kept between about 5.0 and about 6.0. The major degradation product formed during preparation of the aqueous dexamethasone eye drop suspension containing cyclodextrin and sterilization of the eye drops in an autoclave is believed to comprise a 16,17-unsaturated dexamethasone and a mixture of E and Z isomers of dexamethasone enol aldehydes, formed by Mattox rearrangement through the dehydration of dexamethasone (B. Chen, M. Li, M. Lin, G. Tumambac, A. Rustum, 2009, A comparative study of enol aldehyde formation from betamethasone, dexamethasone, beclomethasone and related compound under acidic and alkaline conditions. Steroids, 74, 30-41). Due to steric hindrance in the case of dexamethasone the main product is believed to be the dexamethasone enol aldehyde Z isomer. This degradation product is not listed in the pharmacopoeias. Previously, 16,17-unsaturated dexamethasone has been detected in parenteral dexamethasone solutions that were heated to about 75° C. for about 10 days (M. Spangler, E. Mularz, 2001, A validated, stability-indicating method for the assay of dexamethasone in drug substance and drug product analyses, and the assay of preservatives in drug product. Chromatographia, 54, 329-334), which is also a dehydrated degradation product of dexamethasone and since the authors did not analyze the product the authors likely detected the enol aldehydes. Previously a Japanese group described the two enol aldehydes and the 16-17 unsaturated degradation products of betamethasone, both by acidic catalysis (T. Hidaka, S. Huruumi, S. Tamaki, M. Shiraishi, H. Minato, 1980, Studies on betamethasone: behavior of betamethasone in acid or alkaline medium, photolysis and oxidation. Yakugaku Zasshi, 100, 72-80). The apparent activation energy for the rate of dexamethasone degradation to form 16,17-unsaturated dexamethasone and dexamethasone enol aldehydes in aqueous γ-cyclodextrin solution is unusually high and, thus, these degradation products are essentially not formed at ambient temperature. The presence of cyclodextrin in the aqueous eye drops appears to promote dehydration of dexamethasone during autoclaving to form 16,17-unsaturated dexamethasone and a mixture of E and Z isomers of dexamethasone enol aldehydes.

In aqueous solutions, diclofenac is relatively stable at room temperature when protected from light and oxygen (R. Chadaha, N. Kashid, D. V. S. Jain, 2003, Kinetics of degradation of diclofenac sodium in aqueous solution determined by a calorimetric method. Pharmazie, 58, 631-635). Although β-cyclodextrin has been shown to stabilize diclofenac in aqueous solutions at about pH 7 we have observed that γ-cyclodextrin can accelerate the degradation during autoclaving causing intense coloring of aqueous diclofenac solutions.

Here, Applicants have surprisingly discovered that the claimed method provides solutions and microsuspensions comprising active pharmaceutical ingredient/cyclodextrin complexes that are stable in the aqueous solution. For example, the claimed method provides a dexamethasone/γ-cyclodextrin eye drop solution in which very low amounts of 16,17-unsaturated dexamethasone and dexamethasone enol aldehydes are formed. Moreover, this disclosure provides a diclofenac/γ-cyclodextrin solution in which no degradation product or sedimentation is observed for at least about 12 months. These aqueous γ-cyclodextrin containing eye drops also have the benefit of having 10 to 100-fold increase, in the case of dexamethasone about a 30-fold increase, in the concentration of dissolved active pharmaceutical ingredient, and have the desired particle size to achieve maximum drug diffusion.

Dexamethasone Composition

According to a particularly preferred embodiment, the present disclosure provides an ophthalmic dexamethasone composition comprising, in an ophthalmically acceptable medium, a solid complex comprising dexamethasone and γ-cyclodextrin.

In one embodiment, the ophthalmic dexamethasone composition of the disclosure comprises less than 0.5%, in particular less than 0.3%, more particularly less than 0.2%, by weight of 16,17-unsaturated dexamethasone and dexamethasone enol aldehydes based on the weight of dexamethasone.

In another embodiment, the ophthalmic dexamethasone composition of the disclosure comprises a polymer as defined herein above. The viscosity of said ophthalmic dexamethasone composition may be from 4 to 14 cP, preferably 5 to 13 cP, more preferably 6 to 12 cP.

In yet another embodiment, the ophthalmic dexamethasone composition of the disclosure comprises less than 0.5%, in particular less than 0.3%, more particularly less than 0.2%, by weight of 16,17-unsaturated dexamethasone and dexamethasone enol aldehydes based on the weight of dexamethasone; the ophthalmic dexamethasone composition of the disclosure comprises a polymer; and the viscosity of the ophthalmic dexamethasone composition is from 4 to 14 cP, preferably 5 to 13 cP, more preferably 6 to 12 cP.

The concentration of dexamethasone in the ophthalmic composition of the disclosure may be from 10 mg/mL to 20 mg/mL. As such, the amount of dexamethasone in the composition of the disclosure is much higher than known dexamethasone compositions which comprise a dexamethasone concentration of about 1 mg/mL where about 0.1 mg/mL is in solution. In particular, the concentration of dexamethasone in the ophthalmic composition of the disclosure may be of about 15 mg/mL where about 4 mg/mL is in solution.

In particular, 60 to 95% by weight, more particularly 70 to 90% by weight, of the dexamethasone in the composition may be in the form of a solid complex of dexamethasone and γ-cyclodextrin.

More particularly, 5 to 40% by weight, in particular 10 to 30% by weight, of the dexamethasone in the composition may be in dissolved form. The dissolved form includes uncomplexed dexamethasone that is dissolved in the liquid phase, complexes of dexamethasone and cyclodextrin that are dissolved in the liquid phase and water-soluble nanoparticles consisting of dexamethasone/cyclodextrin complex aggregates.

Preferably, 0% to 0.5% by weight of the dexamethasone in the composition may be in uncomplexed solid form. As such, the composition of the disclosure may be substantially free of solid uncomplexed particles of dexamethasone.

In one embodiment, the microsuspension may comprise about 70% to about 99% of the dexamethasone in microparticles and about 1% to about 30% of the dexamethasone in nanoparticles. More particularly, the microsuspension may comprise about 80% of the dexamethasone in microparticles having a diameter of about 1 µm to about 10 µm, and about 20% of the dexamethasone in nanoparticles.

In another embodiment, the microsuspension may comprise 40% to 99% of the dexamethasone in microparticles and about 1% to about 60% of the dexamethasone in nanoparticles or water-soluble dexamethasone/γ-cyclodextrin complexes. In particular, the microsuspension may comprise about 80 to 90% of the dexamethasone in microparticles having a diameter of about 1 µm to about 10 µm, and about 10 to 20% of the dexamethasone in nanoparticles or water-soluble dexamethasone/γ-cyclodextrin complexes.

The amount of γ-cyclodextrin in the ophthalmic dexamethasone composition may be from 1 to 25%, in particular 5 to 20%, more particularly 10 to 18%, even more particularly 12 to 16%, by weight of γ-cyclodextrin based on the volume of the composition.

In addition to the γ-cyclodextrin, the ophthalmic composition of the disclosure may further comprise α-cyclodextrin, γ-cyclodextrin and/or a water-soluble cyclodextrin derivative as defined above.

The dexamethasone ophthalmic composition of the disclosure comprises an ophthalmically acceptable medium as defined above.

According to a preferred embodiment, the ophthalmically acceptable medium comprises water and optionally an additive selected from the group consisting of a preservative, a stabilizing agent, an electrolyte, a buffering agent, and combinations thereof, as defined above.

In a particularly preferred embodiment, the ophthalmic dexamethasone composition comprises:

1 to 2% of dexamethasone, for example 1.5% of dexamethasone;

12 to 16% of γ-cyclodextrin, for example 14% of γ-cyclodextrin;

2.2 to 2.8% of polymer, for example 2.5% of poloxamer;

0 to 0.2% of stabilizing agent, for example 0.1% of disodium edetate;

0 to 1% of electrolyte, for example 0.57% of sodium chloride; and water;

wherein the % are % by weight based on the volume of the composition.

Method of Preparing Ophthalmic Compositions According to the Disclosure

The compositions of the disclosure can be obtainable by or obtained by the following methods. All of the embodiments, preferred recitations and particular examples cited in the previous sections equally apply to the methods of the disclosure and the compositions obtained with the methods of the disclosure.

In a first embodiment, the method of preparing an ophthalmic composition comprises the steps of:
a) suspending an active pharmaceutical ingredient and a cyclodextrin in an ophthalmically acceptable medium to form a suspension;
b) heating the suspension at a temperature T1 lower than 120° C. for a time t until the active pharmaceutical ingredient and the cyclodextrin are substantially dissolved in the ophthalmically acceptable medium; and
c) cooling the resulting solution to a temperature T2 to obtain an ophthalmic composition comprising a solid complex of an active pharmaceutical ingredient and a cyclodextrin.

In the method of the first embodiment, the active pharmaceutical ingredient and the cyclodextrin may be suspended in an ophthalmically acceptable medium to provide a suspension having a milky appearance. The suspension may then be heated for a sufficient time at a sufficient temperature until both the active pharmaceutical ingredient and cyclodextrin are dissolved in the ophthalmically acceptable medium, and no degradation product is formed. Once the active pharmaceutical ingredient and the cyclodextrin are dissolved, the milky suspension may turn into a substantially clear solution. The resulting solution may then be cooled at a rate sufficient to produce a microsuspension comprising a solid active pharmaceutical ingredient/cyclodextrin complex.

In a second embodiment, the method of preparing an ophthalmic composition comprises the steps of:
a) suspending a cyclodextrin in an ophthalmically acceptable medium to form a suspension;
b) heating the suspension until the cyclodextrin is substantially dissolved in the ophthalmically acceptable medium;
c) adding an active pharmaceutical ingredient in solid form in the solution of step b) at a temperature T1 lower than 120° C. and heating the mixture at a temperature T1 lower than 120° C. for a time t until the active pharmaceutical ingredient is substantially dissolved in the ophthalmically acceptable medium; and
d) cooling the resulting solution to a temperature T2 to obtain an ophthalmic composition comprising a solid complex of an active pharmaceutical ingredient and a cyclodextrin.

In the method of the second embodiment, a cyclodextrin may be suspended in an ophthalmically acceptable medium to provide a suspension having a milky appearance. The cyclodextrin suspension may be heated for a sufficient time at a sufficient temperature until the cyclodextrin is dissolved in the ophthalmically acceptable medium. An active pharmaceutical ingredient may be added in solid form to the heated aqueous solution, while stirring the solution. The heating may be carried out for a sufficient time at a sufficient temperature until the active pharmaceutical ingredient is dissolved in the ophthalmically acceptable medium, and no degradation product is formed. The resulting solution may be cooled at a rate sufficient to produce a microsuspension comprising a solid active pharmaceutical ingredient/cyclodextrin complex.

In a third embodiment, the method of preparing an ophthalmic composition comprises the steps of:
a) suspending an active pharmaceutical ingredient in an ophthalmically acceptable medium to form a suspension and heating said suspension until the active pharmaceutical ingredient is substantially dissolved in the ophthalmically acceptable medium;
b) suspending a cyclodextrin in an ophthalmically acceptable medium to form a suspension and heating said suspension until the cyclodextrin is substantially dissolved in the ophthalmically acceptable medium;

c) mixing the compositions of step a) and b) at a temperature T1 lower than 120° C. and heating the mixture at a temperature T1 lower than 120° C. for a time t; and d) cooling the resulting solution to a temperature T2 to obtain an ophthalmic composition comprising a solid complex of an active pharmaceutical ingredient and a cyclodextrin.

In the method of the third embodiment, an active pharmaceutical ingredient may be suspended in an ophthalmically acceptable medium free of cyclodextrin. The resulting suspension may have a milky appearance. Separately a cyclodextrin may be suspended in an ophthalmically acceptable medium free of active pharmaceutical ingredient. The resulting suspension may have a milky appearance. The two suspensions may be heated or sterilized by, for example, heating in an autoclave for 121° C. for 20 minutes. Then the two suspensions or hot solutions may be mixed together and the mixture may be heated until the complex of active pharmaceutical ingredient and cyclodextrin is formed, and no degradation product is formed. The resulting solution may be cooled at a rate sufficient to produce a microsuspension comprising a solid active pharmaceutical ingredient/cyclodextrin complex.

The ophthalmic composition obtained with the methods of the first, second and third embodiments may comprise less than 2%, in particular less than 1%, more particularly less than 0.8%, by weight of impurities based on the weight of the active pharmaceutical ingredient.

The present disclosure also provides methods for preparing dexamethasone ophthalmic compositions according to the disclosure.

Accordingly, in a fourth embodiment, the method of preparing an ophthalmic composition, comprising the steps of:

a) suspending dexamethasone and γ-cyclodextrin in an ophthalmically acceptable medium to form a suspension;

b) heating the suspension at a temperature T1 lower than 120° C. for a time t until the dexamethasone and the γ-cyclodextrin are substantially dissolved in the ophthalmically acceptable medium; and c) cooling the resulting solution to a temperature T2 to obtain an ophthalmic composition comprising a solid complex of dexamethasone and γ-cyclodextrin.

In a fifth embodiment, the method of preparing an ophthalmic composition comprises the steps of:

a) suspending γ-cyclodextrin in an ophthalmically acceptable medium to form a suspension;

b) heating the suspension until the γ-cyclodextrin is dissolved in the ophthalmically acceptable medium;

c) adding dexamethasone in solid form in the solution of step b) at a temperature T1 lower than 120° C. and heating the mixture at a temperature T1 lower than 120° C. for a time t until the dexamethasone is substantially dissolved in the ophthalmically acceptable medium; and d) cooling the resulting solution to a temperature T2 to obtain an ophthalmic composition comprising a solid complex of dexamethasone and γ-cyclodextrin.

In a sixth embodiment, the method of preparing an ophthalmic composition comprises the steps of:

a) suspending dexamethasone in an ophthalmically acceptable medium to form a suspension and heating said suspension until the dexamethasone is substantially dissolved in the ophthalmically acceptable medium;

b) suspending γ-cyclodextrin in an ophthalmically acceptable medium to form a suspension and heating said suspension until the γ-cyclodextrin is substantially dissolved in the ophthalmically acceptable medium;

c) mixing the compositions of steps a) and b) at a temperature T1 lower than 120° C. and heating the mixture at a temperature T1 lower than 120° C. for a time t; and d) cooling the resulting solution to a temperature T2 to obtain an ophthalmic composition comprising a solid complex of dexamethasone and γ-cyclodextrin.

The ophthalmic compositions obtained with the methods of the third, fourth and fifth embodiments may comprise less than 0.5%, in particular less than 0.3%, more particularly less than 0.2%, by weight of 16,17-unsaturated dexamethasone and dexamethasone enol aldehydes based on the weight of dexamethasone.

The heating step of the methods of the disclosure is carried out at a temperature T1 lower than 120° C. so as to avoid generation of impurities. In particular, temperature T1 may be from 80 to 110° C., more particularly from 85 to 105° C., even more particularly from 90 to 100° C.

The heating step of the methods of the disclosure is carried out for a time t. In particular, the heating time t is from 5 minutes to 2 hours, more particularly from 10 minutes to 1 hour, even more particularly from 15 to 30 minutes.

During the heating cycle, the active pharmaceutical ingredient and/or the cyclodextrin are dissolved and the complex of active pharmaceutical ingredient and cyclodextrin is formed. Heating is accomplished by any method or means known to those having ordinary skill in the art. In preferred embodiments, the heating is accomplished with an autoclave or a jacketed reactor with steam.

The cooling step of the methods of the disclosure lowers the temperature of the composition from temperature T1 to temperature T2 in order to precipitate the solid complex of active pharmaceutical ingredient and cyclodextrin. In particular, temperature T2 may be from 10 to 40° C., more particularly from 15 to 35° C., even more particularly from 20 to 30° C.

The cooling rate of the methods of the disclosure may be carried by lowering temperature T1 to temperature T2 with a rate of 1 to 25° C./min, in particular 2 to 20° C./min, more particularly 5 to 18° C./min.

The cooling may be accomplished by any method or means known to those having ordinary skill in the art. In preferred embodiments, the cooling is accomplished with an ice bath or a jacketed reactor with a coolant.

In the methods of some exemplary embodiments, for example, the first, second, third, fourth, fifth and sixth embodiments, the suspension of step a) may further comprise a polymer as defined above. In the methods of the third and sixth embodiments, the suspension of step b) may further comprise a polymer as defined above. When the initial suspension comprises a polymer, part of the polymer may be taken up within the solid complex and/or part of the polymer may be coated on the surface of the solid complex. The microsuspension obtained with the method of the disclosure may thus comprise a microparticle drug/cyclodextrin/polymer complex. Said drug/cyclodextrin/polymer complex may comprise a polymer coating.

When a polymer is introduced in the initial suspension of the methods of the disclosure, the ophthalmic composition obtained with said methods may exhibit a viscosity of 4 to 14 cP, preferably 5 to 13 cP, more preferably 6 to 12 cP.

The viscosity of the compositions obtained with the methods of the disclosure is higher than that of compositions obtained with known manufacturing methods. Without wishing to be bound by theory, Applicants believe that the implementation of the controlled cooling step of the method, in particular with a cooling rate of 1 to 25° C./min, after the heating step allows less polymer to be included in the solid complex, and therefore more polymer is found in solution, thereby increasing the viscosity of the formulation. Hence, the original manufacturing process disclosed in the present application enables to obtain new formulations with increased viscosity with similar amounts of polymer, cyclodextrin and active pharmaceutical ingredient, as prior art formulations.

In the methods of the exemplary embodiments, for example, the first, second, third, fourth, fifth and sixth embodiments, the ophthalmically acceptable medium may comprise water and optionally an additive selected from the group consisting of a preservative, a stabilizing agent, an electrolyte, a buffering agent, and combinations thereof.

In exemplary methods, for example, the first, second, fourth and fifth embodiments, the ophthalmically acceptable medium of step a) may comprise water and optionally an additive selected from the group consisting of a preservative, a stabilizing agent, an electrolyte, a buffering agent, and combinations thereof.

In further exemplary methods, for example, the third and sixth embodiments, the ophthalmically acceptable medium of step a) may comprise only water and the ophthalmically acceptable medium of step b) may comprise water and optionally an additive selected from the group consisting of a preservative, a stabilizing agent, an electrolyte, a buffering agent, and combinations thereof.

In alternative embodiments, for example, the methods of the third and sixth embodiments, the ophthalmically acceptable medium of step b) may comprise only water and the ophthalmically acceptable medium of step a) may comprise water and optionally an additive selected from the group consisting of a preservative, a stabilizing agent, an electrolyte, a buffering agent, and combinations thereof.

Uses of the Composition of the Disclosure

The ophthalmic compositions of the disclosure may be for use in the treatment of an ocular condition, in particular an anterior ocular condition or a posterior ocular condition, more particularly uveitis, macular edema, macular degeneration, retinal detachment, ocular tumors, fungal or viral infections, multifocal choroiditis, diabetic retinopathy, proliferative vitreoretinopathy (PVR), sympathetic ophthalmia, Vogt Koyanagi-Harada (VKH) syndrome, histoplasmosis, uveal diffusion, and vascular occlusion. The compositions of the disclosure may be particularly useful in treating uveitis, macular edema, diabetic retinopathy, proliferative vitreoretinopathy (PVR), and vascular occlusions.

The dexamethasone ophthalmic composition according to the disclosure may in particular be used for the treatment of macular edema. In this case, the dexamethasone ophthalmic composition according to the disclosure may be topically administered to the eye in an amount of 1 drop of composition three times per day. The amount of dexamethasone in said composition may be from 1 to 2%, in particular 1.5% by weight of dexamethasone based on the volume of the composition.

The compositions of the disclosure do not need to be administered as frequently as know topical dexamethasone compositions, i.e. 1 drop of composition six times per day. Indeed, due to the enhanced viscosity of the composition, the solid complexes of the composition of the disclosure exhibit higher contact time on the surface of the eye compared to known compositions which increases the bioavailability of the active pharmaceutical ingredient.

The present disclosure also covers the use of the ophthalmic composition of the disclosure as an eye drop solution.

Measuring Methods

Diameter

The diameter of a particle, such as a solid complex of active pharmaceutical ingredient and cyclodextrin, can correspond to the $D_{50}$ diameter of the particle. Diameter $D_{50}$ is also known as the median diameter or the medium value of the particle size distribution. Diameter $D_{50}$ corresponds to the value of the particle diameter at 50% in the cumulative distribution. For example, if $D_{50}$ is 5 µm, then 50% of the particles in the sample are larger than 5 µm, and 50% smaller than 5 µm. Diameter $D_{50}$ is usually used to represent the particle size of a group of particles.

The diameter and/or size of a particle or complex can be measured according to any method known to those of ordinary skill in the art. For example, the diameter $D_{50}$ is measured by laser diffraction particle size analysis. Generally, there are a limited number of techniques for measuring/evaluating cyclodextrin/drug particle or complex diameter and/or size. In particular, persons of ordinary skill in this field know that the physical properties (e.g. particle size, diameter, average diameter, mean particle size, etc.) are typically evaluated/measured using such limited, typical known techniques. For example, such known techniques are described in Int. J. Pharm. 493(2015), 86-95, cited above in paragraph [00076], which is incorporated by reference herein in its entirety. In addition, such limited, known measurement/evaluation techniques were known in the art as evidenced by other technical references such as, for example, European Pharmacopoeia (2.9.31 Particle size analysis by laser diffraction, January 2010), and Saurabh Bhatia, Nanoparticles types, classification, characterization, fabrication methods and drug delivery applications, Chapter 2, Natural Polymer Drug Delivery Systems, PP. 33-94, Springer, 2016, which are also incorporated by reference herein in their entireties.

For particle size of complexes comprising an active pharmaceutical ingredient other than dexamethasone, the particle size is measured by laser diffraction particle size analysis according to Pharm. Eur. 2.9.31.

For particle size of complexes comprising dexamethasone, the particle size is measured by laser diffraction particle size analysis according to Pharm. Eur. 2.9.31 with the following parameters:

System: Malvern Mastersizer 3000 with hydro MV disperser
Fraunhofer approximation
Dispersant: water
Refractive index of the dispersant: 1.33
Time of measurement: 1 second
Time of measurement of the background: 10 second
Stirrer speed: 1200 rpm
Obscuration range: 1-20%
Model: standard
Sample preparation: Homogenize the eye drops by shaking
Sample size: addition of 0.5 ml eye drop to the disperser
Cleaning: rinsing twice with the dispersant (water) and start a measurement, checking that beam strength is less than 120 units in the first channels, and loading a background.

Viscosity

The viscosity of a composition corresponds to the dynamic viscosity of said composition. The viscosity is measured at 25° C. with a Brookfield digital viscometer. The viscosity of a composition is measured shortly after, i.e. less than 24 hours after, the preparation of the composition.

Percentage of Drug in Solid Complex and Percentage of Dissolved Drug

The amount of drug in the form of solid complexes and the amount of dissolved drug is obtained by centrifuging the composition at 6000 rpm at a temperature of 22-230 C for 20-30 minutes.

The amount of dissolved drug corresponds to the amount of drug in the supernatant as measured by high-performance liquid chromatography.

The percentage of drug in the form of a solid complex is obtained with the following formula:

$$\% \text{ drug in solid complex} = \frac{(\text{total drug} - \text{dissolved drug})}{\text{total drug}} \times 100$$

wherein

"total drug" is the total amount of drug introduced in the composition in mg/mL; and "dissolved drug" is the amount of drug in the supernatant in mg/mL.

The percentage of dissolved drug is obtained with the following formula:

$$\% \text{ dissolved drug} = 100 - \% \text{ drug in solid complex}$$

EXAMPLES

The following Examples are detailed by way of illustration only and are not to be construed as limiting in spirit or in scope, many modifications both in materials and in methods will be apparent to those skilled in the art.

Example 1

The composition of the aqueous dexamethasone eye drops are as follows: dexamethasone (1.50%), γ-cyclodextrin (14.00%), poloxamer 407 (2.50%), benzalkonium chloride (0.02%), disodium edetate (0.10%), sodium chloride (0.57%) in purified water, all w/v %. Five different methods are applied.

F1: dissolving or suspending the ingredients, including dexamethasone, in pure water and autoclaving the mixture in sealed vial at 121° C. for 20 minutes. The vials comprising a substantially clear aqueous solution are removed from the autoclave, and become cloudy with cooling to ambient temperature. The solid particles are analyzed by Fourier transform infra-red spectroscopy (FTIR), differential scanning calorimetry (DSC) and x-ray diffraction (XRD) indicating that the solid particles comprise dexamethasone/γ-cyclodextrin complexes.

F2: dissolving or suspending the ingredients, including dexamethasone, in pure water and heating the mixture over 30 minutes to 90° C. to form a clear solution. Further heating at 90° C. for 15 minutes the solution is allowed cool and become cloudy at ambient temperature reaching room temperature within approximately 3 hours.

F3: dissolving or suspending the pharmaceutical excipients in pure water, heating the mixture to 90° C. to form clear solution and then adding solid dexamethasone powder to the hot solution. When dexamethasone is dissolved (under stirring for 15 minutes) the solution is allowed cool and become cloudy at ambient temperature reaching room temperature within approximately 3 hours.

F4: dissolving or suspending the pharmaceutical excipients in pure water and autoclaving the mixture in sealed vial at 121° C. for 20 minutes to form clear solution. After cooling to 95° C. solid dexamethasone powder is added to the solution. When dexamethasone is dissolved (under stirring for 15 minutes) the solution is allowed cool and become cloudy at ambient temperature reaching room temperature over approximately 3 hours.

F5: dissolving or suspending the pharmaceutical excipients in pure water and autoclaving the mixture in sealed vial at 121° C. for 20 minutes to form clear solution. After cooling to 95° C. solid dexamethasone powder is added to the solution. When dexamethasone is dissolved (under stirring for 15 minutes) the solution was rapidly cooled to room temperature (over 20 minutes) and becomes cloudy with cooling.

F6: the excipients were separated into two parts, A and B. In part A, all the excipients except γ-cyclodextrin were dissolved in pure water at 80° C. and, in part B γ-cyclodextrin was suspended (or dissolved) separately in pure water at 80° C. The dexamethasone was added to the excipient mixture just before sterilization. The two parts of the excipient mixture in water containing dexamethasone (part A) and γ-cyclodextrin suspended (or dissolved) in water (part B), were sterilized at 121° C. for 15 minutes. After sterilization, the sterile γ-cyclodextrin was added to the rest of the sterile excipients at 95° C. In other words, parts A and B were mixed. After stirring for 15 minutes the solution was rapidly cooled to room temperature (over 20 minutes) to form cloudy suspension. F6 did not contain benzalkonium chloride.

TABLE 1

Results of the microparticle formation studies.
Mean of three determinations ± standard deviation.

| | Formulation | | | | | |
|---|---|---|---|---|---|---|
| | F1 | F2 | F3 | F4 | F5 | F6 |
| pH | 4.5 | 5.1 | 5.0 | 5.0 | 4.7 | 4.7 |
| Solid dexamethasone fraction (%) | 87.6 ± 0.0 | 70.8 ± 0.0 | 68.1 ± 0.1 | 73.0 ± 0.2 | 87.1 ± 0.1 | 83.9 ± 0.6 |
| Solid γ-cyclodextrin fraction (%) | 91.6 ± 0.0 | 89.6 ± 3.4 | 90.1 ± 3.4 | 88.8 ± 0.0 | 89.9 ± 0.0 | — |
| Viscosity at 25° C. (cP) | 3.68 ± 0.29 | 6.48 ± 0.07 | 6.64 ± 0.12 | 8.18 ± 0.05 | 8.67 ± 0.30 | 11.1 ± 0.1 |
| Mean particle size (μm) | 4.4 ± 2.7 | | | | 3.6 | 3.3 |

The results show that rapid cooling (F5) gives microsuspension where more than about 80% of the active pharmaceutical ingredient and γ-cyclodextrin are in the solid phase as active pharmaceutical ingredient/γ-cyclodextrin complexes and where most of the polymer is in the aqueous solution (i.e. have the highest viscosity). F1 settles over time, but is capable of being re-dispersed with some agitation. However, F5 has a low tendency to settle over time and is readily re-dispersed with agitation. Thus, F5 displays significant greater physical stability than F1.

Example 2

The composition of the aqueous irbesartan eye drops is as follows: irbesartan (2.0%), γ-cyclodextrin (10.0%), HPMC (0.20%), tyloxapol (0.10%), benzalkonium chloride (0.02%), disodium edetate (0.10%), sodium chloride (0.50%) in purified water, all w/v %. Three different methods are applied:

F7: dissolving or suspending the ingredients, including irbesartan, in pure water and autoclaving the mixture in sealed vial at 121° C. for 20 minutes to form clear solution. The clear aqueous solution is allowed to cool to ambient temperature and become cloudy.

F8: dissolving or suspending the pharmaceutical excipients in pure water and autoclaving the mixture in sealed vial at 121° C. for 20 minutes to form clear solution. After cooling to 95° C. solid irbesartan powder is added to the solution. When irbesartan was dissolved (15 minutes) the solution is allowed cool and become cloudy at ambient temperature reaching room temperature within approximately 3 hours.

F9: dissolving or suspending the pharmaceutical excipients in pure water and autoclaving the mixture in sealed vial at 121° C. for 20 minutes to form clear solution. After cooling to 95° C. solid irbesartan powder is added to the solution. When irbesartan is dissolved (15 minutes) the solution is rapidly cooled to room temperature (within 20 minutes) and became cloudy.

For formulation F7, the formulation can have a solid drug fraction of 54%, a viscosity at 25° C. (cP) of 4.36 and a mean particle size (μm) of 2.44.

Example 3

The dehydration of dexamethasone during preparation of the aqueous dexamethasone eye drops described in Example 1 (formulations F1, F2, F3, F4, F5 and F6) is determined by quantitative determination of 16,17-unsaturated dexamethasone and the dexamethasone enol aldehydes in the eye drops after manufacturing. Formulations F12, F13 and F14 are prepared as described in F1, that is by dissolving or suspending the ingredients, including dexamethasone, in pure water and autoclaving the mixture in sealed vial at 121° C. for 20 minutes. The substantially clear aqueous vials are removed from the autoclave and become cloudy upon cooling at ambient conditions. The composition of F12 is identical to F1, but does not contain γ-cyclodextrin. F13 comprises dexamethasone and γ-cyclodextrin suspended in pure water. F14 comprises dexamethasone suspended in pure water. The effect of excipients and preparation methods on the formation of 16,17-unsaturated dexamethasone and the dexamethasone enol aldehydes is presented as the fraction (in %) of dexamethasone degraded to form 16,17-unsaturated dexamethasone and the dexamethasone enol aldehydes.

TABLE 2

| | Formulation | | | | | | | | |
| --- | --- | --- | --- | --- | --- | --- | --- | --- | --- |
| | F1 | F2 | F3 | F4 | F5 | F6 | F12 | F13 | F14 |
| Autoclaving at 121° C. for 20 min. with dexamethasone | X | | | | | X | X | X | X |
| Heating to 90° C. for 15 min. with dexamethasone | | X | X | X | X | X | | | |
| Comprises γ-cyclodextrin | Yes | Yes | Yes | Yes | Yes | Yes | No | Yes | No |
| pH | 4.5 | 5.1 | 5.0 | 5.0 | 4.7 | 4.8 | | | |
| Fraction of dexamethasone in solution (%) | 12.4 | 29.2 | 31.9 | 27.0 | 12.9 | 16.1 | 1.17 | 4.16 | 5.73 |
| Fraction degraded to 16, 17-unsaturated dexamethasone and enol aldehydes (%) | 1.45 | 0.16 | 0.11 | 0.11 | 0.08 | 0.20 | 0.18 | 1.34 | 0.13 |

The results presented in Table 2 show that formation of 16,17-unsaturated dexamethasone and dexamethasone enol aldehydes is catalyzed by the presence of γ-cyclodextrin during heating in an autoclave, formulation F1 (comprises all the excipients) and F13 (comprises γ-cyclodextrin but not the other excipients). Much less 16,17-unsaturated dexamethasone and the dexamethasone enol aldehydes are formed in the aqueous eye drop formulation when γ-cyclodextrin is removed from the formulation (F12) or when the eye drops are prepared by heating to 90° C. for 15 minutes (F2, F3 and F4). Little or no 16,17-unsaturated dexamethasone and dexamethasone enol aldehydes are formed in the eye drops during storage at room temperature (22-23° C.) for over 12 months. During formulation of F6 aqueous suspension of γ-cyclodextrin and separately aqueous suspension containing dexamethasone and all other ingredients except γ-cyclodextrin were autoclaved at 121° C. for 15 minutes. After autoclaving the two suspensions/solutions were cooled to 95° C. before mixing and then cooled further to ambient temperature (see Example 1). Only minor amount of 16,17-unsaturated dexamethasone and the dexamethasone enol aldehydes is formed in the aqueous eye drop formulation when dexamethasone is sterilized in absence of γ-cyclodextrin.

Example 4

The amount of 16,17-unsaturated dexamethasone and dexamethasone enol aldehydes formed, presented as the fraction (in %) of dexamethasone degraded to form 16,17-unsaturated dexamethasone and dexamethasone enol aldehydes, in aqueous eye drops after no autoclaving (i.e., heating to 121° C. for 20 minutes) once, twice and three times is shown in Table 3.

TABLE 3

| pH | Number of autoclaving cycles | | | |
|---|---|---|---|---|
| | 0 | 1 | 2 | 3 |
| 2.5 | 0.08% | 1.06% | 2.29% | 3.12% |
| 4.0 | 0.08% | 1.14% | 2.19% | 3.03% |
| 5.5 | 0.08% | 1.22% | 2.27% | 3.46% |
| 7.0 | 0.08% | 0.86% | 1.64% | 2.57% |

The amount of 16,17-unsaturated dexamethasone and dexamethasone enol aldehydes formed, presented as the fraction (in %) of dexamethasone degraded to form 16,17-unsaturated dexamethasone and dexamethasone enol aldehydes, in the aqueous eye drops after no autoclaving (i.e. heating to 121° C. for 20 minutes), once, twice and three times is shown below.

Formation of 16,17-unsaturated dexamethasone and dexamethasone enol aldehydes is observed at all four pH tested. Although, less 16,17-unsaturated dexamethasone and dexamethasone enol aldehydes are formed at pH 7.0 than at 5.5 other degradation products appeared. According to the British Pharmacopoeia 2015 (version 19.0) the pH of aqueous dexamethasone eye drop suspension should be between 5.0 and 6.0.

Example 5

The degradation of dexamethasone in F1 was investigated at 25° C., 40° C., 60° C., 70° C. and 95° C. The apparent first-order rate constants for the dexamethasone disappearance were determined, and the apparent activation energy calculated with the help of Arrhenius Equation. The equation was also used to estimate the first-order rate constant for the dexamethasone disappearance at 25° C. The time for 10% ($t_{90}$; the shelf-life) and 0.5% ($t_{99.5}$) degradation was also calculated from the rate constants.

TABLE 4

The first-order rate constant for the degradation of dexamethasone in aqueous eye drop formulation comprising γ-cyclodextrin (i.e. F5) at pH 7.0.

| | 25° C. | 40° C. | 60° C. | 70° C. | 95° C. |
|---|---|---|---|---|---|
| First-order rate constant (k in $h^{-1}$) | 1.442 · $10^{-7}$ | 2.483 · $10^{-6}$ | 2.476 · $10^{-5}$ | 2.044 · $10^{-4}$ | 3.277 · $10^{-3}$ |
| Shelf-life ($t_{90}$ in days) | 30,444 | 1,768 | 177 | 21.5 | 1.3 |

TABLE 4-continued

The first-order rate constant for the degradation of dexamethasone in aqueous eye drop formulation comprising γ-cyclodextrin (i.e. F5) at pH 7.0.

| | 25° C. | 40° C. | 60° C. | 70° C. | 95° C. |
|---|---|---|---|---|---|
| Time for 0.5% degradation ($t_{99.5}$ in hours) | 34,761 | 2,018 | 202 | 24.5 | 1.5 |
| Apparent activation energy ($E_a$) | | $32.2 \frac{kcal}{mol} = 134.5 \frac{kJ}{mol}$ | | | |
| Estimated shelf-life ($t_{90}$) at 25° C. | | | 83.4 years | | |
| Estimated time for 0.5% degradation ($t_{99.5}$) at 25° C. | | | 4.0 years | | |

In general, values of Ea range from about 50 to 85 kJ/mol and values greater than 100 kJ/mol are very uncommon. The apparent value of Ea for dehydration of dexamethasone in aqueous γ-cyclodextrin solution to form 16,17-unsaturated dexamethasone and the dexamethasone enol aldehydes is 134.5 kJ/mol and, thus, 16,17-unsaturated dexamethasone and the dexamethasone enol aldehydes are only formed in aqueous γ-cyclodextrin solutions at exceptionally high temperatures.

Example 6

The effect of the cooling rate on the size of the microparticles is examined. The dexamethasone eye drop vehicle contained contains γ-cyclodextrin (14.00%), poloxamer 407 (2.50%), benzalkonium chloride (0.02%), disodium edetate (0.10%), sodium chloride (0.57%) in purified water, all w/v %. The vehicle is heated in an autoclave (121° C. for 20 min) in sealed vial to form a substantially clear solution. After cooling to 95° C. solid dexamethasone powder (1.50% w/v) is added to the solution. After dexamethasone is dissolved (under stirring for 15 minutes), the solution is divided into small portions (approx. 5 ml) and is placed into thermostated water set to different temperatures. The temperature changes are recorded against time. The particle size and the viscosity of the resulting suspensions are determined.

Example 7

The effect of sterilization time and temperature, and the effect of mixing time, is examined in the case of formulation F6. Formulations are prepared as described in Example 1. During formulation of F6 aqueous suspension of γ-cyclodextrin (part B) and separately aqueous suspension containing dexamethasone and all other ingredients except γ-cyclodextrin (part A) are autoclaved at 121° C. for 15 minutes. After autoclaving the two suspensions/solutions are cooled to 95° C. before mixing and then are cooled further to ambient temperature (see Example 1 and Example 3).

The modified technological parameters during sterilization and mixing of γ-cyclodextrin to the other excipients and the resulting amounts of fraction degraded to 16,17-unsaturated dexamethasone and dexamethasone enol aldehydes are shown in Table 5.

TABLE 5

| Formulation | Sterilization | Mixing with the γCD soln. at 95° C. | Amount of 16, 17-unsaturated dexamethasone and dexamethasone enol aldehydes (%) |
|---|---|---|---|
| F6 | 15 min, 121° C. | 15 min | 0.20 |
| F6a | 15 min, 121° C. | No γCD | 0.05 |
| F6b | 2 × 15 min, 121° C. | No γCD | 0.10 |
| F6c | 15 min, 121° C. | 30 min | 0.28 |
| F6d | 2 × 15 min, 121° C. | 15 min | 0.25 |
| F6e | 15 min, 135° C. | 15 min | 0.34 |

Formulation F6a and F6b do not contain any γCD and show only the effect of the sterilization step. F6a was sterilized in an autoclave once for 15 min at 121° C. while F6b went through two sterilization cycles at the same conditions. One sterilization cycle added 0.05% of 16,17-unsaturated dexamethasone and dexamethasone enol aldehydes (% of the total amount of dexamethasone in the eye drops) and two sterilization cycles added 0.10% of 16,17-unsaturated dexamethasone and dexamethasone enol aldehydes.

Formulation F6c shows the effect of double mixing time at 95° C. after the addition of γCD. An extra 15 minute of mixing adds an extra 0.08% of 16,17-unsaturated dexamethasone and dexamethsone enol aldehydes to the 0.20% of F6.

Formulation F6d shows the effect of double autoclaving (two sterilization cycles) combined together with the 15 minutes mixing at 95° C. after the addition of γCD. The double sterilization added an extra 0.05% of 16,17-unsaturated dexamethasone and dexamethasone enol aldehydes to the 0.20% of F6, which corresponds with the results of the F6a and F6b formulations not containing γCD.

Formulation F6e shows the effect of sterilizing at 135° C. instead of 121° C. for 15 minutes, and then 15 min mixing at 95° C. after the addition of γCD. The amount of 16,17-unsaturated dexamethasone and dexamethasone enol aldehydes increased from 0.20% to 0.34%.

The results show that the manufacturing method is robust and small changes in the technological parameters will essentially not affect the amount of 16,17-unsaturated dexamethasone and dexamethasone enol aldehydes in the final product.

Example 8

Manufacturing process F6 was implemented on industrial scale. The composition of the aqueous dexamethasone eye drops are as follows: dexamethasone (1.50% w/v), γ-cyclodextrin (14.00% w/v), poloxamer 407 (2.50% w/v), disodium edetate (0.10% w/v), sodium chloride (0.57% w/v) in purified water The batch size was 400 liters (F15).

F15: Dexamethasone and all the excipients except γ-cyclodextrin were dissolved or suspended in pure water at 80° C. (Solution A). γ-Cyclodextrin was dissolved separately in pure water at 80° C. (Solution B). Solution A and Solution B were sterilized at 121° C. for 15 minutes. After sterilization and cooling Solution A and Solution B were mixed. The mixture was then reheated to 95° C. and kept at that temperature under stirring for 15 minutes. The solution was cooled to 40° C. in under 40 minutes and then to room temperature (within another 40 minutes). Then the resulting microsuspension upon was filled into unit dose containers. See Table 6.

TABLE 6

| Parameter | Formulation F15 |
|---|---|
| pH | 4.5 |
| $D_{50}$ (µm) | 7.2 |
| Fraction degraded to 16, 17-unsaturated dexamethasone and dexamethasone enol aldehydes | 0.3% |
| Uniformity of dosage units (L1 <15 according to Ph.Eur.) | L1 = 3.9 |

Example 9

The composition of the aqueous dexamethasone eye drops (F16) are as follows: dexamethasone (1.50%), γ-cyclodextrin (14.00%), poloxamer 407 (2.50%), disodium edetate (0.10%), sodium chloride (0.57%) in purified water, all w/v %. The excipients were separated into two parts, A and B. In A all the excipients except γ-cyclodextrin were dissolved in pure water at 80° C. and in B γ-cyclodextrin was dissolved separately in pure water at 80° C. The dexamethasone was added to the excipient mixture just before sterilization. The excipient mixture in water containing dexamethasone (A) and γ-cyclodextrin dissolved in water (B), were sterilized at 121° C. for 15 minutes. After sterilization, A and B were mixed at 95° C. After stirring for 15 minutes the solution was cooled from 95° C. to 40° C. at three different cooling rates (ΔT/Δt). The cooling rate of F16a was 17.7° C./min, that of F16b 1.3° C./min and that of F16c 1.2° C./min (Table 7).

TABLE 7

|  | F16a | F16b | F16c |
|---|---|---|---|
| ΔT/Δt (° C./min) | 17.7 | 1.3 | 1.2 |
| $D_{50}$ (µm) | 3.3 | 7.2 | 8.8 |
| Viscosity (cP) | 11.1 | 9.0 | not determined |

The table shows how the mean particle size is controlled by the cooling rate. The faster the cooling rate, the smaller the particles and the higher the viscosity.

Example 10

Kinase inhibitors were suspended in aqueous solutions containing from 1% (w/v) to 15% (w/v) γ-cyclodextrin. Heating of the suspensions formed in an autoclave (121° C. for 15 min) resulted in up to 50% degradation of the kinase inhibitors whereas heating to 95° C. for 15 min and rapid cooling to 25° C. resulted in significant less degradation and produced microparticle suspension. The solubility of the kinase inhibitors in pure water ($S_0$) and the stability constant ($K_{1:1}$) of the active pharmaceutical ingredient/γ-cyclodextrin complexes were determined from the initial linear art of the phase-solubility profiles (Table 8).

TABLE 8

| Kinase Inhibitor | $S_0$ (mg/mL) | $K_{1:1}$ ($M^{-1}$) |
|---|---|---|
| Axitinib | 0.0004 | 260 |
| Cediranib | 1.2 | 23 |
| Dovitinib | 0.006 | 680 |
| Motesanib | 0.014 | 140 |
| Pazopanib | 0.0006 | 13 |
| Regorafenib | 0.0001 | 94 |

Example 11

Kinase inhibitors were suspended in aqueous media consisting of pure water, aqueous γ-cyclodextrin solution, aqueous solution containing γ-cyclodextrin and tyloxapol (1% w/v), and aqueous eye drop medium containing γ-cyclodextrin, benzalkonium chloride (0.02% w/v), disodium edetate (0.10% w/v) and sodium chloride (0.05% w/v). The concentration of γ-cyclodextrin varied depending on the kinase inhibitor. The solubility was determined as described in Example 10. Table 9 shows the γ-cyclodextrin concentration and the effect of tyloxapol and the eye drop excipient mixture on the γ-cyclodextrin solubilization of the kinase inhibitors.

TABLE 9

| Kinase Inhibitor | γ-Cyclodextrin concentration (% w/v) | Solubility (mg/mL) | | |
|---|---|---|---|---|
| | | γ-Cyclodextrin | Tyloxapol | Eye drops |
| Axitinib | 4 | 0.003 | 0.008 | 0.007 |
| Cediranib | 12 | 2.0 | 2.8 | 4.1 |
| Motesanib | 8 | 0.09 | 0.04 | 0.07 |
| Pazopanib | 16 | 0.007 | 0.006 | 0.01 |
| Regorafenib | 4 | 0.0005 | 0.005 | 0.0008 |

The results show that the excipients can have significant effect on the kinase inhibitor solubilization.

Example 12

Dovitinib is suspended in aqueous solutions containing from 1% (w/v) to 15% (w/v) γ-cyclodextrin. Heating of the suspensions formed in an autoclave (121° C. for 15 min) should result in degradation of dovitinib whereas heating to 95° C. for 15 min and cooling to 25° C. over 20 minutes should result in a composition comprising solid dovitinib/γ-cyclodextrin complexes and significantly less degradation of dovitinib.

Example 13

Losartan is suspended in aqueous solutions containing from 1% (w/v) to 15% (w/v) γ-cyclodextrin. Heating of the suspensions formed in an autoclave (121° C. for 15 min) should result in degradation of losartan whereas heating to 95° C. for 15 min and cooling to 25° C. over 20 minutes should result in a composition comprising solid losartan/γ-cyclodextrin complexes and significantly less degradation of losartan.

Example 14

Olmesartan is suspended in aqueous solutions containing from 1% (w/v) to 15% (w/v) γ-cyclodextrin. Heating of the suspensions formed in an autoclave (121° C. for 15 min) should result in degradation of olmesartan whereas heating to 95° C. for 15 min and cooling to 25° C. over 20 minutes should result in a composition comprising solid olmesartan/γ-cyclodextrin complexes and significantly less degradation of olmesartan.

Example 15

Dorzolamide is suspended in aqueous solutions containing from 1% (w/v) to 15% (w/v) γ-cyclodextrin. Heating of the suspensions formed in an autoclave (121° C. for 15 min) should result in degradation of dorzolamide whereas heating to 95° C. for 15 min and cooling to 25° C. over 20 minutes should result in a composition comprising solid dorzolamide/γ-cyclodextrin complexes and significantly less degradation of dorzolamide.

Example 16

Diclofenac is suspended in aqueous solutions containing from 1% (w/v) to 15% (w/v) γ-cyclodextrin. Heating of the suspensions formed in an autoclave (121° C. for 15 min) should result in degradation of diclofenac whereas heating to 95° C. for 15 min and cooling to 25° C. over 20 minutes should result in a composition comprising solid diclofenac/γ-cyclodextrin complexes and significantly less degradation of diclofenac.

Example 17

Nepafenac is suspended in aqueous solutions containing from 1% (w/v) to 15% (w/v) γ-cyclodextrin. Heating of the suspensions formed in an autoclave (121° C. for 15 min) should result in degradation of nepafenac whereas heating to 95° C. for 15 min and cooling to 25° C. over 20 minutes should result in a composition comprising solid nepafenac/γ-cyclodextrin complexes and significantly less degradation of nepafenac.

Any numbers expressing quantities of ingredients, constituents, reaction conditions, and so forth used in the specification are to be understood as being modified in all instances by the term "about." Notwithstanding that the numerical ranges and parameters setting forth, the broad scope of the subject matter presented herein are approximations, the numerical value set forth are indicated as precisely as possible. Any numerical value, however, may inherently contain certain error or inaccuracies as evident from the standard deviation found in their respective measurement techniques. None of the features recited herein should be interpreted as invoking 35 U.S.C. § 112(f), or pre-AIA ¶6, unless the term "means" is explicitly used.

Although the present invention has been described in connection with exemplary embodiments thereof, it will be appreciated by those skilled in the art that additions, deletions, modifications, and substitutions not specifically described may be made without departing from the spirit and scope of the disclosure.

What is claimed is:

1. An ophthalmic microsuspension comprising, in an ophthalmically acceptable medium:
    a solid complex comprising an active pharmaceutical ingredient and a cyclodextrin,
    wherein said solid complex has a diameter $D_{50}$ from about 1 μm to about 25 μm, wherein the active pharmaceutical ingredient is a steroid,
wherein the microsuspension comprises less than 1% by weight of by-products of the active pharmaceutical ingredient based on the weight of the active pharmaceutical ingredient, and
wherein the microsuspension is prepared by a process comprising:
a) mixing a sterile suspension or solution of the active pharmaceutical ingredient and a sterile suspension or solution of the cyclodextrin at a temperature T1 for a time t until the active pharmaceutical ingredient and the cyclodextrin are substantially dissolved to form a resulting mixture, wherein the temperature T1 is from 80° C. to less than 120° C.; and
b) cooling the resulting mixture to obtain the ophthalmic microsuspension comprising the solid complex.

2. The ophthalmic microsuspension of claim 1, wherein the sterile suspension or solution of the active pharmaceutical ingredient and/or the sterile suspension or solution of cyclodextrin are sterilized in an autoclave prior to mixing.

3. The ophthalmic microsuspension of claim 1, wherein the temperature T1 is from 80° C. to 110° C.

4. The ophthalmic microsuspension of claim 3, wherein the temperature T1 is from 85° C. to 105° C.

5. The ophthalmic microsuspension of claim 1, wherein in step b), cooling the resulting mixture comprises reducing the temperature T1 to a temperature T2, and wherein the temperature T2 is from 10° C. to 40° C.

6. The ophthalmic microsuspension of claim 5, wherein in step b), cooling the resulting mixture comprises reducing the temperature T1 to the temperature T2 at a rate of 1° C./min to 25° C./min.

7. The ophthalmic microsuspension of claim 1, wherein the time t is from 5 minutes to 2 hours.

8. The ophthalmic microsuspension of claim 1, wherein the steroid is selected from the group consisting of dexamethasone, difluprednate, estradiol, fluocinolone, fluorometholone, hydrocortisone, loteprednol etabonate, prednisolone, triamcinolone, rimexolone, and combinations thereof.

9. The ophthalmic microsuspension of claim 8, wherein the steroid is dexamethasone.

10. The ophthalmic microsuspension of claim 1, wherein the cyclodextrin is α-cyclodextrin, β-cyclodextrin, γ-cyclodextrin, or a combination thereof.

11. The ophthalmic microsuspension of claim 10, wherein the cyclodextrin is γ-cyclodextrin.

12. The ophthalmic microsuspension of claim 1, wherein the amount of cyclodextrin is from 1% to 25% by weight based on the volume of the microsuspension.

13. The ophthalmic microsuspension of claim 1, wherein the active pharmaceutical ingredient is present in the microsuspension at a concentration of about 0.1 mg/mL to about 100 mg/mL.

14. The ophthalmic microsuspension of claim 13, wherein the active pharmaceutical ingredient is present in the microsuspension at a concentration of 10 mg/mL to 50 mg/mL.

15. The ophthalmic microsuspension of claim 1, wherein 60% to 95% by weight of the active pharmaceutical ingredient in the microsuspension is in the form of the solid complex.

16. The ophthalmic microsuspension of claim 1, wherein 5% to 40% by weight of the active pharmaceutical ingredient in the microsuspension is in dissolved form.

17. The ophthalmic microsuspension of claim 1, wherein 0% to 0.5% by weight of the active pharmaceutical ingredient in the microsuspension is in an uncomplexed solid form.

18. The ophthalmic microsuspension of claim 1, wherein the pH of the microsuspension is between about 5.0 and about 6.0.

19. The ophthalmic microsuspension of claim 1, wherein the microsuspension further comprises a polymer.

20. The ophthalmic microsuspension of claim 19, wherein the polymer is a surface active polymer.

21. The ophthalmic microsuspension of claim 20, wherein the polymer is selected from the group consisting of a polyoxyethylene fatty acid ester, a polyoxyethylene alkylphenyl ether, a polyoxyethylene alkyl ether, a cellulose derivative, a carboxyvinyl polymer, a polyvinyl polymer, a polyvinyl alcohol, a polyvinylpyrrolidone, a copolymer of polyoxypropylene and polyoxyethylene, tyloxapol, and combinations thereof.

22. The ophthalmic microsuspension of claim 21, wherein the copolymer of polyoxypropylene and polyoxyethylene is a triblock copolymer comprising a hydrophilic block-hydrophobic block-hydrophilic block configuration.

23. The ophthalmic microsuspension of claim 19, wherein the polymer is a poloxamer.

24. A method of preparing an ophthalmic microsuspension, the method comprising the steps of:
a) mixing a sterile suspension or solution of an active pharmaceutical ingredient and a sterile suspension or solution of cyclodextrin at a temperature T1 for a time t until the active pharmaceutical ingredient and the cyclodextrin are substantially dissolved to form a resulting mixture, wherein the temperature T1 is from 80° C. to less than 120° C.; and
b) cooling the resulting mixture to obtain an ophthalmic microsuspension comprising a solid complex in an ophthalmically acceptable medium,
wherein said solid complex has a diameter $D_{50}$ from about 1 μm to about 25 μm,
wherein said active pharmaceutical ingredient is a steroid, and
wherein the microsuspension comprises less than 1% by weight of by-products of the active pharmaceutical ingredient based on the weight of the active pharmaceutical ingredient.

25. The method of claim 24, wherein the sterile suspension or solution of the active pharmaceutical ingredient and/or the sterile suspension or solution of cyclodextrin are sterilized in an autoclave prior to mixing.

26. The method of claim 24, wherein the temperature T1 is from 80° C. to 110° C.

27. The method of claim 26, wherein the temperature T1 is from 85° C. to 105° C.

28. The method of claim 24, wherein in step b), cooling the resulting mixture comprises reducing the temperature T1 to a temperature T2, and wherein the temperature T2 is from 10° C. to 40° C.

29. The method of claim 28, wherein in step b), cooling the resulting mixture comprises reducing the temperature T1 to the temperature T2 at a rate of 1° C./min to 25° C./min.

30. The method of claim 24, wherein the time t is from 5 minutes to 2 hours.

31. The method of claim 24, wherein the steroid is selected from the group consisting of dexamethasone, difluprednate, estradiol, fluocinolone, fluorometholone, hydrocortisone, loteprednol etabonate, prednisolone, triamcinolone, rimexolone, and combinations thereof.

32. The method of claim 31, wherein the steroid is dexamethasone.

33. The method of claim 24, wherein the cyclodextrin is α-cyclodextrin, β-cyclodextrin, γ-cyclodextrin, or a combination thereof.

34. The method of claim 33, wherein the cyclodextrin is γ-cyclodextrin.

35. The method of claim 33, wherein the amount of cyclodextrin is from 1% to 25% by weight based on the volume of the microsuspension.

36. The method of claim 24, wherein the active pharmaceutical ingredient is present in the microsuspension at a concentration of about 0.1 mg/mL to about 100 mg/mL.

37. The method of claim 36, wherein the active pharmaceutical ingredient is present in the microsuspension at a concentration of 10 mg/mL to 50 mg/mL.

38. The method of claim 24, wherein 60% to 95% by weight of the active pharmaceutical ingredient in the microsuspension is in the form of the solid complex.

39. The method of claim 24, wherein 5% to 40% by weight of the active pharmaceutical ingredient in the microsuspension is in dissolved form.

40. The method of claim 24, wherein 0% to 0.5% by weight of the active pharmaceutical ingredient in the microsuspension is in an uncomplexed solid form.

41. The method of claim 24, wherein the pH of the microsuspension is between about 5.0 and about 6.0.

42. The method of claim 24, wherein the microsuspension further comprises a polymer.

43. The method of claim 42, wherein the polymer is a surface active polymer.

44. The method of claim 43, wherein the polymer is selected from the group consisting of a polyoxyethylene fatty acid ester, a polyoxyethylene alkylphenyl ether, a polyoxyethylene alkyl ether, a cellulose derivative, a carboxyvinyl polymer, a polyvinyl polymer, a polyvinyl alcohol, a polyvinylpyrrolidone, a copolymer of polyoxypropylene and polyoxyethylene, tyloxapol, and combinations thereof.

45. The method of claim 44, wherein the copolymer of polyoxypropylene and polyoxyethylene is a triblock copolymer comprising a hydrophilic block-hydrophobic block-hydrophilic block configuration.

46. The method of claim 42, wherein the polymer is a poloxamer.

47. An ophthalmic microsuspension comprising, in an ophthalmically acceptable medium:
a solid complex comprising an active pharmaceutical ingredient and a cyclodextrin,
wherein said solid complex has a diameter $D_{50}$ from about 1 μm to about 25 μm,
wherein said active pharmaceutical ingredient is a steroid,
wherein the microsuspension comprises less than 1% by weight of degradation products of the active pharmaceutical ingredient based on the weight of the active pharmaceutical ingredient, and
wherein the microsuspension is prepared by a process comprising:
a) mixing a sterile suspension or solution of the active pharmaceutical ingredient and a sterile suspension or solution of the cyclodextrin at a temperature T1 for a time t until the active pharmaceutical ingredient and the cyclodextrin are substantially dissolved to form a resulting mixture, wherein the temperature T1 is from 80° C. to less than 120° C.; and
b) cooling the resulting mixture to obtain the ophthalmic microsuspension comprising the solid complex.

48. The ophthalmic microsuspension of claim 47, wherein the sterile suspension or solution of the active pharmaceutical ingredient and/or the sterile suspension or solution of cyclodextrin are sterilized in an autoclave prior to mixing.

49. The ophthalmic microsuspension of claim 47, wherein the temperature T1 is from 80° C. to 110° C.

50. The ophthalmic microsuspension of claim 49, wherein the temperature T1 is from 85° C. to 105° C.

51. The ophthalmic microsuspension of claim 47, wherein in step b), cooling the resulting mixture comprises reducing the temperature T1 to a temperature T2, and wherein the temperature T2 is from 10° C. to 40° C.

52. The ophthalmic microsuspension of claim 51, wherein in step b), cooling the resulting mixture comprises reducing the temperature T1 to the temperature T2 at a rate of 1° C./min to 25° C./min.

53. The ophthalmic microsuspension of claim 47, wherein the time t is from 5 minutes to 2 hours.

54. The ophthalmic microsuspension of claim 47, wherein the steroid is selected from the group consisting of dexamethasone, difluprednate, estradiol, fluocinolone, fluorometholone, hydrocortisone, loteprednol etabonate, prednisolone, triamcinolone, rimexolone, and combinations thereof.

55. The ophthalmic microsuspension of claim 54, wherein the steroid is dexamethasone.

56. The ophthalmic microsuspension of claim 47, wherein the cyclodextrin is α-cyclodextrin, β-cyclodextrin, γ-cyclodextrin, or a combination thereof.

57. The ophthalmic microsuspension of claim 56, wherein the cyclodextrin is γ-cyclodextrin.

58. The ophthalmic microsuspension of claim 47, wherein the amount of cyclodextrin is from 1% to 25% by weight based on the volume of the microsuspension.

59. The ophthalmic microsuspension of claim 47, wherein the active pharmaceutical ingredient is present in the microsuspension at a concentration about of 0.1 mg/mL to about 100 mg/mL.

60. The ophthalmic microsuspension of claim 59, wherein the active pharmaceutical ingredient is present in the microsuspension at a concentration of 10 mg/mL to 50 mg/mL.

61. The ophthalmic microsuspension of claim 47, wherein 60% to 95% by weight of the active pharmaceutical ingredient in the microsuspension is in the form of the solid complex.

62. The ophthalmic microsuspension of claim 47, wherein 5% to 40% by weight of the active pharmaceutical ingredient in the microsuspension is in dissolved form.

63. The ophthalmic microsuspension of claim 47, wherein 0% to 0.5% by weight of the active pharmaceutical ingredient in the microsuspension is in an uncomplexed solid form.

64. The ophthalmic microsuspension of claim 47, wherein the pH of the microsuspension is between about 5.0 and about 6.0.

65. The ophthalmic microsuspension of claim 47, wherein the microsuspension further comprises a polymer.

66. The ophthalmic microsuspension of claim 65, wherein the polymer is a surface active polymer.

67. The ophthalmic microsuspension of claim 66, wherein the polymer is selected from the group consisting of a polyoxyethylene fatty acid ester, a polyoxyethylene alkylphenyl ether, a polyoxyethylene alkyl ether, a cellulose derivative, a carboxyvinyl polymer, a polyvinyl polymer, a polyvinyl alcohol, a polyvinylpyrrolidone, a copolymer of polyoxypropylene and polyoxyethylene, tyloxapol, and combinations thereof.

68. The ophthalmic microsuspension of claim 67, wherein the copolymer of polyoxypropylene and polyoxyethylene is a triblock copolymer comprising a hydrophilic block-hydrophobic block-hydrophilic block configuration.

69. The ophthalmic microsuspension of claim 65, wherein the polymer is a poloxamer.

70. A method of preparing an ophthalmic microsuspension, the method comprising the steps of:
a) mixing a sterile suspension or solution of an active pharmaceutical ingredient and a sterile suspension or solution of a cyclodextrin at a temperature T1 for a time t until the active pharmaceutical ingredient and the cyclodextrin are substantially dissolved to form a resulting mixture, wherein the temperature T1 is from 80° C. to less than 120° C.; and
b) cooling the resulting mixture to obtain an ophthalmic microsuspension comprising a solid complex of the active pharmaceutical ingredient and the cyclodextrin in an ophthalmically acceptable medium,
wherein said solid complex has a diameter $D_{50}$ from about 1 μm to about 25 μm,
wherein said active pharmaceutical ingredient is a steroid, and
wherein the microsuspension comprises less than 1% by weight of degradation products of the active pharmaceutical ingredient based on the weight of the active pharmaceutical ingredient.

71. The method of claim 70, wherein the sterile suspension or solution of the active pharmaceutical ingredient and/or the sterile suspension or solution of cyclodextrin are sterilized in an autoclave prior to mixing.

72. The method of claim 70, wherein the temperature T1 is from 80° C. to 110° C.

73. The method of claim 72, wherein the temperature T1 is from 85° C. to 105° C.

74. The method of claim 70, wherein in step b), cooling the resulting mixture comprises reducing the temperature T1 to a temperature T2, and wherein the temperature T2 is from 10° C. to 40° C.

75. The method of claim 74, wherein in step b), cooling the resulting mixture comprises reducing the temperature T1 to the temperature T2 at a rate of 1° C./min to 25° C./min.

76. The method of claim 70, wherein the time t is from 5 minutes to 2 hours.

77. The method of claim 70, wherein the steroid is selected from the group consisting of dexamethasone, difluprednate, estradiol, fluocinolone, fluorometholone, hydrocortisone, loteprednol etabonate, prednisolone, triamcinolone, rimexolone, and combinations thereof.

78. The method of claim 77, wherein the steroid is dexamethasone.

79. The method of claim 70, wherein the cyclodextrin is α-cyclodextrin, β-cyclodextrin, γ-cyclodextrin, or a combination thereof.

80. The method of claim 79, wherein the cyclodextrin is γ-cyclodextrin.

81. The method of claim 70, wherein the amount of cyclodextrin is from 1% to 25% by weight based on the volume of the microsuspension.

82. The method of claim 70, wherein the active pharmaceutical ingredient is present in the microsuspension at a concentration of about 0.1 mg/mL to about 100 mg/mL.

83. The method of claim 82, wherein the active pharmaceutical ingredient is present in the microsuspension at a concentration of 10 mg/mL to 50 mg/mL.

84. The method of claim 70, wherein 60% to 95% by weight of the active pharmaceutical ingredient in the microsuspension is in the form of the solid complex.

85. The method of claim 70, wherein 5% to 40% by weight of the active pharmaceutical ingredient in the microsuspension is in dissolved form.

86. The method of claim 70, wherein 0% to 0.5% by weight of the active pharmaceutical ingredient in the microsuspension is in an uncomplexed solid form.

87. The method of claim 70, wherein the pH of the microsuspension is between about 5.0 and about 6.0.

88. The method of claim 70, wherein the microsuspension further comprises a polymer.

89. The method of claim 88, wherein the polymer is a surface active polymer.

90. The method of claim 89, wherein the polymer is selected from the group consisting of a polyoxyethylene fatty acid ester, a polyoxyethylene alkylphenyl ether, a polyoxyethylene alkyl ether, a cellulose derivative, a carboxyvinyl polymer, a polyvinyl polymer, a polyvinyl alcohol, a polyvinylpyrrolidone, a copolymer of polyoxypropylene and polyoxyethylene, tyloxapol, and combinations thereof.

91. The method of claim 90, wherein the copolymer of polyoxypropylene and polyoxyethylene is a triblock copolymer comprising a hydrophilic block-hydrophobic block-hydrophilic block configuration.

92. The method of claim 88, wherein the polymer is a poloxamer.

93. An ophthalmic microsuspension comprising, in an ophthalmically acceptable medium:
a solid complex comprising an active pharmaceutical ingredient and a cyclodextrin,
wherein the active pharmaceutical ingredient is a steroid,
wherein said solid complex has a diameter $D_{50}$ from about 1 μm to about 25 μm,
wherein the microsuspension comprises less than 1% by weight of by-products of the active pharmaceutical ingredient based on the weight of the active pharmaceutical ingredient, and
wherein the microsuspension is prepared by a process comprising:
a) suspending the active pharmaceutical ingredient in a first ophthalmically acceptable medium to form a suspension of the active pharmaceutical ingredient and heating said suspension until the active pharmaceutical ingredient is dissolved or substantially dissolved in the first ophthalmically acceptable medium and a solution or a suspension is formed;
b) suspending the cyclodextrin in a second ophthalmically acceptable medium to form a suspension of the cyclodextrin and heating said suspension until the cyclodextrin is dissolved or substantially dissolved in the second ophthalmically acceptable medium and a solution or a suspension is formed; and
c) mixing the suspensions or solutions of steps a) and b) at a temperature T1 and heating the mixture at a temperature higher than the temperature T1 but lower than 120° C. to obtain a resulting mixture, wherein the temperature T1 is from 80° C. to less than 120° C., and
d) cooling the resulting mixture to a temperature T2 to obtain the ophthalmic microsuspension comprising the solid complex.

94. The ophthalmic microsuspension of claim 93, wherein the solution or suspension of the active pharmaceutical ingredient of step a) and/or the solution or suspension of cyclodextrin of step b) are sterilized in an autoclave prior to their mixing in step c).

95. The ophthalmic microsuspension of claim 93, wherein the temperature T1 is from 80° C. to 110° C.

96. The ophthalmic microsuspension of claim 95, wherein the temperature T1 is from 85° C. to 105° C.

97. The ophthalmic microsuspension of claim 93, wherein in step d), the temperature T2 is 10° C. to 40° C.

98. The ophthalmic microsuspension of claim 93, wherein step d) comprises cooling the resulting mixture to the temperature T2 at a rate of 1° C./min to 25° C./min.

99. The ophthalmic microsuspension of claim 93, wherein the first and second ophthalmically acceptable media are selected from the group consisting of water, a preservative, a stabilizing agent, an electrolyte, a buffering agent, and combinations thereof.

100. The ophthalmic microsuspension of claim 99, wherein the first ophthalmically acceptable media is water and the second ophthalmically acceptable media comprises water, and optionally, an additive selected from the group consisting of a preservative, a stabilizing agent, an electrolyte, a buffering agent, and combinations thereof.

101. The ophthalmic microsuspension of claim 93, wherein the steroid is selected from the group consisting of dexamethasone, difluprednate, estradiol, fluocinolone, fluorometholone, hydrocortisone, loteprednol etabonate, prednisolone, triamcinolone, rimexolone, and combinations thereof.

102. The ophthalmic microsuspension of claim 101, wherein the steroid is dexamethasone.

103. The ophthalmic microsuspension of claim 93, wherein the cyclodextrin is α-cyclodextrin, β-cyclodextrin, γ-cyclodextrin, or a combination thereof.

104. The ophthalmic microsuspension of claim 103, wherein the cyclodextrin is γ-cyclodextrin.

105. The ophthalmic microsuspension of claim 93, wherein the amount of cyclodextrin is from 1% to 25% by weight based on the volume of the microsuspension.

106. The ophthalmic microsuspension of claim 93, wherein the active pharmaceutical ingredient is present in the microsuspension at a concentration of about 0.1 mg/mL to about 100 mg/mL.

107. The ophthalmic microsuspension of claim 106, wherein the active pharmaceutical ingredient is present in the microsuspension at a concentration of 10 mg/mL to 50 mg/mL.

108. The ophthalmic microsuspension of claim 93, wherein 60% to 95% by weight of the active pharmaceutical ingredient in the microsuspension is in the form of the solid complex.

109. The ophthalmic microsuspension of claim 93, wherein 5% to 40% by weight of the active pharmaceutical ingredient in the microsuspension is in dissolved form.

110. The ophthalmic microsuspension of claim 93, wherein 0% to 0.5% by weight of the active pharmaceutical ingredient in the microsuspension is in an uncomplexed solid form.

111. The ophthalmic microsuspension of claim 93, wherein the pH of the microsuspension is between about 5.0 and about 6.0.

112. The ophthalmic microsuspension of claim 93, wherein the microsuspension further comprises a polymer.

113. The ophthalmic microsuspension of claim 112, wherein the polymer is a surface active polymer.

114. The ophthalmic microsuspension of claim 113, wherein the polymer is selected from the group consisting of a polyoxyethylene fatty acid ester, a polyoxyethylene alkylphenyl ether, a polyoxyethylene alkyl ether, a cellulose derivative, a carboxyvinyl polymer, a polyvinyl polymer, a polyvinyl alcohol, a polyvinylpyrrolidone, a copolymer of polyoxypropylene and polyoxyethylene, tyloxapol, and combinations thereof.

115. The ophthalmic microsuspension of claim 114, wherein the copolymer of polyoxypropylene and polyoxyethylene is a triblock copolymer comprising a hydrophilic block-hydrophobic block-hydrophilic block configuration.

116. The ophthalmic microsuspension of claim 112, wherein the polymer is a poloxamer.

117. A method of preparing an ophthalmic microsuspension, the method comprising the steps of:
  a) forming a suspension or a solution of an active pharmaceutical ingredient in a first ophthalmically acceptable medium by heating a suspension of the active ingredient in said medium until the active pharmaceutical ingredient is dissolved, or substantially dissolved in the first ophthalmically acceptable medium and a solution or a suspension is formed;
  b) forming a suspension or a solution of a cyclodextrin in a second ophthalmically acceptable medium by heating a suspension of said cyclodextrin until the cyclodextrin is dissolved or substantially dissolved in the second ophthalmically acceptable medium and a solution or a suspension is formed; and
  c) mixing the suspensions or solutions of steps a) and b) at a temperature T1 and heating the mixture at a temperature higher than the temperature T1 and lower than 120° C. to obtain a resulting mixture, wherein the temperature T1 is from 80° C. to less than 120° C., and
  d) cooling the resulting mixture to a temperature T2 to obtain the ophthalmic microsuspension comprising a solid complex of the active pharmaceutical ingredient and cyclodextrin,
  wherein said solid complex has a diameter $D_{50}$ from about 1 μm to about 25 μm,
  wherein said active pharmaceutical ingredient is a steroid, and
  wherein the microsuspension comprises less than 1% by weight of by-products of the active pharmaceutical ingredient based on the weight of the active pharmaceutical ingredient.

118. The method of claim 117, wherein the suspension or solution of the active pharmaceutically ingredient of step a) and/or the suspension or solution of cyclodextrin of step b) are sterilized in an autoclave prior to their mixing in step c).

119. The method of claim 117, wherein the temperature T1 is from 80° C. to 110° C.

120. The method of claim 119, wherein the temperature T1 is from 85° C. to 105° C.

121. The method of claim 117, wherein in step d), the temperature T2 is 10° C. to 40° C.

122. The method of claim 117, wherein step d) comprises cooling the resulting mixture to the temperature T2 at a rate of 1° C./min to 25° C./min.

123. The method of claim 117, wherein the first and second ophthalmically acceptable media are selected from the group consisting of water, a preservative, a stabilizing agent, an electrolyte, a buffering agent, and combinations thereof.

124. The method of claim 117, wherein the first ophthalmically acceptable media is water and the second ophthalmically acceptable media comprises water, and optionally, an additive selected from the group consisting of a preservative, a stabilizing agent, an electrolyte, a buffering agent, and combinations thereof.

125. The method of claim 117, wherein the steroid is selected from the group consisting of dexamethasone, difluprednate, estradiol, fluocinolone, fluorometholone, hydrocortisone, loteprednol etabonate, prednisolone, triamcinolone, rimexolone, and combinations thereof.

126. The method of claim 125, wherein the steroid is dexamethasone.

127. The method of claim 117, wherein the cyclodextrin is α-cyclodextrin, β-cyclodextrin, γ-cyclodextrin, or a combination thereof.

128. The method of claim 127, wherein the cyclodextrin is γ-cyclodextrin.

129. The method of claim 117, wherein the amount of cyclodextrin is from 1% to 25% by weight based on the volume of the microsuspension.

130. The method of claim 117, wherein the active pharmaceutical ingredient is present in the microsuspension at a concentration of about 0.1 mg/mL to about 100 mg/mL.

131. The method of claim 130, wherein the active pharmaceutical ingredient is present in the microsuspension at a concentration of 10 mg/mL to 50 mg/mL.

132. The method of claim 117, wherein 60% to 95% by weight of the active pharmaceutical ingredient in the composition microsuspension is in the form of the solid complex.

133. The method of claim 117, wherein 5% to 40% by weight of the active pharmaceutical ingredient in the microsuspension is in dissolved form.

134. The method of claim 117, wherein 0% to 0.5% by weight of the active pharmaceutical ingredient in the microsuspension is in an uncomplexed solid form.

135. The method of claim 117, wherein the pH of the microsuspension is between about 5.0 and about 6.0.

136. The method of claim 117, wherein the microsuspension further comprises a polymer.

137. The method of claim 136, wherein the polymer is a surface active polymer.

138. The method of claim 137, wherein the polymer is selected from the group consisting of a polyoxyethylene fatty acid ester, a polyoxyethylene alkylphenyl ether, a polyoxyethylene alkyl ether, a cellulose derivative, a carboxyvinyl polymer, a polyvinyl polymer, a polyvinyl alcohol, a polyvinylpyrrolidone, a copolymer of polyoxypropylene and polyoxyethylene, tyloxapol, and combinations thereof.

139. The method of claim 138, wherein the copolymer of polyoxypropylene and polyoxyethylene is a triblock copolymer comprising a hydrophilic block-hydrophobic block-hydrophilic block configuration.

140. The method of claim 136, wherein the polymer is a poloxamer.

141. An ophthalmic microsuspension comprising, in an ophthalmically acceptable medium:
a solid complex comprising an active pharmaceutical ingredient and a cyclodextrin,
wherein the active pharmaceutical ingredient is a steroid,
wherein said solid complex has a diameter $D_{50}$ from about 1 μm to about 25 μm,
wherein the microsuspension comprises less than 1% by weight of degradation products of the active pharmaceutical ingredient based on the weight of the active pharmaceutical ingredient, and
wherein the microsuspension is prepared by a process comprising:

a) suspending the active pharmaceutical ingredient in a first ophthalmically acceptable medium and forming a suspension or solution of the active pharmaceutical ingredient by heating said suspension until the active pharmaceutical ingredient is dissolved or substantially dissolved in the first ophthalmically acceptable medium;
b) suspending the cyclodextrin in a second ophthalmically acceptable medium and forming a suspension or solution of the cyclodextrin by heating said suspension until the cyclodextrin is dissolved or substantially dissolved in the second ophthalmically acceptable medium; and
c) mixing the suspensions or solutions of steps a) and b) at a temperature T1 and heating the mixture at a temperature higher than the temperature T1 and lower than 120° C. to obtain a resulting mixture, wherein the temperature T1 is from 80° C. to less than 120° C., and
d) cooling the resulting mixture to a temperature T2 to obtain the ophthalmic microsuspension comprising the solid complex.

142. The ophthalmic microsuspension of claim 141, wherein the suspension or solution of the active pharmaceutically ingredient of step a) and/or the suspension or solution of cyclodextrin of step b) are sterilized in an autoclave prior to their mixing in step c).

143. The ophthalmic microsuspension of claim 141, wherein the temperature T1 is from 80° C. to 110° C.

144. The ophthalmic microsuspension of claim 143, wherein the temperature T1 is from 85° C. to 105° C.

145. The ophthalmic microsuspension of claim 141, wherein in step d), the temperature T2 is from 10° C. to 40° C.

146. The ophthalmic microsuspension of claim 141, wherein step d) comprises cooling the resulting mixture to the temperature T2 at a rate of 1° C./min to 25° C./min.

147. The ophthalmic microsuspension of claim 141, wherein the first and second ophthalmically acceptable media are selected from the group consisting of water, a preservative, a stabilizing agent, an electrolyte, a buffering agent, and combinations thereof.

148. The ophthalmic microsuspension of claim 141, wherein the first ophthalmically acceptable media is water and the second ophthalmically acceptable media comprises water, and optionally, an additive selected from the group consisting of a preservative, a stabilizing agent, an electrolyte, a buffering agent, and combinations thereof.

149. The ophthalmic microsuspension of claim 141, wherein the steroid is selected from the group consisting of dexamethasone, difluprednate, estradiol, fluocinolone, fluorometholone, hydrocortisone, loteprednol etabonate, prednisolone, triamcinolone, rimexolone, and combinations thereof.

150. The ophthalmic microsuspension of claim 149, wherein the steroid is dexamethasone.

151. The ophthalmic microsuspension of claim 141, wherein the cyclodextrin is α-cyclodextrin, β-cyclodextrin, γ-cyclodextrin, or a combination thereof.

152. The ophthalmic microsuspension of claim 151, wherein the cyclodextrin is γ-cyclodextrin.

153. The ophthalmic microsuspension of claim 141, wherein the amount of cyclodextrin is from 1% to 25% by weight based on the volume of the microsuspension.

154. The ophthalmic microsuspension of claim 141, wherein the active pharmaceutical ingredient is present in the microsuspension at a concentration of about 0.1 mg/mL to about 100 mg/mL.

155. The ophthalmic microsuspension of claim 154, wherein the active pharmaceutical ingredient is present in the microsuspension at a concentration of 10 mg/mL to 50 mg/mL.

156. The ophthalmic microsuspension of claim 141, wherein 60% to 95% by weight of the active pharmaceutical ingredient in the microsuspension is in the form of the solid complex.

157. The ophthalmic microsuspension of claim 141, wherein 5% to 40% by weight of the active pharmaceutical ingredient in the microsuspension is in dissolved form.

158. The ophthalmic microsuspension of claim 141, wherein 0% to 0.5% by weight of the active pharmaceutical ingredient in the microsuspension is in an uncomplexed solid form.

159. The ophthalmic microsuspension of claim 141, wherein the pH of the microsuspension is between about 5.0 and about 6.0.

160. The ophthalmic microsuspension of claim 141, wherein the microsuspension further comprises a polymer.

161. The ophthalmic microsuspension of claim 160, wherein the polymer is a surface active polymer.

162. The ophthalmic microsuspension of claim 161, wherein the polymer is selected from the group consisting of a polyoxyethylene fatty acid ester, a polyoxyethylene alkylphenyl ether, a polyoxyethylene alkyl ether, a cellulose derivative, a carboxyvinyl polymer, a polyvinyl polymer, a polyvinyl alcohol, a polyvinylpyrrolidone, a copolymer of polyoxypropylene and polyoxyethylene, tyloxapol, and combinations thereof.

163. The ophthalmic microsuspension of claim 162, wherein the copolymer of polyoxypropylene and polyoxyethylene is a triblock copolymer comprising a hydrophilic block-hydrophobic block-hydrophilic block configuration.

164. The ophthalmic microsuspension of claim 160, wherein the polymer is a poloxamer.

165. A method of preparing an ophthalmic microsuspension, the method comprising the steps of:
a) forming a suspension or solution of an active pharmaceutical ingredient by suspending said active pharmaceutical ingredient in a first ophthalmically acceptable medium to form a suspension of the active pharmaceutical ingredient and heating said suspension until the active pharmaceutical ingredient is dissolved or substantially dissolved in the first ophthalmically acceptable medium and a solution or a suspension is formed;
b) forming a suspension or solution of a cyclodextrin by suspending a cyclodextrin in a second ophthalmically acceptable medium to form a suspension of the cyclodextrin and heating said suspension until the cyclodextrin is dissolved or substantially dissolved in the second ophthalmically acceptable medium and a solution or a suspension is formed;
c) mixing the suspensions or solutions of steps a) and b) at a temperature T1 and heating the mixture at a temperature higher than the temperature T1 and lower than 120° C. to obtain a resulting mixture, and
d) cooling the resulting mixture to a temperature T2 to obtain the ophthalmic microsuspension comprising a solid complex of the active pharmaceutical ingredient and cyclodextrin,
wherein said solid complex has a diameter $D_{50}$ from about 1 µm to about 25 µm,
wherein said active pharmaceutical ingredient is a steroid, and wherein the microsuspension comprises less than 1% by weight of degradation products of the active pharmaceutical ingredient based on the weight of the active pharmaceutical ingredient.

166. The method of claim 165, wherein the suspension or solution of the active pharmaceutically ingredient of step a) and/or the suspension or solution of cyclodextrin of step b) are sterilized in an autoclave prior to their mixing in step c).

167. The method of claim 165, wherein the temperature T1 is from 80° C. to 110° C.

168. The method of claim 167, wherein the temperature T1 is from 85° C. to 105° C.

169. The method of claim 165, wherein in step d), the temperature T2 is from 10° C. to 40° C.

170. The method of claim 165, wherein step d) comprises cooling the resulting mixture to the temperature T2 at a rate of 1° C./min to 25° C./min.

171. The method of claim 165, wherein the first and second ophthalmically acceptable media are selected from the group consisting of water, a preservative, a stabilizing agent, an electrolyte, a buffering agent, and combinations thereof.

172. The method of claim 171, wherein the first ophthalmically acceptable media is water and the second ophthalmically acceptable media comprises water, and optionally, an additive selected from the group consisting of a preservative, a stabilizing agent, an electrolyte, a buffering agent, and combinations thereof.

173. The method of claim 165, wherein the steroid is selected from the group consisting of dexamethasone, difluprednate, estradiol, fluocinolone, fluorometholone, hydrocortisone, loteprednol etabonate, prednisolone, triamcinolone, rimexolone, and combinations thereof.

174. The method of claim 173, wherein the steroid is dexamethasone.

175. The method of claim 165, wherein the cyclodextrin is α-cyclodextrin, β-cyclodextrin, γ-cyclodextrin, or a combination thereof.

176. The method of claim 175, wherein the cyclodextrin is γ-cyclodextrin.

177. The method of claim 165, wherein the amount of cyclodextrin is from 1% to 25% by weight based on the volume of the microsuspension.

178. The method of claim 165, wherein the active pharmaceutical ingredient is present in the microsuspension at a concentration of about 0.1 mg/mL to about 100 mg/mL.

179. The method of claim 178, wherein the active pharmaceutical ingredient is present in the microsuspension at a concentration of 10 mg/mL to 50 mg/mL.

180. The method of claim 165, wherein 60% to 95% by weight of the active pharmaceutical ingredient in the microsuspension is in the form of the solid complex.

181. The method of claim 165, wherein 5% to 40% by weight of the active pharmaceutical ingredient in the microsuspension is in dissolved form.

182. The method of claim 165, wherein 0% to 0.5% by weight of the active pharmaceutical ingredient in the microsuspension is in an uncomplexed solid form.

183. The method of claim 165, wherein the pH of the microsuspension is between about 5.0 and about 6.0.

184. The method of claim 165, wherein the microsuspension further comprises a polymer.

185. The method of claim 184, wherein the polymer is a surface active polymer.

186. The method of claim 185, wherein the polymer is selected from the group consisting of a polyoxyethylene fatty acid ester, a polyoxyethylene alkylphenyl ether, a polyoxyethylene alkyl ether, a cellulose derivative, a carboxyvinyl polymer, a polyvinyl polymer, a polyvinyl alcohol, a polyvinylpyrrolidone, a copolymer of polyoxypropylene and polyoxyethylene, tyloxapol, and combinations thereof.

187. The method of claim 186, wherein the copolymer of polyoxypropylene and polyoxyethylene is a triblock copolymer comprising a hydrophilic block-hydrophobic block-hydrophilic block configuration.

188. The method of claim 184, wherein the polymer is a poloxamer.

189. An ophthalmic microsuspension comprising, in an ophthalmically acceptable medium:
  a solid complex comprising an active pharmaceutical ingredient and a cyclodextrin,
  wherein said solid complex has a diameter $D_{50}$ from about 1 µm to about 25 µm,
  wherein the active pharmaceutical ingredient is dexamethasone,
  wherein the microsuspension comprises less than 1% by weight of by-products of the active pharmaceutical ingredient based on the weight of the active pharmaceutical ingredient, and
  wherein the microsuspension is prepared by a process comprising:
  a) mixing a sterile suspension or solution of the active pharmaceutical ingredient and a sterile suspension or solution of the cyclodextrin at a temperature T1 for a time t until the active pharmaceutical ingredient and the cyclodextrin are substantially dissolved to form a resulting mixture, wherein the temperature T1 is from 80° C. to less than 120° C.; and
  b) cooling the resulting mixture to obtain the ophthalmic microsuspension comprising the solid complex.

190. The ophthalmic microsuspension of claim 189, wherein the sterile suspension or solution of the active pharmaceutical ingredient and/or the sterile suspension or solution of cyclodextrin are sterilized in an autoclave prior to mixing.

191. The ophthalmic microsuspension of claim 189, wherein the temperature T1 is from 80° C. to 110° C.

192. The ophthalmic microsuspension of claim 191, wherein the temperature T1 is from 85° C. to 105° C.

193. The ophthalmic microsuspension of claim 189, wherein in step b), cooling the resulting mixture comprises reducing the temperature T1 to a temperature T2, and wherein the temperature T2 is from 10° C. to 40° C.

194. The ophthalmic microsuspension of claim 193, wherein in step b), cooling the resulting mixture comprises reducing the temperature T1 to the temperature T2 at a rate of 1° C./min to 25° C./min.

195. The ophthalmic microsuspension of claim 189, wherein the time t is from 5 minutes to 2 hours.

196. The ophthalmic microsuspension of claim 189, wherein the cyclodextrin is α-cyclodextrin, β-cyclodextrin, γ-cyclodextrin, or a combination thereof.

197. The ophthalmic microsuspension of claim 196, wherein the cyclodextrin is γ-cyclodextrin.

198. The ophthalmic microsuspension of claim 189, wherein the amount of cyclodextrin is from 1% to 25% by weight based on the volume of the microsuspension.

199. The ophthalmic microsuspension of claim 189, wherein the active pharmaceutical ingredient is present in the microsuspension at a concentration of about 0.1 mg/mL to about 100 mg/mL.

200. The ophthalmic microsuspension of claim 199, wherein the active pharmaceutical ingredient is present in the microsuspension at a concentration of 10 mg/mL to 50 mg/mL.

201. The ophthalmic microsuspension of claim 189, wherein 60% to 95% by weight of the active pharmaceutical ingredient in the microsuspension is in the form of the solid complex.

202. The ophthalmic microsuspension of claim 189, wherein 5% to 40% by weight of the active pharmaceutical ingredient in the microsuspension is in dissolved form.

203. The ophthalmic microsuspension of claim 189, wherein 0% to 0.5% by weight of the active pharmaceutical ingredient in the microsuspension is in an uncomplexed solid form.

204. The ophthalmic microsuspension of claim 189, wherein the pH of the microsuspension is between about 5.0 and about 6.0.

205. The ophthalmic microsuspension of claim 189, wherein the microsuspension further comprises a polymer.

206. The ophthalmic microsuspension of claim 205, wherein the polymer is a surface active polymer.

207. The ophthalmic microsuspension of claim 206, wherein the polymer is selected from the group consisting of a polyoxyethylene fatty acid ester, a polyoxyethylene alkylphenyl ether, a polyoxyethylene alkyl ether, a cellulose derivative, a carboxyvinyl polymer, a polyvinyl polymer, a polyvinyl alcohol, a polyvinylpyrrolidone, a copolymer of polyoxypropylene and polyoxyethylene, tyloxapol, and combinations thereof.

208. The ophthalmic microsuspension of claim 207, wherein the copolymer of polyoxypropylene and polyoxyethylene is a triblock copolymer comprising a hydrophilic block-hydrophobic block-hydrophilic block configuration.

209. The ophthalmic microsuspension of claim 205, wherein the polymer is a poloxamer.

210. A method of preparing an ophthalmic microsuspension, the method comprising the steps of:
  a) mixing a sterile suspension or solution of an active pharmaceutical ingredient and a sterile suspension or solution of cyclodextrin at a temperature T1 for a time t until the active pharmaceutical ingredient and the cyclodextrin are substantially dissolved to form a resulting mixture, wherein the temperature T1 is from 80° C. to less than 120° C.; and
  b) cooling the resulting mixture to obtain an ophthalmic microsuspension comprising a solid complex in an ophthalmically acceptable medium,
  wherein said solid complex has a diameter $D_{50}$ from about 1 µm to about 25 µm,
  wherein said active pharmaceutical ingredient is dexamethasone, and
  wherein the microsuspension comprises less than 1% by weight of by-products of the active pharmaceutical ingredient based on the weight of the active pharmaceutical ingredient.

211. The method of claim 210, wherein the sterile suspension or solution of the active pharmaceutical ingredient and/or the sterile suspension or solution of cyclodextrin are sterilized in an autoclave prior to mixing.

212. The method of claim 210, wherein the temperature T1 is from 80° C. to 110° C.

213. The method of claim 212, wherein the temperature T1 is from 85° C. to 105° C.

214. The method of claim 210, wherein in step b), cooling the resulting mixture comprises reducing the temperature T1 to a temperature T2, and wherein the temperature T2 is from 10° C. to 40° C.

215. The method of claim 214, wherein in step b), cooling the resulting mixture comprises reducing the temperature T1 to the temperature T2 at a rate of 1° C./min to 25° C./min.

216. The method of claim 210, wherein the time t is from 5 minutes to 2 hours.

217. The method of claim 210, wherein the cyclodextrin is α-cyclodextrin, β-cyclodextrin, γ-cyclodextrin, or a combination thereof.

218. The method of claim 29, wherein the cyclodextrin is γ-cyclodextrin.

219. The method of claim 210, wherein the amount of cyclodextrin is from 1% to 25% by weight based on the volume of the microsuspension.

220. The method of claim 210, wherein the active pharmaceutical ingredient is present in the microsuspension at a concentration of about 0.1 mg/mL to about 100 mg/mL.

221. The method of claim 220, wherein the active pharmaceutical ingredient is present in the microsuspension at a concentration of 10 mg/mL to 50 mg/mL.

222. The method of claim 210, wherein 60% to 95% by weight of the active pharmaceutical ingredient in the microsuspension is in the form of the solid complex.

223. The method of claim 210, wherein 5% to 40% by weight of the active pharmaceutical ingredient in the microsuspension is in dissolved form.

224. The method of claim 210, wherein 0% to 0.5% by weight of the active pharmaceutical ingredient in the microsuspension is in an uncomplexed solid form.

225. The method of claim 210, wherein the pH of the microsuspension is between about 5.0 and about 6.0.

226. The method of claim 210, wherein the microsuspension further comprises a polymer.

227. The method of claim 226, wherein the polymer is a surface active polymer.

228. The method of claim 227, wherein the polymer is selected from the group consisting of a polyoxyethylene fatty acid ester, a polyoxyethylene alkylphenyl ether, a polyoxyethylene alkyl ether, a cellulose derivative, a carboxyvinyl polymer, a polyvinyl polymer, a polyvinyl alcohol, a polyvinylpyrrolidone, a copolymer of polyoxypropylene and polyoxyethylene, tyloxapol, and combinations thereof.

229. The method of claim 228, wherein the copolymer of polyoxypropylene and polyoxyethylene is a triblock copolymer comprising a hydrophilic block-hydrophobic block-hydrophilic block configuration.

230. The method of claim 226, wherein the polymer is a poloxamer.

231. An ophthalmic microsuspension comprising, in an ophthalmically acceptable medium:
   a solid complex comprising an active pharmaceutical ingredient and a cyclodextrin,
   wherein said solid complex has a diameter $D_{50}$ from about 1 μm to about 25 μm,
   wherein said active pharmaceutical ingredient is dexamethasone,
   wherein the microsuspension comprises less than 1% by weight of degradation products of the active pharmaceutical ingredient based on the weight of the active pharmaceutical ingredient, and
   wherein the microsuspension is prepared by a process comprising:
   a) mixing a sterile suspension or solution of the active pharmaceutical ingredient and a sterile suspension or solution of the cyclodextrin at a temperature T1 for a time t until the active pharmaceutical ingredient and the cyclodextrin are substantially dissolved to form a resulting mixture, wherein the temperature T1 is from 80° C. to less than 120° C.; and
   b) cooling the resulting mixture to obtain the ophthalmic microsuspension comprising the solid complex.

232. The ophthalmic microsuspension of claim 231, wherein the sterile suspension or solution of the active pharmaceutical ingredient and/or the sterile suspension or solution of cyclodextrin are sterilized in an autoclave prior to mixing.

233. The ophthalmic microsuspension of claim 231, wherein the temperature T1 is from 80° C. to 110° C.

234. The ophthalmic microsuspension of claim 233, wherein the temperature T1 is from 85° C. to 105° C.

235. The ophthalmic microsuspension of claim 231, wherein in step b), cooling the resulting mixture comprises reducing the temperature T1 to a temperature T2, and wherein the temperature T2 is from 10° C. to 40° C.

236. The ophthalmic microsuspension of claim 235, wherein in step b), cooling the resulting mixture comprises reducing the temperature T1 to the temperature T2 at a rate of 1° C./min to 25° C./min.

237. The ophthalmic microsuspension of claim 231, wherein the time t is from 5 minutes to 2 hours.

238. The ophthalmic microsuspension of claim 231, wherein the cyclodextrin is α-cyclodextrin, β-cyclodextrin, γ-cyclodextrin, or a combination thereof.

239. The ophthalmic microsuspension of claim 238, wherein the cyclodextrin is γ-cyclodextrin.

240. The ophthalmic microsuspension of claim 231, wherein the amount of cyclodextrin is from 1% to 25% by weight based on the volume of the microsuspension.

241. The ophthalmic microsuspension of claim 231, wherein the active pharmaceutical ingredient is present in the microsuspension at a concentration of about 0.1 mg/mL to about 100 mg/mL.

242. The ophthalmic microsuspension of claim 239, wherein the active pharmaceutical ingredient is present in the microsuspension at a concentration of 10 mg/mL to 50 mg/mL.

243. The ophthalmic microsuspension of claim 231, wherein 60% to 95% by weight of the active pharmaceutical ingredient in the microsuspension is in the form of the solid complex.

244. The ophthalmic microsuspension of claim 231, wherein 5% to 40% by weight of the active pharmaceutical ingredient in the microsuspension is in dissolved form.

245. The ophthalmic microsuspension of claim 231, wherein 0% to 0.5% by weight of the active pharmaceutical ingredient in the microsuspension is in an uncomplexed solid form.

246. The ophthalmic microsuspension of claim 231, wherein the pH of the microsuspension is between about 5.0 and about 6.0.

247. The ophthalmic microsuspension of claim 231, wherein the microsuspension further comprises a polymer.

248. The ophthalmic microsuspension of claim 247, wherein the polymer is a surface active polymer.

249. The ophthalmic microsuspension of claim 248, wherein the polymer is selected from the group consisting of a polyoxyethylene fatty acid ester, a polyoxyethylene alkylphenyl ether, a polyoxyethylene alkyl ether, a cellulose derivative, a carboxyvinyl polymer, a polyvinyl polymer, a polyvinyl alcohol, a polyvinylpyrrolidone, a copolymer of polyoxypropylene and polyoxyethylene, tyloxapol, and combinations thereof.

250. The ophthalmic microsuspension of claim 249, wherein the copolymer of polyoxypropylene and polyoxyethylene is a triblock copolymer comprising a hydrophilic block-hydrophobic block-hydrophilic block configuration.

251. The ophthalmic microsuspension of claim 245, wherein the polymer is a poloxamer.

252. A method of preparing an ophthalmic microsuspension, the method comprising the steps of:
a) mixing a sterile suspension or solution of an active pharmaceutical ingredient and a sterile suspension or solution of a cyclodextrin at a temperature T1 for a time t until the active pharmaceutical ingredient and the cyclodextrin are substantially dissolved to form a resulting mixture, wherein the temperature T1 is from 80° C. to less than 120° C.; and
b) cooling the resulting mixture to obtain an ophthalmic microsuspension comprising a solid complex of the active pharmaceutical ingredient and the cyclodextrin in an ophthalmically acceptable medium,
wherein said solid complex has a diameter $D_{50}$ from about 1 µm to about 25 µm,
wherein said active pharmaceutical ingredient is dexamethasone,
and
wherein the microsuspension comprises less than 1% by weight of degradation products of the active pharmaceutical ingredient based on the weight of the active pharmaceutical ingredient.

253. The method of claim 252, wherein the sterile suspension or solution of the active pharmaceutical ingredient and/or the sterile suspension or solution of cyclodextrin are sterilized in an autoclave prior to mixing.

254. The method of claim 252, wherein the temperature T1 is from 80° C. to 110° C.

255. The method of claim 254, wherein the temperature T1 is from 85° C. to 105° C.

256. The method of claim 252, wherein in step b), cooling the resulting mixture comprises reducing the temperature T1 to a temperature T2, and wherein the temperature T2 is from 10° C. to 40° C.

257. The method of claim 256, wherein in step b), cooling the resulting mixture comprises reducing the temperature T1 to the temperature T2 at a rate of 1° C./min to 25° C./min.

258. The method of claim 252, wherein the time t is from 5 minutes to 2 hours.

259. The method of claim 252, wherein the cyclodextrin is α-cyclodextrin, β-cyclodextrin, γ-cyclodextrin, or a combination thereof.

260. The method of claim 257, wherein the cyclodextrin is γ-cyclodextrin.

261. The method of claim 252, wherein the amount of cyclodextrin is from 1% to 25% by weight based on the volume of the microsuspension.

262. The method of claim 252, wherein the active pharmaceutical ingredient is present in the microsuspension at a concentration of about 0.1 mg/mL to about 100 mg/mL.

263. The method of claim 262, wherein the active pharmaceutical ingredient is present in the microsuspension at a concentration of 10 mg/mL to 50 mg/mL.

264. The method of claim 252, wherein 60% to 95% by weight of the active pharmaceutical ingredient in the microsuspension is in the form of the solid complex.

265. The method of claim 252, wherein 5% to 40% by weight of the active pharmaceutical ingredient in the microsuspension is in dissolved form.

266. The method of claim 252, wherein 0% to 0.5% by weight of the active pharmaceutical ingredient in the microsuspension is in an uncomplexed solid form.

267. The method of claim 252, wherein the pH of the microsuspension is between about 5.0 and about 6.0.

268. The method of claim 252, wherein the microsuspension further comprises a polymer.

269. The method of claim 268, wherein the polymer is a surface active polymer.

270. The method of claim 269, wherein the polymer is selected from the group consisting of a polyoxyethylene fatty acid ester, a polyoxyethylene alkylphenyl ether, a polyoxyethylene alkyl ether, a cellulose derivative, a carboxyvinyl polymer, a polyvinyl polymer, a polyvinyl alcohol, a polyvinylpyrrolidone, a copolymer of polyoxypropylene and polyoxyethylene, tyloxapol, and combinations thereof.

271. The method of claim 270, wherein the copolymer of polyoxypropylene and polyoxyethylene is a triblock copolymer comprising a hydrophilic block-hydrophobic block-hydrophilic block configuration.

272. The method of claim 268, wherein the polymer is a poloxamer.

273. An ophthalmic microsuspension comprising, in an ophthalmically acceptable medium:
a solid complex comprising an active pharmaceutical ingredient and a cyclodextrin,
wherein the active pharmaceutical ingredient is dexamethasone,
wherein said solid complex has a diameter $D_{50}$ from about 1 µm to about 25 µm,
wherein the microsuspension comprises less than 1% by weight of by-products of the active pharmaceutical ingredient based on the weight of the active pharmaceutical ingredient, and
wherein the microsuspension is prepared by a process comprising:
a) suspending the active pharmaceutical ingredient in a first ophthalmically acceptable medium to form a suspension of the active pharmaceutical ingredient and heating said suspension until the active pharmaceutical ingredient is dissolved or substantially dissolved in the first ophthalmically acceptable medium and a solution or a suspension is formed;
b) suspending the cyclodextrin in a second ophthalmically acceptable medium to form a suspension of the cyclodextrin and heating said suspension until the cyclodextrin is dissolved or substantially dissolved in the second ophthalmically acceptable medium and a solution or a suspension is formed;
c) mixing the suspensions of steps a) and b) at a temperature T1 and heating the mixture at a temperature higher than the temperature T1 but lower than 120° C. to obtain a resulting mixture, wherein the temperature T1 is from 80° C. to less than 120° C., and
d) cooling the resulting mixture to a temperature T2 to obtain the ophthalmic microsuspension comprising the solid complex.

274. The ophthalmic microsuspension of claim 273, wherein the solution or suspension of the active pharmaceutically ingredient of step a) and/or the solution or suspension of cyclodextrin of step b) are sterilized in an autoclave prior to their mixing in step c).

275. The ophthalmic microsuspension of claim 273, wherein the temperature T1 is from 80° C. to 110° C.

276. The ophthalmic microsuspension of claim 275, wherein the temperature T1 is from 85° C. to 105° C.

277. The ophthalmic microsuspension of claim 273, wherein in step d), the temperature T2 is 10° C. to 40° C.

278. The ophthalmic microsuspension of claim 273, wherein step d) comprises cooling the resulting mixture to the temperature T2 at a rate of 1° C./min to 25° C./min.

279. The ophthalmic microsuspension of claim 273, wherein the first and second ophthalmically acceptable media are selected from the group consisting of water, a preservative, a stabilizing agent, an electrolyte, a buffering agent, and combinations thereof.

280. The ophthalmic microsuspension of claim 273, wherein the first ophthalmically acceptable media is water and the second ophthalmically acceptable media comprises water, and optionally, an additive selected from the group consisting of a preservative, a stabilizing agent, an electrolyte, a buffering agent, and combinations thereof.

281. The ophthalmic microsuspension of claim 273, wherein the cyclodextrin is α-cyclodextrin, β-cyclodextrin, γ-cyclodextrin, or a combination thereof.

282. The ophthalmic microsuspension of claim 281, wherein the cyclodextrin is γ-cyclodextrin.

283. The ophthalmic microsuspension of claim 273, wherein the amount of cyclodextrin is from 1% to 25% by weight based on the volume of the microsuspension.

284. The ophthalmic microsuspension of claim 273, wherein the active pharmaceutical ingredient is present in the microsuspension at a concentration of about 0.1 mg/mL to about 100 mg/mL.

285. The ophthalmic microsuspension of claim 284, wherein the active pharmaceutical ingredient is present in the microsuspension at a concentration of 10 mg/mL to 50 mg/mL.

286. The ophthalmic microsuspension of claim 273, wherein 60% to 95% by weight of the active pharmaceutical ingredient in the microsuspension is in the form of the solid complex.

287. The ophthalmic microsuspension of claim 273, wherein 5% to 40% by weight of the active pharmaceutical ingredient in the microsuspension is in dissolved form.

288. The ophthalmic microsuspension of claim 273, wherein 0% to 0.5% by weight of the active pharmaceutical ingredient in the microsuspension is in an uncomplexed solid form.

289. The ophthalmic microsuspension of claim 273, wherein the pH of the microsuspension is between about 5.0 and about 6.0.

290. The ophthalmic microsuspension of claim 273, wherein the microsuspension further comprises a polymer.

291. The ophthalmic microsuspension of claim 290, wherein the polymer is a surface active polymer.

292. The ophthalmic microsuspension of claim 291, wherein the polymer is selected from the group consisting of a polyoxyethylene fatty acid ester, a polyoxyethylene alkylphenyl ether, a polyoxyethylene alkyl ether, a cellulose derivative, a carboxyvinyl polymer, a polyvinyl polymer, a polyvinyl alcohol, a polyvinylpyrrolidone, a copolymer of polyoxypropylene and polyoxyethylene, tyloxapol, and combinations thereof.

293. The ophthalmic microsuspension of claim 292, wherein the copolymer of polyoxypropylene and polyoxyethylene is a triblock copolymer comprising a hydrophilic block-hydrophobic block-hydrophilic block configuration.

294. The ophthalmic microsuspension of claim 290, wherein the polymer is a poloxamer.

295. A method of preparing an ophthalmic microsuspension, the method comprising the steps of:
a) forming a suspension or a solution of an active pharmaceutical ingredient in a first ophthalmically acceptable medium by heating a suspension of the active ingredient in said medium until the active pharmaceutical ingredient is dissolved, or substantially dissolved in the first ophthalmically acceptable medium;
b) forming a suspension or a solution of a cyclodextrin in a second ophthalmically acceptable medium by heating a suspension of said cyclodextrin until the cyclodextrin is dissolved or substantially dissolved in the second ophthalmically acceptable medium;
c) mixing the suspensions or solutions of steps a) and b) at a temperature T1 and heating the mixture at a temperature higher than the temperature T1 and lower than 120° C. to obtain a resulting mixture to obtain a resulting mixture, wherein the temperature T1 is from 80° C. to less than 120° C., and
d) cooling the resulting mixture to a temperature T2 to obtain the ophthalmic microsuspension comprising a solid complex of the active pharmaceutical ingredient and cyclodextrin,
wherein said solid complex has a diameter $D_{50}$ from about 1 μm to about 25 μm,
wherein said active pharmaceutical ingredient is dexamethasone, and
wherein the microsuspension comprises less than 1% by weight of by-products of the active pharmaceutical ingredient based on the weight of the active pharmaceutical ingredient.

296. The method of claim 295, wherein the suspension or solution of the active pharmaceutically ingredient of step a) and/or the suspension or solution of cyclodextrin of step b) are sterilized in an autoclave prior to their mixing in step c).

297. The method of claim 295, wherein the temperature T1 is from 80° C. to 110° C.

298. The method of claim 297, wherein the temperature T1 is from 85° C. to 105° C.

299. The method of claim 295, wherein in step d), the temperature T2 is 10° C. to 40° C.

300. The method of claim 295, wherein step d) comprises cooling the resulting mixture to the temperature T2 at a rate of 1° C./min to 25° C./min.

301. The method of claim 295, wherein the first and second ophthalmically acceptable media are selected from the group consisting of water, a preservative, a stabilizing agent, an electrolyte, a buffering agent, and combinations thereof.

302. The method of claim 295, wherein the first ophthalmically acceptable media is water and the second ophthalmically acceptable media comprises water, and optionally, an additive selected from the group consisting of a preservative, a stabilizing agent, an electrolyte, a buffering agent, and combinations thereof.

303. The method of claim 295, wherein the cyclodextrin is α-cyclodextrin, β-cyclodextrin, γ-cyclodextrin, or a combination thereof.

304. The method of claim 303, wherein the cyclodextrin is γ-cyclodextrin.

305. The method of claim 295, wherein the amount of cyclodextrin is from 1% to 25% by weight based on the volume of the microsuspension.

306. The method of claim 295, wherein the active pharmaceutical ingredient is present in the microsuspension at a concentration of about 0.1 mg/mL to about 100 mg/mL.

307. The method of claim 306, wherein the active pharmaceutical ingredient is present in the microsuspension at a concentration of 10 mg/mL to 50 mg/mL.

308. The method of claim 295, wherein 60% to 95% by weight of the active pharmaceutical ingredient in the composition microsuspension is in the form of the solid complex.

309. The method of claim 295, wherein 5% to 40% by weight of the active pharmaceutical ingredient in the microsuspension is in dissolved form.

310. The method of claim 295, wherein 0% to 0.5% by weight of the active pharmaceutical ingredient in the microsuspension is in an uncomplexed solid form.

311. The method of claim 295, wherein the pH of the microsuspension is between about 5.0 and about 6.0.

312. The method of claim 295, wherein the microsuspension further comprises a polymer.

313. The method of claim 312, wherein the polymer is a surface active polymer.

314. The method of claim 313, wherein the polymer is selected from the group consisting of a polyoxyethylene fatty acid ester, a polyoxyethylene alkylphenyl ether, a polyoxyethylene alkyl ether, a cellulose derivative, a carboxyvinyl polymer, a polyvinyl polymer, a polyvinyl alcohol, a polyvinylpyrrolidone, a copolymer of polyoxypropylene and polyoxyethylene, tyloxapol, and combinations thereof.

315. The method of claim 314, wherein the copolymer of polyoxypropylene and polyoxyethylene is a triblock copolymer comprising a hydrophilic block-hydrophobic block-hydrophilic block configuration.

316. The method of claim 312, wherein the polymer is a poloxamer.

317. An ophthalmic microsuspension comprising, in an ophthalmically acceptable medium:
a solid complex comprising an active pharmaceutical ingredient and a cyclodextrin,
wherein the active pharmaceutical ingredient is dexamethasone,
wherein said solid complex has a diameter $D_{50}$ from about 1 μm to about 25 μm,
wherein the microsuspension comprises less than 1% by weight of degradation products of the active pharmaceutical ingredient based on the weight of the active pharmaceutical ingredient, and
wherein the microsuspension is prepared by a process comprising:
a) suspending the active pharmaceutical ingredient in a first ophthalmically acceptable medium and forming a suspension or solution of the active pharmaceutical ingredient by heating said suspension until the active pharmaceutical ingredient is dissolved or substantially dissolved in the first ophthalmically acceptable medium and a solution or a suspension is formed;
b) suspending the cyclodextrin in a second ophthalmically acceptable medium and forming a suspension or solution of the cyclodextrin by heating said suspension until the cyclodextrin is dissolved or substantially dissolved in the second ophthalmically acceptable medium and a solution or a suspension is formed;
c) mixing the suspensions or solutions of steps a) and b) at a temperature T1 and heating the mixture at a temperature higher than the temperature T1 and lower than 120° C. to obtain a resulting mixture, wherein the temperature T1 is from 80° C. to less than 120° C., and
d) cooling the resulting mixture to a temperature T2 to obtain the ophthalmic microsuspension comprising the solid complex.

318. The ophthalmic microsuspension of claim 317, wherein the suspension or solution of the active pharmaceutically ingredient of step a) and/or the suspension or solution of cyclodextrin of step b) are sterilized in an autoclave prior to their mixing in step c).

319. The ophthalmic microsuspension of claim 317, wherein the temperature T1 is from 80° C. to 110° C.

320. The ophthalmic microsuspension of claim 319, wherein the temperature T1 is from 85° C. to 105° C.

321. The ophthalmic microsuspension of claim 317, wherein in step d), the temperature T2 is from 10° C. to 40° C.

322. The ophthalmic microsuspension of claim 317, wherein step d) comprises cooling the resulting mixture to the temperature T2 at a rate of 1° C./min to 25° C./min.

323. The ophthalmic microsuspension of claim 317, wherein the first and second ophthalmically acceptable media are selected from the group consisting of water, a preservative, a stabilizing agent, an electrolyte, a buffering agent, and combinations thereof.

324. The ophthalmic microsuspension of claim 317, wherein the first ophthalmically acceptable media is water and the second ophthalmically acceptable media comprises water, and optionally, an additive selected from the group consisting of a preservative, a stabilizing agent, an electrolyte, a buffering agent, and combinations thereof.

325. The ophthalmic microsuspension of claim 317, wherein the cyclodextrin is α-cyclodextrin, β-cyclodextrin, γ-cyclodextrin, or a combination thereof.

326. The ophthalmic microsuspension of claim 325, wherein the cyclodextrin is γ-cyclodextrin.

327. The ophthalmic microsuspension of claim 317, wherein the amount of cyclodextrin is from 1% to 25% by weight based on the volume of the microsuspension.

328. The ophthalmic microsuspension of claim 317, wherein the active pharmaceutical ingredient is present in the microsuspension at a concentration of about 0.1 mg/mL to about 100 mg/mL.

329. The ophthalmic microsuspension of claim 328, wherein the active pharmaceutical ingredient is present in the microsuspension at a concentration of 10 mg/mL to 50 mg/mL.

330. The ophthalmic microsuspension of claim 317, wherein 60% to 95% by weight of the active pharmaceutical ingredient in the microsuspension is in the form of the solid complex.

331. The ophthalmic microsuspension of claim 317, wherein 5% to 40% by weight of the active pharmaceutical ingredient in the microsuspension is in dissolved form.

332. The ophthalmic microsuspension of claim 317, wherein 0% to 0.5% by weight of the active pharmaceutical ingredient in the microsuspension is in an uncomplexed solid form.

333. The ophthalmic microsuspension of claim 317, wherein the pH of the microsuspension is between about 5.0 and about 6.0.

334. The ophthalmic microsuspension of claim 317, wherein the microsuspension further comprises a polymer.

335. The ophthalmic microsuspension of claim 334, wherein the polymer is a surface active polymer.

336. The ophthalmic microsuspension of claim 335, wherein the polymer is selected from the group consisting of a polyoxyethylene fatty acid ester, a polyoxyethylene alkylphenyl ether, a polyoxyethylene alkyl ether, a cellulose derivative, a carboxyvinyl polymer, a polyvinyl polymer, a polyvinyl alcohol, a polyvinylpyrrolidone, a copolymer of polyoxypropylene and polyoxyethylene, tyloxapol, and combinations thereof.

337. The ophthalmic microsuspension of claim 336, wherein the copolymer of polyoxypropylene and polyoxyethylene is a triblock copolymer comprising a hydrophilic block-hydrophobic block-hydrophilic block configuration.

338. The ophthalmic microsuspension of claim 334, wherein the polymer is a poloxamer.

339. A method of preparing an ophthalmic microsuspension, the method comprising the steps of:
- a) forming a suspension or solution of an active pharmaceutical ingredient by suspending said active pharmaceutical ingredient in a first ophthalmically acceptable medium to form a suspension of the active pharmaceutical ingredient and heating said suspension until the active pharmaceutical ingredient is dissolved or substantially dissolved in the first ophthalmically acceptable medium and a solution or a suspension is formed;
- b) forming a suspension or solution of a cyclodextrin by suspending a cyclodextrin in a second ophthalmically acceptable medium to form a suspension of the cyclodextrin and heating said suspension until the cyclodextrin is dissolved or substantially dissolved in the second ophthalmically acceptable medium and a solution or a suspension is formed;
- c) mixing the suspensions or solutions of steps a) and b) at a temperature T1 and heating the mixture at a temperature higher than the temperature T1 and lower than 120° C. to obtain a resulting mixture, and
- d) cooling the resulting mixture to a temperature T2 to obtain the ophthalmic microsuspension comprising a solid complex of the active pharmaceutical ingredient and cyclodextrin, wherein said solid complex has a diameter $D_{50}$ from about 1 μm to about 25 μm, wherein said active pharmaceutical ingredient is dexamethasone, and wherein the microsuspension comprises less than 1% by weight of degradation products of the active pharmaceutical ingredient based on the weight of the active pharmaceutical ingredient.

340. The method of claim 339, wherein the suspension or solution of the active pharmaceutically ingredient of step a) and/or the suspension or solution of cyclodextrin of step b) are sterilized in an autoclave prior to their mixing in step c).

341. The method of claim 339, wherein the temperature T1 is from 80° C. to 110° C.

342. The method of claim 341, wherein the temperature T1 is from 85° C. to 105° C.

343. The method of claim 339, wherein in step d), the temperature T2 is from 10° C. to 40° C.

344. The method of claim 339, wherein step d) comprises cooling the resulting mixture to the temperature T2 at a rate of 1° C./min to 25° C./min.

345. The method of claim 339, wherein the first and second ophthalmically acceptable media are selected from the group consisting of water, a preservative, a stabilizing agent, an electrolyte, a buffering agent, and combinations thereof.

346. The method of claim 339, wherein the first ophthalmically acceptable media is water and the second ophthalmically acceptable media comprises water, and optionally, an additive selected from the group consisting of a preservative, a stabilizing agent, an electrolyte, a buffering agent, and combinations thereof.

347. The method of claim 339, wherein the cyclodextrin is α-cyclodextrin, β-cyclodextrin, γ-cyclodextrin, or a combination thereof.

348. The method of claim 347, wherein the cyclodextrin is γ-cyclodextrin.

349. The method of claim 339, wherein the amount of cyclodextrin is from 1% to 25% by weight based on the volume of the microsuspension.

350. The method of claim 339, wherein the active pharmaceutical ingredient is present in the microsuspension at a concentration of about 0.1 mg/mL to about 100 mg/mL.

351. The method of claim 350, wherein the active pharmaceutical ingredient is present in the microsuspension at a concentration of 10 mg/mL to 50 mg/mL.

352. The method of claim 339, wherein 60% to 95% by weight of the active pharmaceutical ingredient in the microsuspension is in the form of the solid complex.

353. The method of claim 339, wherein 5% to 40% by weight of the active pharmaceutical ingredient in the microsuspension is in dissolved form.

354. The method of claim 339, wherein 0% to 0.5% by weight of the active pharmaceutical ingredient in the microsuspension is in an uncomplexed solid form.

355. The method of claim 339, wherein the pH of the microsuspension is between about 5.0 and about 6.0.

356. The method of claim 339, wherein the microsuspension further comprises a polymer.

357. The method of claim 356, wherein the polymer is a surface active polymer.

358. The method of claim 357, wherein the polymer is selected from the group consisting of a polyoxyethylene fatty acid ester, a polyoxyethylene alkylphenyl ether, a polyoxyethylene alkyl ether, a cellulose derivative, a carboxyvinyl polymer, a polyvinyl polymer, a polyvinyl alcohol, a polyvinylpyrrolidone, a copolymer of polyoxypropylene and polyoxyethylene, tyloxapol, and combinations thereof.

359. The method of claim 358, wherein the copolymer of polyoxypropylene and polyoxyethylene is a triblock copolymer comprising a hydrophilic block-hydrophobic block-hydrophilic block configuration.

360. The method of claim 356 wherein the polymer is a poloxamer.

* * * * *